US008835360B1

(12) United States Patent
Mehta et al.

(10) Patent No.: US 8,835,360 B1
(45) Date of Patent: *Sep. 16, 2014

(54) COMBINATORIAL THERAPY FOR PROTEIN SIGNALING DISEASES

(75) Inventors: Arpita I. Mehta, Hoffman Estates, IL (US); Lance A. Liotta, Bethesda, MD (US); Emanuel F. Petricoin, Dunkirk, MD (US)

(73) Assignee: The United States of America as represented by the Secretary of the Department of HHS, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/455,111

(22) Filed: Apr. 24, 2012

Related U.S. Application Data

(63) Continuation of application No. 12/581,019, filed on Oct. 16, 2009, now Pat. No. 8,168,568, which is a continuation of application No. 10/798,799, filed on Mar. 10, 2004, now abandoned.

(60) Provisional application No. 60/453,629, filed on Mar. 10, 2003.

(51) Int. Cl.
*G01N 33/50* (2006.01)

(52) U.S. Cl.
USPC ........ 506/10; 506/9; 506/11; 506/12; 702/19; 435/6.19; 435/7.5

(58) Field of Classification Search
None
See application file for complete search history.

(56) References Cited

U.S. PATENT DOCUMENTS

| | | | |
|---|---|---|---|
| 5,843,657 | A | 12/1998 | Liotta et al. |
| 6,251,516 | B1 | 6/2001 | Bonner et al. |
| 6,262,044 | B1 | 7/2001 | Moller et al. |
| 6,316,462 | B1 | 11/2001 | Bishop et al. |
| 6,432,966 | B2 * | 8/2002 | Rubin et al. ............. 514/263.32 |
| 6,518,021 | B1 | 2/2003 | Thastrup et al. |
| 6,969,614 | B1 | 11/2005 | Liotta et al. |
| 7,236,888 | B2 | 6/2007 | Allbritton et al. |
| 2001/0031469 | A1 | 10/2001 | Volina |
| 2002/0137755 | A1 | 9/2002 | Bilodeau et al. |
| 2003/0124130 | A1 | 7/2003 | Brown |
| 2003/0153014 | A1 | 8/2003 | Shen et al. |
| 2003/0190689 | A1 | 10/2003 | Crosby et al. |
| 2005/0230315 | A1 | 10/2005 | Lubman et al. |
| 2005/0282849 | A1 | 12/2005 | Moon et al. |
| 2006/0040302 | A1 | 2/2006 | Botstein et al. |
| 2006/0084056 | A1 | 4/2006 | Harbeck et al. |

FOREIGN PATENT DOCUMENTS

| | | |
|---|---|---|
| WO | WO97/02360 | 1/1997 |
| WO | WO 97/02360 A1 | 1/1997 |
| WO | WO00/49410 | 8/2000 |
| WO | WO 00/49410 A2 | 8/2000 |
| WO | WO 2004/041164 A2 | 5/2004 |

OTHER PUBLICATIONS

Diao et al (2001 Cytokine and Growth Factor Reviews 12:189-205).*
Banks et al.; The potential use of laser capture microdissection to selectively obtain distinct populations of cells for proteomic analysis—preliminary findings. Electrophoresis, 20:689-700 (1999).
Bichsel et al.; Cancer proteomics: from biomarker discovery to signal pathway profiling. The Cancer Journal, 7 (1):69-78 (Jan./Feb. 2001).
Brightman et al., "4. Computer Simulation of Signal Transduction," Computer Simulation of EGF Signal Transduction, http://bms-mudshark.brookes.ac.uk/frances/fabweb5.htm (accessed on Oct. 29, 2002).
Brown Jones et al.; Proteomic analysis and identification of new biomarkers and therapeutic targets for invasive ovarian cancer. Proteomics, 2:76-84 (2002).
Burkhardt, "Research Summary—The Role of the Cytoskeleton in T Cell Function," http://cmp.bsd.uchicago.edu/faculty/jBurkhardt.html (accessed on Mar. 6, 2003).
Charboneau et al.; Technique Review—Utility of reverse phase protein arrays: applications to signaling pathways and human body arrays. Briefings in Functional Genomics and Proteomics, 1(3):305-315 (Oct. 2002).
Friedrich, M.J.; Genomics and proteomics may help clinicians individualize cancer treatment. Journal of American Medical Association, 287(22):2931-2932 (Jun. 12, 2002).
Igarashi et al., "Development of a Cell Signaling Networks Database" Pac Symp Biocomput, 187-97 (1997).
Jain, Kewal K.; Recent advances in oncoproteomics. Current Opinion in Molecular Therapeutics, 4(3):2003-209 (2002).
Krieg et al., Clinical proteomics for cancer biomarker discovery and therapeutic targeting. Tech in Cancer Res & Treatment 1(4): 263-272 (2002).
Ng, Jocelyn H.; Biomedical applications of protein chips. J. Cell. Mol. Med., 6(3): 329-340 (2002).
Ornstein et al.; Proteomic analysis of laser capture microdissected human prostate cancer and in vitro prostrate cell lines. Electrophoresis, 21:2235-2242 (2000).
Osin et al.; Experimental pathology and breast cancer genetics: new technologies. in Adjuvant Therapy of Primary Breast Cancer VI (HJ Senn et al., eds.), 35-48 (1998).

(Continued)

*Primary Examiner* — Christopher M Gross
(74) *Attorney, Agent, or Firm* — Geoffrey M. Karny

(57) ABSTRACT

A method for selecting combinations of drugs for treatment of diseases that arise from deranged signaling pathways is disclosed. The method involves measuring the activity states for signaling proteins in a diseased cell and determining whether the activity states are different from the activity states observed for a reference cell such as a normal cell. Based on the observed differences, combinations of two or more drugs are selected to reduce these differences. Treatment of a subject with the combinations restores the activity states of the signaling proteins of the deranged disease-associated signaling pathways toward the activity states observed in the reference cell. Since the diseased cell and the reference cell can both be obtained from the same subject, combinations of drugs that specifically target patient-specific signaling derangements is possible.

60 Claims, 25 Drawing Sheets

(56) References Cited

OTHER PUBLICATIONS

Simone et al.; Laser capture microdissection: beyond functional genomics to proteomics. Molecular Diagnosis, 5 (4):301-307 (2000).
Simpson et al.; Cancer proteomics: from signaling networks to tumor markers. TRENDS in Biotechnology, 19(1O):S40-S48 (Oct. 2001).
Von Eggeling et al.; Tissue-specific microdissection coupled with proteinchip® array technologies: applications in cancer research. BioTechniques, 29:1066-1070 (Nov. 2000).
Winters et al., "Supra-additive growth inhibition by a celecoxib analogue and carboxyamido-triazole is primarily mediated through apoptosis," Cancer Res 65(90); 3853-3860 (May 1, 2005).
Barnard, Epidermal Growth Factor Receptor Blockade: An Emerging Therapeutic Modality in Gastroenterology (2001 Gastroenterology 120: 1872-1874).
Bernardi et al., Combination of 1a,25-Dihydroxyvitamin D3 with Dexamethasone Enhances Cell Cycle Arrest and Apoptosis: Role of Nuclear Receptor Cross-Talk and Erk/Akt Signaling (2001 Clinical Cancer Research 7: 4164-4173).
Bonner et al. Enhanced Apoptosis With Combination C225/Radiation Treatment Serves as the Impetus for Clinical Investigation in Head and Neck Cancers (2000 J. Clinical Oncology 18:47S-53S).
Finley, New Directions in the Treatment of Cancer: Inhibition of Signal Transduction (2002 J. Pharmacy Practice 15:5-16).
Liotta and Petricoin, "Molecular Profiling of Human Cancer," Nature Reviews Genetics, 1:48-56 (Oct. 2000).
Mann et al., Targeting Cyclooxygenase 2 and HER-2/neu Pathways Inhibits Colorectal Carcinoma Growth (2001 Gastroenterology 120:1713-1719).
Nassar et al., "Structure-Function Based Design of Small Molecule Inhibitors Targeting Rho Family GTPases," 2006 Current Topics in Medicinal Chemistry 6:1109-1116.
Thornberry et al., "Caspases: Enemies Within," 1998 Science 281:1312-1316.
Torrance et al., Combinatorial chemoprevention of intestinal neoplasia (2000 Nature Medicine 6:1024-1028).
Tortora et al., "Combination of a Selective Cyclooxygenase-2 Inhibitor with Epidermal Growth Factor Receptor . . . Inhibitor . . . ," 2003 Clinical Cancer Res. 9:1566-1572.
Weng et al., Complexity in Biological Signaling Systems (1999 Science 284:92-96).
Xu et al., "Role of PKC and MAPK in cytosolic PLA2 phosphorylation and arachadonic acid release in primary murine astrocytes," Journal of Neurochemistry, 2002, 83, 259-270.
Ala-Uotila et al., "Use of a Hollow Fiber Bioreactor for Large-Scale Production of Alpha 2-Adrenoceptors in Mammalian Cells," *J. Biotechnol.* 37(2):179-184, Sep. 30, 1994 (abstract only).
Armstrong et al., "A RANKJTRAF6-Dependent Signal Transduction Pathway Is Essential for Osteoclast Cytoskeletal Organization and Resorptive Function," *The Journal of Biological Chemistry* 277(46):44347-44356, 2002.
Asthagiri et al., A Computational Study of Feedback Effects on Signal Dynamics in a Mitogen-Activated Protein Kinase (MAPK) Pathway Model, *Biotechnol. Prog.* 17(2):227 239,2001.
Asthagiri et al., "Bioengineering Models of Cell Signaling," *Annu. Rev. Biomed Eng* 2:31-53,2000 (abstract only).
Baker, "Editorial: Dying (Apoptosing?) for a Consensus on the Fas Death Pathway in the Thyroid," *The Journal of Clinical Endocrinology & Metabolism* 84(8):2593-2595, 1999.
Ballif et al., "Molecular Mechanisms Mediating Mammalian Mitogen-Activated Kinase (MAPK) Kinase (MEK)-MAPK Cell Survival Signals," *Cell Growth & Differentiation* 12:397-408, Aug. 2001.
Beck, Jr. et al., "Gene Array Analysis of Osteoblast Differentiation," *Cell Growth & Differentiation* 12:61-83, Feb. 2001 (abstract only).
Bhalla, "The Chemical Organization of Signaling Interactions," *Bioinformatics* 18(6):855.
Blanchetot et al., "Intra- and Intermolecular Interactions Between Intracellular Domains of Receptor Protein-Tyrosine Phosphatases," *The Journal of Biological Chemistry* 277(49):47263-47269, 2002.
Bond et al., "Tissue Inhibitor of Metalloproteinase-3 Induces a Fas-Associated Death Domain-Dependent Type II Apoptotic Pathway," *The Journal of Biological Chemistry* 277(16):13787-13795 2002.
Bondzi et al., "Src Family Kinase Activity Is Required for Kit-Mediated Mitogen-Activated Protein (MAP) Kinase Activation, However Loss of Functional Retinoblastoma Protein Makes MAP Kinase Activation Unnecessary for Growth of Small Cell Lung Cancer Cells," *Cell Growth & Differentiation* 11:305-314, Jun. 2000.
Brennan et al., "Phosphorylation Regulates the Nucleocytoplasmic Distribution of Kinase Suppressor of Ras," *The Journal of Biological Chemistry* 277(7):5369-5377, 2002.
Brightman et al., "4. Computer Simulation of Signal Transduction," *Computer Simulation of EGF Signal Transduction*, 6 pp.
Burkhardt, "Research Summary—The Role of the Cytoskeleton in T Cell Function," 3pp., Oct. 10 2002.
Burstein et al., "Preoperative Therapy with Trastuzumab and Paclitaxel Followed by Sequential Adjuvant Doxorubicin/Cyclophosphamide for HER2 Overexpressing Stage II or III Breast Cancer: A Pilot Study," *J Clin. Oneal.* 21(1):46-53, Jan. 1, 2003 (abstract only).
Burtscher et al., "The IGF/IGF-1 Receptor Signaling Pathway as a Potential Target for Cancer Therapy,"*Drug Resistance Updates* 2:3-8, 1999.
Busse et al., "Tyrosine Kinase Inhibitors: Rationale, Mechanisms of Action, and Implications for Drug Resistance," *Semin. Oncol.* 28(5 Suppl 16):47-55, Oct. 2001 (abstract only).
Chen et al., "A Fibrous-Bed Bioreactor for Continuous Production of Developmental Endothelial Locus-1 by Osteosarcoma Cells," *J Biotechnol.* 97(1):23-39, Jul. 17, 2002 (abstract only).
Chen et al., "The Angiogenic Factors Cyr61 and Connective Tissue Growth Factor Induce Adhesive Signaling in Primary Human Skin Fibroblasts," *The Journal of Biological Chemistry* 276(13):10443-10452, 2001.
Chen et al., "The Recruitment ofFas-Associated Death Domain/Caspase-8 in Ras-Induced Apoptosis," *Cell Growth & Differentiation* 12:297-306, Jun. 2001.
Chen et al., "Stimulus-Specific Requirements for MAP3 Kinases in Activating the JNK Pathway," *The Journal of Biological Chemistry* 277(51):49105-49110, 2002.
Cross et al., "Quinone Reductase Inhibitors Block SAPK/JNK and NFid3 Pathways and Potentiate Apoptosis," *The Journal of Biological Chemisse* 274(44):31150-31154.
Damelin et al., "In Situ Analysis of Spatial Relationships Between Proteins of the Nuclear Pore Complex," *Biophys. I*83(6):3626-3636, Dec. 2002 (abstract only).
De Miguel et al., "Dissection of the c-Kit Signaling Pathway in Mouse Primordial Germ Cells by Retroviral-Mediated Gene Transfer," *PNAS* 99(16):10458-10463, Aug. 6, 2002.
Dierick et al., "Cellular Mechanisms ofWingless/Wnt Signal Transduction," *Curr. Top. Dev. Biol.* 43:153-190, 1999 (abstract only).
Dinger et al., "Homodimerization ofNeuropeptide Y Receptors Investigated by Fluorescence Resonance Energy Transfer in Living Cells," *J Biol. Chem.*, Jan. 2003 (abstract only).
Du et al., "Multiple Signaling Pathways Direct the Initiation of Tyrosine Hydroxylase Gene Expression in Cultured Brain Neurons," *Brain Res. Mol. Brain Res.* 50(1-2):1-8, Oct. 15, 1997 (abstract only).
Eickhoff et al., "Protein Array Technology: The Tool to Bridge Genomics and Proteomics"*Adv. Biochem. Em!. Biotechnol.* 77:103-112 2002 (abstract only).
English et al., "Pharmacological Inhibitors ofMAPK Pathways," *TRENDS in Pharm. Sciences* 23(1):40-45. Jan. 2002.
Ethier, "Signal Transduction Pathways: The Molecular Basis for Targeted Therapies," *Semin. Radiat. Oncol.* 12(3 Suppl. 2):3-10,Jul. 2002 (abstract only).
Fang et al., "G-Protein-Coupled Receptor Microarrays," *Chembiochem.* 3(10):987-991, Oct. 4, 2002 (abstract only).
Feng et al., "The c-Kit Receptor and its Possible Signaling Transduction Pathway in Mouse Spermatozoa," *Mol. Reprod. Dev.* 49(3):317-326, Mar. 1998 (abstract.

(56) References Cited

OTHER PUBLICATIONS

Fischer-Colbrie et al., "Transsynaptic Regulation of Galanin, Neurotensin, and Substance P in the Adrenal Medulla: Combinatorial Control by Second-Messenger Signaling Pathways," *J Neurochem.* 59(2):780-783, Aug. 1992 (abstract only).
Frost et al., "Cross-Cascade Activation of ERKs and Ternary Complex Factors by Rho Family Proteins," *The EMBO Journal* 16(21):6426-6438, 1997.
Fujita et al., "Overexpression of Mutant Ras in Human Melanoma Increases Invasiveness, Proliferation and Anchorage-Independent Growth in vitro and Induces Tumour Formation and Cachexia in vivo," *Melanoma Res.* 9(3):279-291, Jun. 1999 (abstract only).
Gaits et al., "Shedding Light on Cell Signaling: Interpretation of FRET Biosensors," *Sci. STKE* 2003, pe3, 5 pp., 2003.
Gallagher et al., "Binding of JNK/SAPK to MEKK1 Is Regulated by Phosphorylation," *The Journal of Biological Chemistry* 277(48):45785-45792, 2002.
Ge, "UPA, a Universal Protein Array System for Quantitative Detection of Protein-Protein, Protein-DNA, Protein-RNA and Protein-Ligand Interactions," *Nucleic Acids Research* 28(2):i-vii, 2000.
Geffen et al., "New Drugs for the Treatment of Cancer, 1990-2001," *Isr. Med Assoc. J* 4(12):1124-1131, Dec. 2002 (abstract only).
Ghosh et al., "Rational Design of Potent and Selective EGFR Tyrosine Kinase Inhibitors as Anticancer Agents," *Curr. Cancer Drug Targets* 1(2):129-140, Aug. 2001 (abstract only).
Golemis et al., "Signal Transduction Driving Technology Driving Signal Transduction: Factors in the Design of Targeted Therapies," *Journal of Cellular Biochemistry Supplement* 37:42-52, 2001.
Goodwin et al., "Three-Dimensional Culture of a Mixed Mullerian Tumor of the Ovary: Expression of in vivo Characteristics," *In Vitro Cell Dev. Biol. Anim.* 33(5):366-374, May 1997 (abstract only).
Goss et al., "Aromatase Inhibitors for Chemoprevention," *Best Pract. Res. Clin. Endocrinol Metab.* 18(1):113-130, Mar. 2004 (abstract only).
Gough, "Signal Transduction Pathways as Targets for Therapeutics," *Sci. STKE* 2001(7()):PE1 Apr. 3, 2001 (abstract only).
Gramer et al., "Effect of Harvesting Protocol on Performance of a Hollow Fiber Bioreactor" *Biotechnology and Bioengineering* 65(3):334-340. Nov. 5, 1999.
Gray et al., "Nonradioactive Methods for the Assay of Phosphoinositide 3-Kinases and Phosphoinositide Phosphatases and Selective Detection of Signaling Lipids in Cell and Tissue Extracts," *Anal. Biochem.* 313(2):234-245, Feb. 15, 2003 (abstract only).
Guibinga et al., "Combinatorial Blockade of Calcineurin and CD28 Signaling Facilitates Primary and Secondary Therapeutic Gene Transfer by Adenovirus Vectors in Dystrophic (mdx) Mouse Muscles," *Journal of Virology* 72(6):4601-4609, Jun. 1998.
Gutkind, "Regulation of Mitogen-Activated Protein Kinase Signaling Networks by G Protein-Coupled Receptors," *Sci. STKE* 2000(40):RE1,Jul. 11, 2000 (abstract only).
Haab, "Advances in Protein Microarray Technology for Protein Expression and Interaction Profiling," *Curr. Opin. Drug Discov. Devel.* 4(1):116-123, Jan. 2001 (abstract only).
Harkin, "Uncovering Functionally Relevant Signaling Pathways Using Microarray-Based Expression Profiling," *The Oncologist* 5:501-507, 2000.
Haugh, "A Unified Model for Signal Transduction Reactions in Cellular Membranes," *Biovhvsical Journal* 82(2):591-604 Feb. 2002.
Haugh et al., "Mathematical Modeling of Epidermal Growth Factor Receptor Signaling Through the Phospholipase C Pathway: Mechanistic Insights and Predictions for Molecular Interventions," *Biotechnol. Bioeng.* 70(2):225-238, Oct. 20, 2000 (abstract only).
Heinrich et al., "Mathematical Models of Protein Kinase Signal Transduction," *Molecular Cell* 9:957-970, May 2002.
Heldin, "Signal Transduction: Multiple Pathways, Multiple Options for Therapy," *Stem Cells* 19:295-303, 2001.
Hermanto et al., "Inhibition of Mitogen-Activated Protein Kinase Kinase Selectively Inhibits Cell Proliferation in Human Breast Cancer Cells Displaying Enhanced Insulin-Like Growth Factor !—Mediated Mitogen-Activated Protein Kinase Activation," *Cell Growth & Differentiation* 11:655-664, Dec. 2000.
Houseman et al., "Towards Quantitative Assays with Peptide Chips: A Surface Engineering Approach," *Trends Biotechnol.* 20(7):279-281, Jul. 2002 (abstract only).
Hu et al., "Prolonged Activation ofthe Mitogen-Activated Protein Kinase Pathway Is Required for Macrophage-Like Differentiation of a Human Myeloid Leukemic Cell Line," *Cell Growth & Differentiation* 11:191-200, Apr. 2000.
Huang et al., "High-Throughput Genomic and Proteomic Analysis Using Microarray Technology," *Clinical Chemistry* 47(10):1912-1916, 2001.
Huang, "Detection ofMultiple Proteins in an Antibody-Based Protein Microarray System," *J Immunol. Methods* 255(1-2):1-13, Sep. 1, 2001 (abstract only).
Igarashi et al., "Development of a Cell Signaling Networks Database," 1 1 pp.
Isshiki et al., "A Molecular Sensor Detects Signal Transduction from Caveolae in Living Cells," *The Journal of Biological Chemistry* 277(45):43389-43398, 2002.
Jain et al, "Statistical Pattern Recognition: A Review," *IEEE Transactions on Pattern Analysis and Machine Intelligence* 22(1):4-37, Jan. 2000.
Jessup et al, "Prospects for Use of Microgravity-Based Bioreactors to Study Three-Dimensional Host-Tumor Interactions in Human Neoplasia," *J Cell. Biochem.* 51(3):290 300, Mar. 1993 (abstract only).
Katz et al, "Cellular and Molecular Mechanisms of Carcinogenesis," *Gastroenterol. Clin. North Am.* 31(2):379-394, Jun. 2002 (abstract only).
Katz et al, "Proliferative Signaling and Disease Progression in Heart Failure," *Circ.J* 66:225-231, 2002.
Kawada et al, "Massive Culture of Human Liver Cancer Cells in a Newly Developed Radial Flow Bioreactor System: Ultrafine Structure of Functionally Enhanced Hepatocarcinoma Cell Lines," *In Vitro Cell Dev. Biol. Anim.* 34(2):109-115, Feb. 1998 (abstract only).
Kholodenko et al, "Untangling the Wires: A Strategy to Trace Functional Interactions in Signaling and Gene Networks," *PNAS* 99(20):12841-12846, Oct. 1, 2002.
Kiley et al, "Protein Kinase C 8 Involvement in Mammary Tumor Cell Metastasis," *Cancer Research* 59:3230-3238 Jul. 1, 1999.
Kim et al, "Radicicol Suppresses Transformation and Restores Tropomyosin-2 Expression in Both ras- and MEK-Transformed Cells Without Inhibiting the Raf/MEK/ERK Signaling Cascade," *Cell Growth & Differentiation* 12:543-550, Nov. 2001.
Kurokawa et al, "A Pair of Fluorescent Resonance Energy Transfer-Based Probes for Tyrosine Phosphorylation of the CrkII Adaptor Protein in Vivo," *The Journal of Biological Chemistry* 276(33):31305-31310, 2001.
Larijani et al, "EGF Regulation of PITP Dynamics Is Blocked by Inhibitors of Phospholipase C and of the Ras-MAP Kinase Pathway," *Curr. Biol.* 13(1):78-84, Jan. 8, 2003 (abstract only).
Lev et al, "A Specific Combination of Substrates is Involved in Signal Transduction by the Kit-Encoded Receptor" *EMBO J* 10(3):647-654, Mar. 1991 (abstract only).
Levi et al, "Reversible Fast-Dimerization of Bovine Serum Albumin Detected by Fluorescence Resonance Energy Transfer," *Biochim. Biophys. Acta.* 1599(1-2):141-148, Sep. 23, 2002 (abstract only).
Levitzki, "Signal-Transduction Therapy_A Novel Approach to Disease Management," *Eur. J Biochem.* 226(1):1-13. Nov. 15, 1994 (abstract only).
Licato et al., "A Novel Preclinical Model of Human Malignant Melanoma Utilizing Bioreactor Rotating-Wall Vessels," *In Vitro Cell Dev. Biol. Anim.* 37(3):121-126, Mar. 2001 (abstract only).
Liotta et al., "Clinical Proteomics—Personalized Molecular Medicine," *JAMA* 286(18):2211-2214, Nov. 14. 2001.
Liu et al., "Inhibitory Effect and its Kinetic Analysis of Tyrphostin AG 1478 on Recombinant Human Protein Kinase CK2 Holoenzyme," *Acta. Pharmacal. Sin.* 23(6):556-561, Jun. 2002 (abstract only).

(56) References Cited

OTHER PUBLICATIONS

Lobenhofer et al., "Inhibition of Mitogen-Activated Protein Kinase Phosphatidylinositol 3-Kinase Activity in MCF-7 Cells Prevents Estrogen-Mitogenesis" *Cell Growth & Differentiation* 11:99-110, Feb. 2000.

Lok, "Software for Signaling Networks, Electronic and Cellular," *Sci. STKE* 2002(122):PE11 Mar. 5. 2002 (abstract only).

Lopez et al., "A Model-Based Approach for Assessing in vivo Combination Therapy Interactions," PNAS96(23):13023-13028, Nov. 9, 1999.

Malek et al., "Mechanism of Endothelial Cell Shape Change and Cytoskeletal Remo Response to Fluid Shear Stress," *Journal of Cell Science* 109:713-726, 1996.

Malone et al., "Characterization of Human Tumor-Infiltrating Lymphocytes Expanded in Hollow-Fiber Bioreactors for Immunotherapy of Cancer," *Cancer Biother. Radiopharm.* 16(5):381-390, Oct. 2001 (abstract only).

Marcello et al., "Visualization of in Vivo Direct Interaction Between HIV-1 TAT and Human Cyclin T1 in Specific Subcellular Compartments by Fluorescence Resonance Energy Transfer," *The Journal of Biological Chemistry* 276(42):39220-39225, 2001.

Marinissen et al., "G-Protein-Coupled Receptors and Signaling Networks: Emerging Paradigms," *Trends Pharmacal. Sci.* 22(7):368-376, Jul. 2001 (abstract only).

McVey et al., "Monitoring Receptor Oligomerization Using Time-Resolved Fluorescence Resonance Energy Transfer and Bioluminescence Resonance Energy Transfer," *The Journal of Biological Chemistry* 276(17):14092-14099, 2001.

Mihich et al., "Twelfth Annual Pezcoller Symposium: Signaling Cross-Talks in Cancer Cells," *Cancer Research* 60:7177-7183, Dec. 15, 2000.

Mills et al., "Linking Molecular Therapeutics to Molecular Diagnostics: Inhibition of the FRAP/RAFT/TOR Component of the P13K Pathway Preferentially Blocks PTEN Mutant Cells in Vitro and in Vivo," *PNAS* 98(18):10031-10033, Aug. 28, 2001.

Mirza et al., "Oncogenic Transformation of Cells by a Conditionally Active Form of the Protein Kinase Akt/PKB," *Cell Growth & Differentiation* 11:279-292, Jun. 2000.

Morozov et al., "Direct Detection of Isotopically Labeled Metabolites Bound to a Protein Microarray Using a Charge-Coupled Device," *J Biochem. Biophys. Methods* 51(1):57-67, Mar. 4, 2002 (abstract only).

Nabi et al., "Autocrine Motility Factor and its Receptor: Role in Cell Locomotion and Metastasis," *Cancer Metastasis Rev.* 11(1):5-20, Mar. 1992 (abstract only).

Noll et al., "A Cell-Culture Reactor for the On-Line Evaluation of Radiopharmaceuticals: Evaluation of the Lumped Constant of FDG in Human Glioma Cells," *J NucLMed.* 41(3):556-564, Mar. 2000 (abstract only).

Oshikawa et al., "Synergistic Inhibition of Tumor Growth in a Murine Mammary Adenocarcinoma Model by Combinational Gene Therapy Using IL-12, Pro-IL-18, and IL-113 Convertins Enzyme c DNA" PNAS96(23):13351-13356. Nov. 9, 1999.

Palomer et al., "Identification of Novel Cyclooxygenase-2 Selective Inhibitors Using Pharmacophore Models," *J Med. Chem.* 45(7):1402-1411, Mar. 28, 2002 (abstract only).

Papineni et al., "Suramin Interacts with the Calmodulin Binding Site on the Ryanodine Receptor, RYR1," *The Journal of Biological Chemistry* 277(51):49167-49174, 2002.

Park et al., "Involvement of p38 Kinase in Hydroxyurea-Induced Differentiation of K562 Cells," *Cell Growth & Differentiation* 12:481-486, Sep. 2001.

Paweletz et al., "Reverse Phase Protein Microarrays Which Capture Disease Progression Show Activation of Pro-Survival Pathways at the Cancer Invasion Front," *Oncogene* 20:1981-1989,2001.

Pawlak et al., "Zeptosens' Protein Microarrays: A Novel High Performance Microarray Platform for Low Abundance Protein Analysis," *Proteomics* 2(4):383-393, Apr. 2002 (abstract only).

Petricoin et al., "Clinical Proteomics: Translating Benchside Promise Into Bedside Reality." *Nature Reviews/Drug Discovery* 1:683-695. Sep. 2002.

Price et al., "Role of Vascular Endothelial Growth Factor in the Stimulation of Cellular Invasion and Signaling of Breast Cancer Cells," *Cell Growth & Differentiation* 12:129 135, Mar. 2001.

Raymond et al., "Epidermal Growth Factor Receptor Tyrosine Kinase as a Target for Anticancer Therapy," *Drugs 2000* 60 Suppl. 1:15-23; discussion 41-2, 2000 (abstract only).

Reiners et al., "PD98059 is an Equipotent Antagonist of the Aryl Hydrocarbon Receptor and Inhibitor of Mitogen-Activated Protein Kinase Kinase," *MoL Pharmacal.* 53(3):438 445, Mar. 1998 (abstract only).

Robinson et al., "Different Domains of the Mitogen-Activated Protein Kinases ERK3 and ERK2 Direct Subcellular Localization and Upstream Specificity in Vivo," *The Journal of Biological Chemistry* 277(7):5094-5100, 2002.

Rocha et al., "Protein Kinase C Inhibitor and Irradiation-Induced Apoptosis: Relevance of the Cytochrome c-Mediated Caspase-9 Death Pathway," *Cell Growth & Differentiation* 11:491-499, Sep. 2000.

Schoeberl et al., "Computational Modeling of the Dynamics of the MAP Kinase Cascade Activated by Surface and Internalized EGF Receptors," *Nature Biotechnology* 20:370 375 Apr. 2002.

Schwab et al., "Modeling Signal Transduction in Normal and Cancer Cells Using Complex Adaptive Systems," *Med. Hypotheses* 48(2):111-123, Feb. 1997 (abstract only).

Sedaghat et al., "A Mathematical Model of Metabolic Insulin Signaling Pathways," *Am. I Physiol. Endocrinol. Metab.* 283 (5): E1084-E1101, Nov. 2002 (abstract only).

Seong, "Microimmunoassay Using a Protein Chip: Optimizing Conditions for Protein Immobilization," *Clinical and Diagnostic Laboratory Immunology* 9(4):927-930, Jul. 2002.

Smith et al., "Signaling Complexes: Junctions on the Intracellular Information Super Highway," *Curr. Biol.* 12(1):R32-R40, Jan. 8, 2002 (abstract only).

Sreekumar et al., "Profiling of Cancer Cells Using Protein Microarrays: Discovery of Novel Radiation-Regulated Proteins," *Cancer Research* 61:7585-7593, Oct. 15, 2001.

Staib et al., "TP53 and Liver Carcinogenesis," *Hum. Mutat.* 21(3):201-216, Mar. 2003 (abstract only).

Stoll et al., "Protein Microarray Technology," *Front. Biosci.* 7:c13-c32, Jan. 1, 2002 (abstract only).

Strnad et al., "Induction of Rapid and Reversible Cytokeratin Filament Network Remodeling by Inhibition of Tyrosine Phosphatases," *Journal of Cell Science* 115:4133 4148, Aug. 7, 2002.

Stultz et al., "Phosphorylation-Induced Conformational Changes in a Mitogen-Activated Protein Kinase Substrate," *The Journal of Biological Chemistry* 277(49):47653-47661, 2002.

Su et al., "A Combinatorial Approach for Selectively Inducing Programmed Cell Death in Human Pancreatic Cancer Cells," *PNAS* 98(18):10332-10337, Aug. 28, 2001.

Taipale et al., "The Hedgehog and Wnt Signalling Pathways in Cancer," *Nature* 411(6835):349-354. May 17, 2001 (abstract only).

Templin et al., "Protein Microarray Technology," *Trends Biotechnol.* 20(4):160-166, Apr. 2002 (abstract only.

Tenzer et al., "The Phosphatidylinositide 3'-Kinsae/Akt Survival Pathway Is a Target for the Anticancer and Radiosensitizing Agent PKC412, an Inhibitor of Protein Kinase C," *Cancer Research* 61:8203-8210, Nov. 15, 2001.

Torrance et al., "Combinatorial Chemoprevention of Intestinal Neoplasia," *Nature Medicine* 6(8):1024-1028, Sep. 2000.

Tortora et al., "Protein Kinase A as Target for Novel Integrated Strategies of Cancer Therapy," *Ann. NY Acad. Sci.* 968:139-147,2002.

Varshaysky, "Codominant Interference, Antieffectors, and Multitarget Drugs," *Proc. Nat!. Acad. Sci. USA* 95:2094-2099, Mar. 1998.

Vogt et al., "A Random Walk in Oncogene Space: The Quest for Targets," *Cell Growth & Differentiation* 10:777-784, Dec. 1999.

(56) References Cited

OTHER PUBLICATIONS

Wall et al., "Mitogen-Activated Protein Kinase Is Required for Bryostatin 1-Induced Differentiation of the Human Acute Lymphoblastic Leukemia Cell Line Rch," *Cell Growth & Differentiation* 12:641-647, Dec. 2001.

Wang et al., "The p38 Mitogen-Activated Protein Kinase Mediates Cytoskeletal Remodeling in Pulmonary Microvascular Endothelial Cells Upon Intracellular Adhesion Molecule-1 Ligation," *The Journal of Immunology*, pp. 6877-6884, 2001.

Weng et al., "Generating Addressable Protein Microarrays With Profusion Covalent mRNA-Protein Fusion Technology," *Proteomics* 2(1):48-57, Jan. 2002 (abstract only).

Whitacre et al., "Adrogen Induction of in Vitro Prostate Cell Differentiation," *Cell Growth & Differentiation* 13·1-11 Jan. 2002.

Whitehurst et al., "ERK2 Enters the Nucleus by a Carrier-Independent Mechanism," *PNAS* 99(11):7496-7501, May 28, 2002.

Wiese, "Analysis of Several Fluorescent Detector Molecules for Protein Microarray Use," *Luminescence* 18(1):25-30 Jan.-Feb. 2003 (abstract only).

Winters et al., "Combination of a Selective Cyclooxygenase-2 Inhibitor and a Calcium Channel Blocker Causes a Cooperative Anticancer Effect," National Cancer Institute, FDA-NCI Clinical Proteomics Program, Howard Hughes Medical Institute, and Food and Drug Administration, 26 pp.

Wong et al., "Molecular Topography Imaging by Intermembrane Fluorescence Resonance Energy Transfer," *Proc. Nat. Acad. Sci. USA* 99(22):14147-14152, Oct. 29, 2002 (abstract only).

Xu et al., "The Inducible Expression of the Tumor Suppressor Gene PTEN Promotes Apoptosis and Decreases Cell Size by Inhibiting the P13KJAkt Pathway in Jurkat T Cells." *Cell Growth & Differentiation* 13:285-296. Jul. 2002.

Yarden, "The EGFR Family and its Ligands in Human Cancer: Signalling Mechanisms and Therapeutic Opportunities," *European Journal of Cancer* 37:S3-S8, 2001.

Yarden et al., "Untangling the ErbB Signalling Network," *Nat. Rev. Mol Cell. Biol.* 2(2):127-137, Feb. 2001 (abstract only).

Zhu et al., "Protein Arrays and Microarrays," *Curr. Opin. Chem. Biol.* 5(1):40-45, Feb. 2001 (abstract only).

\* cited by examiner

|        | PATIENT 1 | PATIENT 2 | PATIENT 3 | PATIENT 4 |
|--------|-----------|-----------|-----------|-----------|
| pSTAT1 | ◉ · | ◉ · | ● ○ · | ● |
| pERB2  | ● · |   |   |   |
| pER    | ○ ○ | ◉ ○ | ○ | ○ |
| pAKT   | ● ◉ · | · · | ● ○ |   |
| pGSK3b | ● · · | · · | ● · · | · |
| pFKHRL | ● · · |   | ◉ ○ · | · · · · |

*FIG. 19*

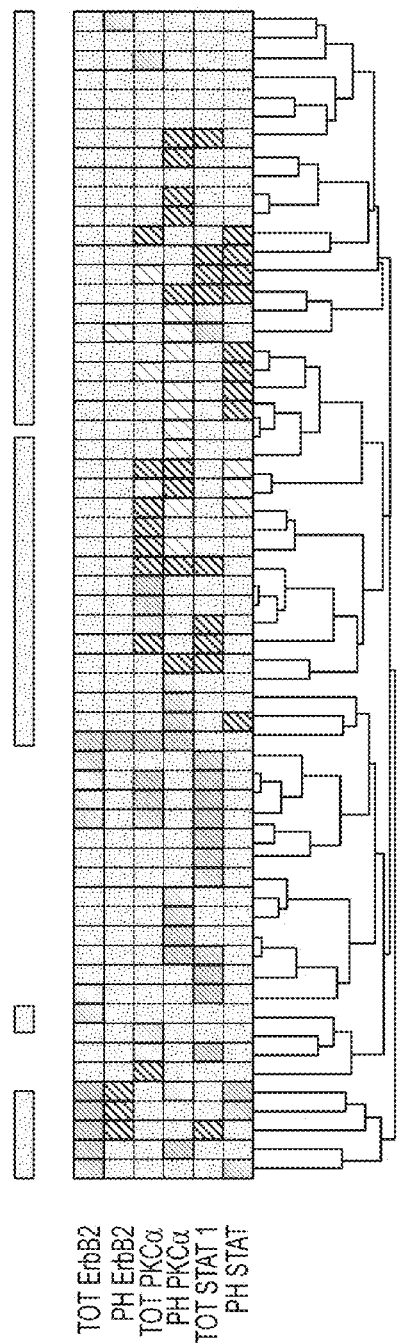
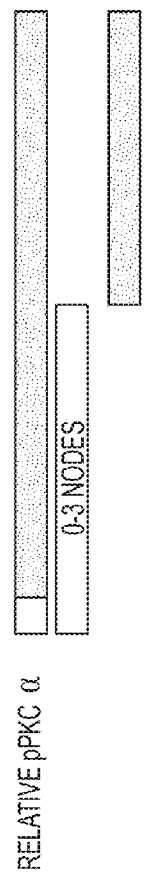
FIG. 21A
FIG. 21B

COMBINATORIAL THERAPY FOR PROTEIN SIGNALING DISEASES

CROSS REFERENCE TO RELATED APPLICATION

This application is a continuation application of, and claims the benefit of and priority to, U.S. patent application Ser. No. 12/581,019, filed Oct. 16, 2009, which issued as U.S. Pat. No. 8,168,568 B1 on May 1, 2012. U.S. patent application Ser. No. 12/581,019, filed Oct. 16, 2009, is a continuation application of, and claims the benefit of and priority to, abandoned U.S. patent application Ser. No. 10/798,799, filed Mar. 10, 2004, now abandoned which claims the benefit of and priority to U.S. Provisional Patent Application No. 60/453,629, filed Mar. 10, 2003. All such applications are expressly incorporated herein by reference in their entireties.

FIELD

The disclosed methods relate to design and selection of combinations of therapeutic agents that may be utilized to treat diseases arising from aberrant signaling pathways. More particularly, the disclosure relates to identifying therapeutic combinations that specifically target the signal pathway aberrations leading to disease in a particular individual.

BACKGROUND

In cancer and other diseases such as Alzheimer's disease and inflammatory diseases, the signal transduction pathways within cells are often observed to be hyperactive and dominant or hypoactive. For example, defective, hyperactive or dominating signal pathways appear to drive cancer growth, survival, invasion and metastasis (Liotta and Kohn, "The microenvironment of the tumor-host interface," Nature 411: 375-379, 2001). The hyperactive pathway observations do not necessarily indicate the presence of greater amounts of protein or mRNA, but rather are a consequence of altered activation states of pathway components, and from altered interactions (cross-talk) between pathways that are separated in normal cells, but linked in tumor cells. Recognizing that signaling pathways may be targeted for therapy, pharmaceutical companies are developing specific inhibitors of pathway components such as tyrosine kinases. Unfortunately, efficacious doses of these drugs are often so high that they result in non-specific binding to molecules outside of the targeted pathway, and thus toxicity. Furthermore, diseased cells are often observed to develop resistance to the agents due to shunting around targeted pathway components and/or development of alternative signaling pathways.

SUMMARY

The activation state of kinase driven signal networks contains important information about the signals that drive disease specific biological processes and is useful for therapeutic target selection. A method is disclosed for mapping the activity states of proteins in signaling networks to discover coordinated signal transduction events that can be targeted with combinations of therapeutic agents. An example of a signaling network is a combination of signaling pathways that interact. Based on the observed activity states of the signaling proteins in a network, combinations of therapeutic agents are selected to specifically alter the activity state of two or more interconnected signaling proteins, for example within different signaling pathways of the network. Choosing combinations of agents in this manner is shown to reduce shunting around targeted proteins in the signaling network and provide surprising synergistic effects that permit treatment of signaling abnormalities with lower doses of potentially toxic agents.

Since normal and diseased cells can be compared for a particular individual, the disclosed method can be used to select combinations of therapeutic agents that are tailored to the particular signaling abnormalities observed a disease state (such as a particular tumor type) or even in a particular individual. Repeated assessment of the activity states of diseased cells following treatment with a selected combination of agents also can detect development of resistance to the treatment and be used to identify new, different combinations of therapeutic agents that target the developing resistance mechanism (such as induction of an alternative signaling pathway).

BRIEF DESCRIPTION OF THE DRAWINGS

FIG. 19 is photograph of a reverse phase protein microarray kinase substrate analysis used to detect concordance of AKT-mediated signaling.

FIG. 21A shows a heat map of the results of principal component analysis of protein kinase microarray analysis of normal and breast cancer subjects and a heat map analysis showing a correlation in FIG. 21B between the relative levels of phosphorylated PKCα obtained from surgical specimens of 17 subjects post A/C therapy with lymph node involvement.

DETAILED DESCRIPTION OF SEVERAL DISCLOSED EMBODIMENTS

I. Abbreviations

Figure 1A:
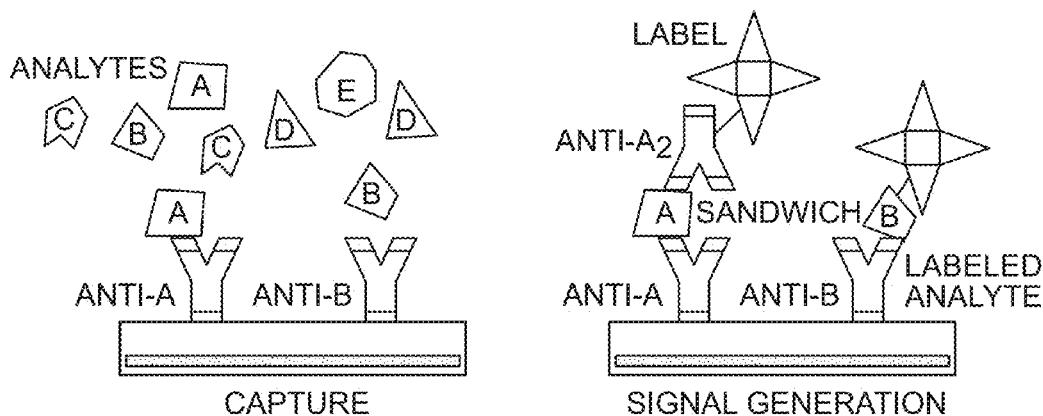
FIG. 1A and FIG. 1B are diagrams showing two classes of protein microarray platforms.

LCM—laser capture microdissection
FACS—fluorescence-activated cell sorting
MALDI-TOF—matrix-assisted laser desorption/ionization time-of-flight mass spectrometry
SELDI-TOF—surface-enhanced laser desorption/ionization time-of-flight mass spectrometry
HPLC—high performance liquid chromatography
NMR—nuclear magnetic resonance
MRI—magnetic resonance imaging
FRET—fluorescence resonance energy transfer
FPA—forward phase array
RPA—reverse phase array
EGFR—epidermal growth factor receptor
EGF—epidermal growth factor
CAI—carboxyamidotriazole
NVGCC—non-voltage gated calcium channel.

II. Terms

The singular forms "a," "an," and "the" refer to one or more, unless the context clearly indicates otherwise.

"Comprises" means including. Hence "comprising A or B" means including A or B, or including A and B, unless the context clearly indicates otherwise.

The term "subject" refers to any animal, including humans, other primates and veterinary animals such as horses, pigs, goats, cattle, dogs, cats and sheep.

As used herein, the term "activity state" refers to an identifiable signaling event that occurs at a node (signaling protein) along a protein signaling pathway or network as a signal or signals is (are) passed along the pathway or within the network. The activity state of a particular signaling protein can change over time or can reach an equilibrium state when the passage of a certain level of signal passing through the pathway or network is maintained for a sufficient period of time. Examples of an activity state include the level of post-translational modification of a signaling protein such as the level of phosphorylation or farnesylation of a signaling protein or the cleavage state of a signaling protein, the cellular location of a signaling protein, or the level of association of a signaling protein with another protein.

The term "signaling pathway" refers to an identifiable signal cascade through which a signal flows. In particular, a signaling pathway is a series of cellular proteins (such as a cell surface receptor, an intracellular signaling protein, or both) along which a signal flows in response to a stimulus, such as an extracellular or intracellular stimulus that interacts with a cell at a cell surface receptor. The terms "signaling pathway" and "signal transduction pathway" are intended to indicate the coordinated intracellular processes whereby a living cell transduces an external or internal signal into cellular responses. Signal transduction may, for example, involve an enzymatic reaction and enzymes mediating such enzymatic reactions include, but are not limited to, protein kinases, GTPases, ATPases, protein phosphatases, and phospholipases. The cellular responses that are controlled by signaling pathways include, but are not limited to, gene transcription, secretion, proliferation, mechanical activity, metabolic activity, and cell death. A signaling pathway can carry a signal from the plasma membrane to the nucleus in response to an extracellular stimulus, or can carry a signal from one part of a cell to another, for example, where two or more intracellular signaling pathways interact. Thus, a signal generated in a particular signaling pathway by an extracellular stimulus can flow into other signaling pathways within the cell. In some instances, the signal is mediated by a series of post-translational modifications of the proteins in the pathway such as in protein kinase signaling cascades where, for example, one kinase phophorylates another kinase that in turn phophorylates another kinase. In other instances, the signal is mediated by protein translocations or protein-protein interactions. For example, post-translational modification of one protein in a signaling pathway can lead to translocation of the protein to another part of the cell, where the translocated protein then post-translationally modifies yet another protein to pass the signal along the pathway. Alternatively, a post-translational modification of a particular protein can promote its association with another protein to form a dimer, and then the dimer post-tranlationally modifies yet another protein to pass the signal along the pathway. Examples of signaling pathways include the integrin pathway, the focal adhesion signaling pathway, the Akt signaling pathway, the IL-6R pathway, growth factor pathways, chemokine receptor signal pathways, cell-cycle signaling pathways, stress signal pathways, apotosis signaling pathways, Tau/beta signaling pathways, pro-inflammatory pathways, differentiation signaling pathways, T-cell receptor pathways, death-receptor signaling pathways, survival signaling pathways, MAPK signaling pathways, p38 MAPK signaling pathways, G-coupled Receptor signaling pathways, SAPK/JNK signaling pathways, insulin receptor signaling pathways, Wnt signaling pathways, B-cell antigen signaling pathways, cKit signaling pathways, and Jak/Stat signaling pathways. These and other signaling pathways may be intermediately interconnected to each other by interactions that lead to cross-talk between the pathways to form a signaling network. Interconnections between pathways may be mediated by, for example, for example, protein-protein interactions, post-translational modifications, protein cleavage, translocations to an organelle or compartment, ion channel activation, soluble mediators, protein-nucleic acid interactions, protein-lipid interactions, or protein-carbohydrate interactions can pass signals from one signaling pathway to another.

As used herein, the term "protein signaling network" refers collectively to all the signaling proteins that are interconnected to a particular signaling protein by at least a common cellular response. Examples of cellular responses that can connect signaling pathways to form a signaling network include cell growth, cell death (apoptosis), cytoskeletal remodeling, cell survival, receptor localization and distribution, gene transcription, motility, differentiation, proliferation, or angiogenesis. In other instances, signaling pathways are connected to form a signaling network by virtue of their having one or more signaling proteins in common, or by virtue of a first signaling protein in one pathway passing a signal to a second signaling protein in a different pathway such as by post-translational modification of the second protein by the first. "Cross-talk" refers to the situation where a signal following one pathway is transferred to another pathway.

A "diseased cell" is a cell that is identifiable (for example histologically or immunologically) as being involved in a pathological condition of a tissue. For example, a diseased cell can be a cell that exhibits an appearance (with or without staining) that is different from normal cells of the same type. For example, a tumor cell may have pyknotic nuclei and abnormal appearing cellular organelles, and be in an area of cellular invasion. A diseased cell also can be a cell that expresses a particular molecule (such as a receptor or other cell surface marker) on its surface that is not present on the surfaces of cells of the same type that are not involved in the pathological condition, and, for example, may be identified by binding of a labeled antibody against the particular molecule expressed on its surface. Examples of diseased cells include tumor cells such as breast tumor cells, colon tumor cells, prostate cancer cells, and lung cancer cells. Still other examples of diseased cells include brain cells in which amyloid deposits are visible, such as obtained from an Alzheimer's patient.

"COX inhibitor" refers to a compound that diminishes the enzymatic activity of a cyclooxegenase enzyme such as COX-1 and COX-2. A selective COX-2 inhibitor is a compound that diminishes the enzymatic activity of the COX-2 enzyme, but not other COX enzymes such as the COX-1 enzyme.

III. Overview

The following description and examples are provided solely to assist in understanding the disclosure, and not to limit its scope.

In one aspect a new method is provided for selecting a treatment for a diseases characterized by aberrant protein signaling pathways. Examples of such diseases include neurodegenerative diseases and cancer. Diseases with an aberrant signaling component are characterized by signaling pathways that are hyperactive and dominant or hypoactive, leading to an increase or decrease, respectively, of a cellular response that is under the control of the signaling pathway. For example, where cell growth is under the control of a hyperactive signaling pathway, abnormally rapid cell growth will be evident. Similarly, if apoptosis (death) of cells is under the control of a hypoactive signaling pathway, the cells exhibit abnormally decreased apoptosis. Rapid cell growth and decreased apoptosis, alone or in combination, can, for example, lead to tumor proliferation as an ultimate cellular response.

The disclosed method of treating protein signaling diseases is based in part on the discovery that targeting two or more different interdependent steps in a protein signaling pathway (or in a network of pathways leading to a common cellular response or interconnected so there is cross-talk between pathways) with a combination of therapeutic agents that inhibit or stimulate these steps can provide synergistic effects on the cellular response. Kinetic modeling of signal transduction events in a signaling pathway reveals that modulation of two or more different signal transduction events in the pathway generally provides synergistic effects on the final response (such as a cellular response). Therefore, when used in combinations that target multiple different targets (that is multiple different signaling proteins or events) in the pathway, individual agents can be used at much lower doses than would be necessary if the agents were administered alone. Experimental data confirms these surprising results. These unexpected findings also make it possible to optimize a selected combination of therapeutic agents by finding the lowest dose of the agents directed to multiple interdependent targets that provides a desired change in the cellular response of a signaling pathway (or network of pathways). This is contrary to conventional therapy, which attempts to find the highest tolerable dose of an agent or agents directed to a single target. Furthermore, combinations of therapeutic agents that are selected according to the disclosure are shown to help diminish shunting of signals around single targeted signaling proteins (or signaling events).

Synergistic combinations of therapeutic agents are selected according to the disclosure by determining the signaling pathway aberrations that are associated with a particular disease state. Since it is possible to determine signaling aberrations for an individual it is also possible to select combinations of agents to target an individual's particular signaling pathway aberrations.

Signaling pathway aberrations can be determined by measuring an activity state for several different proteins that belong to a protein signaling pathway or network. Belonging to a pathway refers to a protein that receives signals, transmits signals, or both that follow the pathway from an initial stimulus (such as an extracellular stimulus) to a particular cellular response. The activity states of the proteins can be measured in vivo, substantially as they occur in vivo (such as by preserving the in vivo activity state and then extracting the proteins from a sample) or in vitro, such as in a cell culture. The activity state that is measured is the state of a signaling event that occurs along the pathway or network as a signal or signals is (are) passed along the pathway or within the network. The measured activity state can be the presence, absence or extent of a protein-protein interaction, a post-translational modification (e.g. phosphorylation, farnesylation, myristylation acetylation or ubiquitinization), a protein cleavage, a translocation to an organelle or compartment, an ion channel activation, a concentration of a soluble mediator that is a product or a substrate of the protein, a protein-nucleic acid interaction, a protein-lipid interaction, or a protein-carbohydrate interaction that reflects passage of a signal through a signaling protein. Activity states can be measured by immunohistochemical methods such as array techniques (e.g. reverse-phase microarrays) and western blotting, electrophoretically (such as by isoelectric focusing and capillary elecrtrophoresis), chromatographically (such as by HPLC) or instrumentally using techniques such as mass spectrometry (e.g. MALDI-TOF, SELDI), magnetic resonance (e.g. NMR or MRI using antibodies labeled with MR active compounds, such as gadolinium chelates) and fluorescence resonance energy transfer [FRET; see, for example, Gaits and Hahn, "Shedding light on cell signaling:interpretation of FRET biosensors," *Sci STKE* 2003 Jan. 14; 2003 (165):PE3]. In one particularly disclosed example, the activity state is the ratio of the amount of phosphorylated signaling protein to the total amount of the signaling protein. If a method of imaging is employed to determine an activity state, it is possible, for example, to image the phosphorylated state, or other activity state, of at least the treatment targets and nodes along possible shunting pathways. In this way, efficacy may be monitored during treatment, thereby permitting adjustments to the treatment to be made sooner, and more effectively.

One or more agents that stimulate particular pathways or a network of pathways that share a common cellular response also can be used to initiate signal transduction, thereby permitting determination of a time course of signaling events and activity states in the signaling pathway or network. For example, signaling events that are mediated by the epidermal growth factor receptor (EGFR) can be observed over time following treatment of cells with epidermal growth factor (EGF). Thus, signaling aberrations also can be manifested by an altered time-course of the changes in activity states of the signaling proteins in a signaling pathway or network.

A comparison of the observed activity states in diseased cells to those observed for normal cells (from the same or different individual), or a comparison of observed activity states to activity states associated with a particular desired cellular response (such as apoptosis), can be used to select combinations of agents to treat the aberrant signaling pathway or network in the diseased cells. The comparison is used to determine different targets in a pathway or network (such as several hyperphosphorylated proteins in the diseased cells) and how the activity states of the targets should be modulated (such as to alleviate hyperphosphorylation). It is on this basis that therapeutic agents can be selected. In other words, based on the observed activity states of the signaling proteins in an aberrant signaling pathway or network, combinations of therapeutic agents can be selected to specifically alter the activity states of two or more different interconnected signaling proteins in the pathway or network from the observed aberrant activity states toward desired activity states, such as a normal activity states. For example, if a comparison of the activity states of signaling proteins between normal and cancerous cells reveals hyperphosphorylation of a number of proteins in the cancerous cells relative to the normal cells, combinations of agents that alleviate hyperphosphorylation of two or more of the different hyperphosphorylated proteins (such as by inhibiting phosphorylation or stimulating dephosphorylation of the proteins) can be selected. In other instances, hypophosphorylation of certain proteins may be observed in the diseased cells and can be targeted, for example, with agents that stimulate phosphorylation or inhibit dephosphorylation of the hypophosphorylated proteins.

Since the phosphorylation and dephosphorylation events in a signaling pathway or network are interdependent, it is not necessary to modulate the particular signaling event that directly leads to a particular activity state for a particular signaling protein. Rather, upstream or downstream events within the pathway can also be targeted to alter the activity state of a particular protein. For example, inhibiting upstream phosphorylation events also can lead to decreased phosphorylation of a particular signaling protein that is further along a particular signaling pathway, thereby changing the activity state of the particular signaling protein.

In the disclosed method, a sample comprising a diseased cell is obtained from a subject and analyzed to detect aberrant activity states (or time-course thereof) of the signaling proteins that it contains. The sample may be any sample containing diseased cells, but typically is a sample obtained from a lesion, for example, a biopsy sample of a lesion. In some embodiments, the sample is obtained from a tumor or a specific diseased tissue. For example, the sample can be obtained from breast tumors, prostate tumors, brain tumors, colon polyps and tumors, tissue from arthritic joints, and tissue containing amyloid formations obtained from the brains of subjects with Alzheimer's disease.

Desirably, diseased cells can be isolated from the sample to provide a substantially pure population of the diseased cells for analysis of their protein signaling pathways and networks. Isolated diseased cells are desired because they permit more accurate analysis of signaling pathway aberrations that are characteristic of the disease. Diseased cells may be isolated from non-diseased cells in a sample by any means including, for example, microdissection and fluorescence-activated cell sorting (FACS). These methods also can be employed to isolate substantially pure populations of non-diseased reference cells for comparison.

FACS is a specific type of flow cytometry, which utilizes fluorescent markers (fluorescently labeled monoclonal antibodies) placed on the cells for the purpose of recognizing and sorting the cells. FACS instruments typically possess the ability to perform multiparameter analyses on a single cell. Among the many measurable properties are size, volume, viscosity, the content of DNA, RNA, and enzymes, and also surface antigens. FACS instrumentation is available from Beckman-Coulter, Miami, Fla.

Microdissection is a technique where cells or groups of cells are separated from one another, typically while viewing the cells under a microscope. Examples of microdissection techniques include UV laser ablation of unwanted tissue regions (Meirer-Ruge et al., The laser in the Lowry technique for microdissection of freeze-dried tissue slices, *Histochemical J.* 8: 384, 1976) and laser capture microdissection (LCM, see Example 1 below).

Proteins can be extracted from the isolated diseased cells and reference cells, for example, by lysing the cells in an appropriate lysis buffer. Advantageously, the lysis buffer is one designed to retain the proteins in a state that reflects their in vivo characteristics.

In the disclosed methods, the activity state of one or more signaling proteins extracted from the diseased cell are measured and compared to the activity states measured for the corresponding signaling protein(s) extracted from a reference cell, such as a normal cell or a cell isolated either before or after treatment (such as with one or more therapeutic agents), or before or after a disease state or stage. Differences between the activity states observed for the diseased and reference cells are used to detect deranged signaling pathways that are active in the diseased cell.

Once one or more deranged signaling pathways are identified in the diseased cells, a combination of therapeutic agents may be administered to the subject to correct the cell signaling derangement. Specifically, the therapeutic agents are selected to target two or more different members of the protein signaling network comprising the detected deranged signaling pathway. In particular examples, the therapeutic combination is selected to provide a synergistic improvement in efficacy of treatment of the aberrant cellular response mediated by the deranged signaling pathways of the network. As used herein, "synergistic improvement in efficacy" refers to the situation where the combination is more effective for treating the aberrant cellular response than the additive effects of the agents comprising the combination acting alone and at the same dose used in the combination. The synergism exhibited by combinatorial therapy directed to interconnected signaling proteins (nodes) in a protein signaling network is a surprising result of the disclosed methods of selecting and administering treatments.

In another aspect, the disclosed methods may further include dividing and culturing the sample obtained from the subject into a plurality of cultures. This may be done to optimize selected combinations of therapeutic agents for synergistic efficacy in treating the aberrant cellular response, or to detect development of resistance mechanisms. The separate cultures are treated with predetermined combinations of the selected therapeutic agents that target two or more different components of the detected deranged signaling pathway or the interconnected signaling network. Additional cultures also are treated individually with each of the therapeutic agents of the combinations at doses present in the combinations, and synergism can be detected by comparing the combined effect of the individual agents used separately to the effect observed for treatment with the combination. Synergistic combinations are thus identified, and may be administered to the subject for the purpose of treating the aberrant cellular response that is characteristic of the subject's disease. Advantageously, such combinations may provide higher efficacy than single agents administered at much higher doses and therefore provide lower toxicity. To assist in speedy identification of synergistic combinations, the cell cultures may be stimulated to exhibit the aberrant cellular response by adding a signal pathway stimulator or inhibitor to the culture.

Culturing of cells for the purpose of optimizing a treatment or detecting possible resistance mechanisms may be accomplished using a bioreactor such as a hollow-fiber bioreactor, a fibrous bed reactor, a T-flask, a rotating-wall vessel bioreactor, a fluidized-bed cell reactor, a microgravity-based bioreactor, or a gas-permeable bag bioreactor. Hollow-fiber reactors, rotating-wall bioreactors and microgravity based bioreactors offer the potential advantage of recreating the 3D architecture of the cells that is found in vivo, and thus may provide samples of disease cells that are more faithfully representative of the activity states of signaling proteins in diseased tissues. (See for example, Chen et al., *J. Biotechnol.*, 97: 23-39, 2002; Licato et al., *In Vitro Cell Dev Biol Anim*, 37:121-6, 2001; and Goodwin et al., *In Vitro Cell Dev. Biol Anim.*, 33: 366-74, 1997). Hollow-fiber bioreactor services are available for example from Cytomol, San Leandro Calif.

Alternatively, therapeutic combinations may be selected based on prior success in treating the same types of pathway derangements observed and treated in other subjects. Another alternative is to refer to testing done on cultures obtained from other subjects having similar signaling derangements, such as patterns of activity states for several nodes in a signaling pathway or network. Yet another alternative is to refer to testing done on normal cells stimulated with effectors of particular pathways. Thus, not only is it possible to select individualized treatments for particular subjects, it is also possible to develop panels of drug combinations that may be used to treat particular patterns of signal pathway derangements by performing disclosed assays on cultured cells.

The similarity between the signaling derangements (as manifested in patterns of activity states for signaling proteins of one or more signaling pathways or networks) amongst multiple subjects having similar diseases may be detected and measured using pattern recognition methods such as statistical and neural network methods (see, for example, Jain et al., "Statistical Pattern Recognition: A review," *IEEE Transactions on Pattern Analysis and Machine Intelligence,* 22: 4-37, 2000). Pattern recognition may also be used to detect the similarity of a particular subject's signaling derangements to those seen in the diseases of others. Such comparisons may be useful for selecting an appropriate treatment for the subject (that is, a treatment based on success in other subjects with similar derangements). Pattern recognition methods include principal component analysis, genetic algorithms, self-organizing maps, K-means clustering, Baysean-clustering algorithms, feed-forward and back-propagation neural networks, decision trees and combinations thereof. These techniques are also helpful for comparing diseased cells to normal cells for the purpose of identifying deranged signaling pathways. A percent similarity, such as a percent similarity greater than 60%, for example, greater than 70%, 80% or 90%, between derangement patterns may be used to make a decision on whether a treatment successful for treating a derangement and/or aberrant cellular response in one subject may be used to treat another subject exhibiting a similar derangement pattern.

In particular embodiments, the combination of therapeutic agents used to treat a disease characterized by an aberrant cellular response comprises two or more different drugs that separately target EGFr dimerization, EGFr phosphorylation, AKT phosphorylation, non-voltage gated calcium ion channels, cyclooxygenase-1, cyclooxygenase-2, MEK-1, NFKB/IKB, or P38. In more particular embodiments, the combination prevents shunting to or around a signaling pathway. For example, in one disclosed embodiment the combination includes a drug that inhibits MEK phosphorylation of ERK kinase, and shunting occurs via activation and phosphorylation of CREB. In still other particular embodiments, the combination comprises a prostaglandin pathway effector and a non-voltage gated calcium influx channel effector, CaI and a COX-2 inhibitor, an AKT kinase inhibitor in combination with an EGF dimerization inhibitor (e.g. herceptin) or an EGF kinase inhibitor (e.g. IRESSA), or a combination that comprises a PKCα agonist resulting in phosphorylation and activation of PKCα.

In one embodiment, a method is provided for selecting a combination of therapeutic agents for treatment of a disease caused by a deranged cell signaling pathway or cell signaling pathway network that leads to an aberrant cellular response. The method involves measuring the activity states for a plurality of different signaling proteins extracted from a diseased cell, where the signaling proteins are members of one or more signaling pathways or networks and determining whether the activity states measured for the plurality of signaling proteins extracted from the diseased cell are different than activity states measured for corresponding signaling proteins from a reference cell. Detected differences between the activity states of individual signaling proteins from the diseased cell and the activity states of the corresponding individual signaling proteins from the reference cell are used to identify targets for treatment with a combination of at least two different therapeutic agents. The therapeutic agents are selected to target two or more different members of a protein signaling pathway or network that include an individual signaling protein for which a difference in activity state was detected between the diseased cell and the reference cell. The agents are also selected to reduce the difference in the activity state that was detected. In some instances the combination of therapeutic agents provides a synergistic improvement in efficacy of treatment of the aberrant cellular response when compared the combined efficacies of the agents administered alone at the same dose.

Examples of activity states that can be measured include one or more of a protein-protein interaction, a post-translational modification, a protein cleavage, a translocation to an organelle or compartment, an ion channel activation, a concentration of a soluble mediator that is a product or a substrate of the protein, a protein-nucleic acid interaction, a protein-lipid interaction, or a protein-carbohydrate interaction. Examples of post-translational modifications include phosphorylation, farnesylation, myristylation acetylation or ubiquitinization.

In particular embodiments the difference in activity states detected is an increase in the activity state of an individual signaling protein from the diseased cell in comparison to the same signaling protein in the reference cell. In this instance the therapeutic agents are selected to counteract the increase in the activity state of the individual signaling protein from the diseased cell. For example the increase in activity state of the individual signaling protein from the diseased cell can be an increase in phosphorylation. The therapeutic agents are then selected to counteract the increase in phosphorylation of the individual signaling protein from the diseased cell.

In other particular embodiment, the difference in activity states detected is a decrease in the activity state of an individual signaling protein from the diseased cell in comparison to the same signaling protein in the reference cell. In this instance, the therapeutic agents are selected to counteract the decrease in the activity state of the individual signaling protein from the diseased cell. For example, where the decrease in activity state of the individual signaling protein from the diseased cell is a decrease in phosphorylation, the therapeutic agents are selected to counteract the decrease in phosphorylation of the individual signaling protein from the diseased cell.

In other embodiments, the diseased cell is obtained from tissue of a subject and the diseased cell is isolated the diseased cell from the tissue of the subject, for example, by microdissection of the diseased cell from the tissue. In a particular embodiment laser capture microdissection is used. Alternatively, the diseased cell can be isolated by fluorescence activated cell sorting. The plurality of different signaling proteins in a cell sample comprising the diseased cell can also be extracted.

The activity states of the plurality of signaling proteins can be measured by any available method including protein microarray analysis, immunohistochemistry, antibody microarray analysis, or bead capture. In particular embodiments reverse phase protein microarray analysis is used. In more particular embodiments, reverse phase protein microarray analysis is used to detect phosphorylated signaling protein and/or the total amounts of the signaling proteins regardless of their phosphorylation state. If both are measured, the activity state of the signaling protein can be expressed as a ratio of the phosphorylated signaling protein to the total amount of the signaling protein.

The reference cell that is used in the method can be a normal cell (such as a cell with a normal histological appearance), a cell before or after a treatment with a therapeutic agent or an effector of a signaling pathway, or a cell before or after a disease or a stage of disease.

In other particular embodiments, the reference cell and the diseased cell are obtained from the same subject. In others, the reference cell is obtained from one subject and the diseased cell is obtained from another subject. Cells can also be cultured cells raised by stimulating growth and division of a diseased cell or a reference cell.

Examples of aberrant cellular responses that can be treated in a subject using combinations of agents selected according to the disclosed methods include abnormal growth, apoptosis, cytoskeletal remodeling, survival, receptor localization and distribution, gene transcription, motility, differentiation, proliferation, or angiogenesis.

In other particular example the signaling proteins for which activity states are measured are members of a well-known signaling pathway such as an integrin pathway, a focal adhesion signaling pathway, an Akt signaling pathway, an IL-6R pathway, a growth factor pathway, a chemokine receptor signal pathway, a cell-cycle signaling pathway, a stress signal pathway, an apotosis signaling pathway, a Tau/beta signaling pathway, a pro-inflammatory pathway, a differentiation signaling pathway, a T-cell receptor pathway, a death-receptor signaling pathway, a survival signaling pathway, a MAPK signaling pathway, a p38 MAPK signaling pathway, a G-coupled Receptor signaling pathway, a SAPK/JNK signaling pathway, an insulin receptor signaling pathway, a Wnt signaling pathway, a c-Kit pathway, a c-kit signaling pathway, a B-cell antigen signaling pathway, or a Jak/Stat signaling pathway.

In another embodiment, a method is provided for treatment of a subject having a disease caused by a deranged signaling pathway or network leading to an aberrant cellular response. In this embodiment a sample including a diseased cell is obtained from a subject, and the diseased cell is isolated. Proteins are extracted proteins from the diseased cell and the activity state of a signaling protein extracted from the diseased cell is measured. The activity state of the signaling protein extracted from the diseased cell is compared to an activity state measured for the signaling protein extracted from a reference cell to determine a difference in the activity states of the signaling protein between the diseased cell and the reference cell. A detected difference indicates that the signaling pathway of which the signaling protein is a member is a deranged signaling pathway or network. Based on this information a combination of at least two therapeutic agents is selected for administration to the subject. The selected agents are chosen to target two or more members of the deranged protein signaling pathway or network and to reduce difference in activity state between the diseased and normal cells. Following treatment, additional signaling aberrations may be detected and used to select additional therapeutic agents that can be combined with the first combination.

In yet another embodiment, a method is provided for screening combinations of drugs for treatment of a pathological condition. A combination of drugs targeting two or more nodes in an aberrant a protein signaling pathway or network of a diseased cell exhibiting the pathological condition is selected. In this instance the pathway or network of the diseased cell has a pattern of activity states at one or more nodes that differs in comparison to a pattern of activity states at the one or more nodes for a normal cell. Once the diseased cell is treated with the selected combination of drugs, it is examined to determine whether the combination of drugs produces a pattern of activity states in the diseased cell that is more like the pattern of activity states for the normal cell. This indicates that the combination is a candidate treatment of the pathological condition. Patterns of activity states can be determined and compared using pattern recognition techniques. In more particular embodiments, the pattern of activity states is a pattern of phosphorylation.

In another more particular embodiment, a subject's tissue specimen (or cells obtained therefrom) is analysed (such as by immunohistochemistry, a protein array, an antibody array, bead captue or any other analyte measuring device) to determine whether concordant activation/phosphorylation of the c-kit family of proteins (see, for example, Miguel et al., PNAS, 99: 10458-10463, 2002, incorporated by reference herein) and the estrogen receptor is present. If concordant activation is present, a specific therapeutic combination of inhibitory molecules that includes a combination of an aromatase inhibitor (see, for example, Goss and STrasser-Weippl, *Best Pract Res. Clin. Endocrinol Metab.*, 18: 113-130, 2004, incorporated by reference herein) for estrogen receptor inhibition and STI-572 for cukit/abl kinase inhibition (Novartis, Basel Switzerland) is selected.

The following examples are provided to illustrate certain particular features and/or embodiments, but these examples should not be construed to limit the invention to the particular features or embodiments described.

EXAMPLE 1

Theoretical Model for Individualized Combinatorial Therapy

The synergism exhibited by combinatorial signaling pathway therapy may be demonstrated with a theoretical analysis using differential equations to model a particular signaling pathway containing six components, including a bound ligand (1) that initiates the signal, that is bound by a receptor (2), four downstream intermediate nodes along the signaling pathway (3, 4, 5) and a final node (6), that lead to a final response. A diagram of the modeled signaling pathway is shown below.

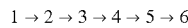

Assuming mass balance, the propagation of a signal through a series of interdependent nodes in a pathway can be modeled as a series of nodes passing along packets of information. When a signal is propagated, the individual proteins physically connect with one another, for example, with the help of enzymes to change their activation state. For instance, tyrosine kinases can enzymatically activate proteins by transferring a phosphate group from an $A^{TP}$ molecule to the protein. Phosphatases perform the reciprocal function of the tyrosine kinase, by removing the phosphate from the protein and consequently inactivating the protein. Thus the relative balance between protein interactions, kinase activity, and phosphatase activity at any point in time determines the activity level of an individualized node in the pathway, and it is possible to potentially modify each component (node) of the signal transduction pathway to influence the final response of the signal.

Signaling can be described in two segments: the propagation of the signal, and the initiation of the signal. The propagation of the signal can be simply thought of as a series of nodes passing along information. Each node or protein individually can be represented through its change in activation state over time. For example, for the nodes 3, 4 and 5:

$$\frac{dx_3}{dt} = c_{31}x_2 - c_{32}x_3$$

$$\frac{dx_4}{dt} = c_{32}x_3 - c_{41}x_4$$

$$\frac{dx_5}{dt} = c_{41}x_4 - c_{42}x_5$$

where c is the rate of change. The transfer of the signal can be expressed as a continuous flow between nodes over time or as a pulse of energy that is transferred at some time as an impulse function. The latter means of transfer can be expressed by assuming that the transfer occurs after the energy accumulates to a threshold value, T.

$$\frac{dx_6}{dt} = \begin{cases} c_{42}x_5 & x_5 \geq T \\ 0, & x_5 < T \end{cases}$$

Initial Conditions:

$$x_1 = 1$$

$$x_2 = 1 @ t = 0$$

Signals can also be initiated by other methods, such as receptor auto-phosphorylation. The theory of population dynamics can characterize the interaction and interdependence of the ligand and the receptor. Using this method the concentration of the bound ligand and the occupied phosphorylated receptor are expressed in terms of their birth and death rates.

$$\frac{dx_1}{dt} = (b_1 - d_1)x_1$$

$$\frac{dx_2}{dt} = (b_2 - d_2 - c_{31})x_2$$

The dynamics of this interaction can be expressed through the birth and death rates of the ligand and receptor. By equating this interaction to an enzyme-substrate kinetics, we can use either the Michaelis-Menten equation or the Hill equation to describe this interaction. Using the Michaelis-Menten equation, $$v = \frac{V\max [S]}{(Km + [S])}$$

the forward rate of bound ligand amount at time t can be expressed as $$b_1 = \frac{c_{11}(x_2/x_1 + x_2)}{c_{12} + (x_2/x_1 + x_2)}$$

and since the receptor and ligand are linked, the birth rate of the receptor, which represents the kinase activity can be expressed as:

$$b_2 = c_{21}b_1$$

Now, since our model exists within a nutrient constrained system. The death rate of the ligand is expresses the phosphatase's dephosphorylation activity. If the ratio of the ligand were low, there would be a rapid influx of phosphatases that can be quantitatively expressed through the power function.

The death rates of the receptor and ligand are also linked.

$$d_2 = c_{23}d_1$$

From an understanding of the mechanism of the receptor-ligand interaction, it is possible to simply the representation of the receptor-ligand interaction in the model. Using Lund's model of the EGF receptor and ligand interaction (Lund et al., *J Biol Chem*, 265:15713-23, 1990), it is possible to deduce that the internalization rate of the receptor complex is proportional to the amount of activated complex.

Using MATLAB, an approximate solution of these interdependent differential equations may be obtained and used to deduce the level of inhibition. As shown in Table 1, the model reveals that targeting several interdependent signal nodes at a low dosage (30%) is equivalent in efficacy to inhibiting the primary upstream receptor node by 90%.

TABLE 1

| INHIBIT: @ | Receptor Only | Receptor & Next Node | Receptor & Middle Node | Receptor & Next Node & Middle Node | Receptor & Next Node & Middle Node & Final Rsp |
|---|---|---|---|---|---|
| 30% | 86.96% | 70% | 86.96% | 70% | 70% |
| 60% | 76.92% | 40% | 76.92% | 40% | 39.7% |
| 90% | 68.96% | 10% | 63.84% | 9.24% | 5.66% |

A table of inhibitor concentrations can be used to predict the end response of a pathway to inhibition at particular nodes in the pathway, as shown in Tables 2-11. Since it is apparent that a high degree of efficacy can be achieved with a low dose of each inhibitor; reduced toxicity (i.e. probability of cross reaction) for drug compounds in the combination can be realized. This unexpected outcome leads to a method of optimization of therapy by finding the lowest dose at multiple interdependent targets. This is completely the opposite from conventional therapy, which strives to find the highest tolerable dose at a single target.

TABLE 2

Level of Final Response (100% = 0.5000)

Level of $x_3$, Next Node

Level of $x_2$, Receptor Inhibition

| Inhibition | 90% | 80% | 70% | 60% | 50% | 40% | 30% | 20% | 10% | 5% | 0% |
|---|---|---|---|---|---|---|---|---|---|---|---|
| 90% | 0.0500 | 0.0526 | 0.0556 | 0.0588 | 0.0625 | 0.0667 | 0.0714 | 0.0769 | 0.0833 | 0.0870 | .0909 |
| 80% | 0.0952 | 0.1000 | 0.1053 | 0.1111 | 0.1176 | 0.1250 | 0.1333 | 0.1429 | 0.1538 | 0.1600 | .1667 |
| 70% | 0.1364 | 0.1429 | 0.1053 | 0.1579 | 0.1667 | 0.1765 | 0.1875 | 0.2000 | 0.2143 | 0.2222 | .2308 |
| 60% | 0.1739 | 0.1818 | 0.1905 | 0.2000 | 0.2105 | 0.2222 | 0.2353 | 0.2500 | 0.2667 | 0.2759 | .2857 |
| 50% | 0.2083 | 0.2174 | 0.2273 | 0.2381 | 0.2500 | 0.2632 | 0.2778 | 0.2941 | 0.3125 | 0.3226 | .3333 |
| 40% | 0.2400 | 0.2500 | 0.2609 | 0.2727 | 0.2857 | 0.3000 | 0.3158 | 0.3333 | 0.3529 | 0.3636 | .3750 |
| 30% | 0.2692 | 0.2800 | 0.2917 | 0.3043 | 0.3182 | 0.3333 | 0.3500 | 0.3684 | 0.3889 | 0.4000 | .4118 |
| 20% | 0.2963 | 0.3077 | 0.3200 | 0.3333 | 0.3478 | 0.3636 | 0.3810 | 0.4000 | 0.4211 | 0.4324 | .4444 |
| 10% | 0.3214 | 0.3333 | 0.3462 | 0.3600 | 0.3750 | 0.3913 | 0.4091 | 0.4286 | 0.4500 | 0.4615 | .4737 |
| 5% | 0.3333 | 0.3455 | 0.3585 | 0.3725 | 0.3878 | 0.4043 | 0.4222 | 0.4419 | 0.4634 | 0.4750 | .4872 |
| 0% | .3448 | .3571 | .3704 | .3846 | .4 | .4167 | .4348 | .4545 | .4762 | .4878 | 0.5000 |

TABLE 3

Level of Final Response (100% = 0.5000)

Level of $x_4$, Middle Node

Level of $x_2$, Receptor Inhibition

| Inhibition | 90% | 80% | 70% | 60% | 50% | 40% | 30% | 20% | 10% | 5% | 0% |
|---|---|---|---|---|---|---|---|---|---|---|---|
| 90% | 0.3192 | 0.3305 | 0.3427 | 0.3558 | 0.3699 | 0.3852 | 0.4019 | 0.4200 | 0.4398 | 0.4504 | 0.4616 |
| 80% | 0.3428 | 0.3550 | 0.3681 | 0.3823 | 0.3975 | 0.4141 | 0.4321 | 0.4517 | 0.4732 | 0.4847 | 0.4968 |
| 70% | 0.3446 | 0.3569 | 0.3702 | 0.3844 | 0.3998 | 0.4164 | 0.4345 | 0.4543 | 0.4759 | 0.4875 | 0.4997 |
| 60% | 0.3448 | 0.3571 | 0.3703 | 0.3846 | 0.4000 | 0.4166 | 0.4348 | 0.4545 | 0.4762 | 0.4878 | 0.5000 |
| 50% | 0.3448 | 0.3571 | 0.3704 | 0.3846 | 0.4000 | 0.4167 | 0.4348 | 0.4545 | 0.4762 | 0.4878 | 0.5000 |
| 40% | 0.3448 | 0.3571 | 0.3704 | 0.3846 | 0.4000 | 0.4167 | 0.4348 | 0.4545 | 0.4762 | 0.4878 | 0.5000 |
| 30% | 0.3448 | 0.3571 | 0.3704 | 0.3846 | 0.4000 | 0.4167 | 0.4348 | 0.4545 | 0.4762 | 0.4878 | 0.5000 |
| 20% | 0.3448 | 0.3571 | 0.3704 | 0.3846 | 0.4000 | 0.4167 | 0.4348 | 0.4545 | 0.4762 | 0.4878 | 0.5000 |
| 10% | 0.3448 | 0.3571 | 0.3704 | 0.3846 | 0.4000 | 0.4167 | 0.4348 | 0.4545 | 0.4762 | 0.4878 | 0.5000 |
| 5% | 0.3448 | 0.3571 | 0.3704 | 0.3846 | 0.4000 | 0.4167 | 0.4348 | 0.4545 | 0.4762 | 0.4878 | 0.5000 |
| 0% | 0.3448 | 0.3571 | 0.3704 | 0.3846 | 0.4000 | 0.4167 | 0.4348 | 0.4545 | 0.4762 | 0.4878 | 0.5000 |

TABLE 4

Level of Final Response (100% = 0.5000)

Level of $x_6$, Final Node

Level of $x_2$, Receptor Inhibition

| Inhibition | 90% | 80% | 70% | 60% | 50% | 40% | 30% | 20% | 10% | 5% | 0% |
|---|---|---|---|---|---|---|---|---|---|---|---|
| 90% | 0.2565 | 0.2857 | 0.2857 | 0.2857 | 0.2970 | 0.3092 | 0.3224 | 0.3368 | 0.3526 | 0.3610 | 0.3699 |
| 80% | 0.3221 | 0.3335 | 0.3458 | 0.3590 | 0.3733 | 0.3887 | 0.4055 | 0.4238 | 0.4438 | 0.4546 | 0.4659 |
| 70% | 0.3389 | 0.3510 | 0.3640 | 0.3779 | 0.3930 | 0.4093 | 0.4271 | 0.4465 | 0.4676 | 0.4790 | 0.4910 |
| 60% | 0.3433 | 0.3555 | 0.3687 | 0.3829 | 0.3982 | 0.4147 | 0.4327 | 0.4524 | 0.4739 | 0.4855 | 0.4976 |
| 50% | 0.3444 | 0.3567 | 0.3699 | 0.3841 | 0.3995 | 0.4161 | 0.4342 | 0.4540 | 0.4756 | 0.4872 | 0.4993 |
| 40% | 0.3447 | 0.3570 | 0.3703 | 0.3845 | 0.3999 | 0.4165 | 0.4346 | 0.4544 | 0.4760 | 0.4876 | 0.4998 |
| 30% | 0.3448 | 0.3571 | 0.3703 | 0.3846 | 0.4000 | 0.4166 | 0.4347 | 0.4545 | 0.4761 | 0.4878 | 0.4999 |
| 20% | 0.3448 | 0.3571 | 0.3704 | 0.3846 | 0.4000 | 0.4167 | 0.4348 | 0.4545 | 0.4762 | 0.4878 | 0.5000 |
| 10% | 0.3448 | 0.3571 | 0.3704 | 0.3846 | 0.4000 | 0.4167 | 0.4348 | 0.4545 | 0.4762 | 0.4878 | 0.5000 |

TABLE 4-continued

Level of Final Response (100% = 0.5000)

| Level of, $x_6$, Final Node | Level of, $x_2$, Receptor Inhibition | | | | | | | | | |
|---|---|---|---|---|---|---|---|---|---|---|
| Inhibition | 90% | 80% | 70% | 60% | 50% | 40% | 30% | 20% | 10% | 5% | 0% |
| 5% | 0.3448 | 0.3571 | 0.3704 | 0.3846 | 0.4000 | 0.4167 | 0.4348 | 0.4545 | 0.4762 | 0.4878 | 0.5000 |
| 0% | 0.3448 | 0.3571 | 0.3704 | 0.3846 | 0.4000 | 0.4167 | 0.4348 | 0.4545 | 0.4762 | 0.4878 | 0.5000 |

TABLE 5

Single Level of Inhibition - Level of Final Response (100% = 0.5000)

| Level of Node Inhibition | 90% | 80% | 70% | 60% | 50% | 40% | 30% | 20% | 10% | 5% | 0% |
|---|---|---|---|---|---|---|---|---|---|---|---|
| $X_2$ | .3448 | .3571 | .3704 | .3846 | .4 | .4167 | .4348 | .4545 | .4762 | .4878 | .5 |
| $X_3$ | .0909 | .1667 | .2308 | .2857 | .3333 | .3750 | .4118 | .4444 | .4737 | .4872 | .5 |
| $X_4$ | .4616 | .4968 | .4997 | .5 | .5 | .5 | .5 | .5 | .5 | .5 | .5 |
| $X_5$ | .4616 | .4968 | .4997 | .5 | .5 | .5 | .5 | .5 | .5 | .5 | .5 |
| $X_6$ | .3699 | .4659 | .4910 | .4976 | .4993 | .4998 | .4999 | .5 | .5 | .5 | .5 |

TABLE 6

| 90% Inhibition | $x_2$ | $x_3$ | $x_4$ | $x_5$ | $x_6$ |
|---|---|---|---|---|---|
| $x_2$ | .3448 | 0.0500 | 0.3192 | 0.3192 | 0.2565 |
| $x_3$ | | .0909 | 0.0832 | 0.0832 | 0.0662 |
| $x_4$ | | | .4616 | 0.3742 | 0.2835 |
| $x_5$ | | | | .4616 | 0.2835 |
| $x_6$ | | | | | .3699 |

TABLE 7

| 80% Inhibition | $x_2$ | $x_3$ | $x_4$ | $x_5$ | $x_6$ |
|---|---|---|---|---|---|
| $x_2$ | .3571 | 0.1000 | 0.3550 | 0.3550 | 0.3335 |
| $x_3$ | | .1667 | 0.1654 | 0.1654 | 0.1544 |
| $x_4$ | | | .4968 | 0.4843 | 0.4405 |
| $x_5$ | | | | .4968 | 0.4405 |
| $x_6$ | | | | | .4659 |

TABLE 8

| 70% Inhibition | $x_2$ | $x_3$ | $x_4$ | $x_5$ | $x_6$ |
|---|---|---|---|---|---|
| $x_2$ | .3704 | 0.1053 | 0.3702 | 0.3702 | 0.3640 |
| $x_3$ | | .2308 | 0.2306 | 0.2306 | 0.2262 |
| $x_4$ | | | .4997 | 0.4982 | 0.4848 |
| $x_5$ | | | | .4997 | 0.4848 |
| $x_6$ | | | | | .4910 |

TABLE 9

| 60% Inhibition | $x_2$ | $x_3$ | $x_4$ | $x_5$ | $x_6$ |
|---|---|---|---|---|---|
| $x_2$ | .3846 | 0.2000 | 0.3846 | 0.3846 | 0.3829 |
| $x_3$ | | .2857 | 0.2857 | 0.2857 | 0.2842 |
| $x_4$ | | | .5 | 0.4998 | 0.4961 |
| $x_5$ | | | | .5 | 0.4961 |
| $x_6$ | | | | | .4976 |

TABLE 10

| 50% Inhibition | $x_2$ | $x_3$ | $x_4$ | $x_5$ | $x_6$ |
|---|---|---|---|---|---|
| $x_2$ | .4 | 0.2500 | 0.4000 | 0.4000 | 0.3995 |
| $x_3$ | | .3333 | 0.3333 | 0.3333 | 0.3328 |
| $x_4$ | | | .5000 | 0.5000 | 0.4990 |
| $x_5$ | | | | .5000 | 0.4990 |
| $x_6$ | | | | | .4993 |

TABLE 11

| 30% Inhibition | $x_2$ | $x_3$ | $x_4$ | $x_5$ | $x_6$ |
|---|---|---|---|---|---|
| $x_2$ | .4348 | 0.3500 | 0.4348 | 0.4348 | 0.4347 |
| $x_3$ | | .4118 | 0.4118 | 0.4118 | 0.4117 |
| $x_4$ | | | 0.5000 | 0.5000 | 0.4999 |
| $x_5$ | | | | 0.5000 | 0.4999 |
| $x_6$ | | | | | 0.4999 |

Extending this concept to tyrosine kinase inhibitors, it is possible to develop selective and specific inhibitors for each node of a pathway. By administering at least two specific inhibitors of the same pathway (or at least with some interdependence of their influence on the final response of the pathway) at lower doses, it is possible to enhance the therapeutic efficacy, reduce the cytotoxicity, and minimize shunting of targets along the pathway. This form of combinatorial therapy is novel since the drug compounds are acting upon interdependent targets.

EXAMPLE 2

Signal Pathway and Signal Network Profiling Using Microarrays

Protein microarrays are well suited to gathering information about the post-translational modifications of proteins that reflect their activity state in signal pathways and networks. Reverse Phase Arrays (RPA), are one example of a protein array that may be used to measure activity states in diseased cells isolated from clinical samples, and can be used to identify candidate treatments of aberrant cell signaling diseases. Candidate treatments can be selected either for a population at large or tailored for the specific cell signaling pathway or network in a specific subject.

A functional map of the state of key pathways within a subject's diseased cells (such as tumor and pre-malignant cells) is one starting point for individualized therapy because it permits a therapy to be tailored to an individual's molecular signaling defects. Moreover, following re-biopsy or molecular imaging, the effect of the treatment can be monitored in real time. If a subject develops resistance to an initial therapy, the treatment can also be altered to address the evolving drug resistance. The map can be used to select combinations of therapeutic agents that can oppose the aberrant pattern of signaling (as reflected by the activity states of the proteins in a protein signaling pathway or network) and return the aberrant pattern to a more normal pattern of signaling where the activity states of individual signaling proteins in an aberrant pathway more closely match the activity states seen for non-diseased cells. For example, if hyperphosphorylation of a particular signaling protein is detected in diseased cells, a combination of therapeutic agents that will decrease the phosphorylation level of the signaling protein could be selected. A decrease in the phosphorylation level could be accomplished with a combination of agents that inhibit upstream signaling events that lead to phosphorylation of the particular protein, either directly or indirectly (such as at preceding steps in a pathway). Alternatively, a decrease in phophorylation could be accomplished with a combination of agents that stimulate dephosphorylation of the hyperphosphorylated protein. For example, a combination of agents that stimulate the action of a phosphatase that is responsible for dephosphorylating the hyperphosphorylated protein and stimulate another downstream signaling event along the pathway. Combinations that both inhibit phosphorylation of the hyperphosphorylated protein and stimulate desphosphorylation of the hyperphosphorylated protein are also possible. Other combinations that can be used to return an aberrant activity state of a signaling protein to a more normal activity state are possible and will be apparent to those of ordinary skill in the art.

The state of protein networks is embodied in post translational modifications and protein-protein, and protein-DNA interactions (see, for example, Hunter, "Signaling—2000 and beyond," *Cell,* 100:113-127, 2000). At an experimental level, the state of specific "nodes" or signaling proteins comprising a portion of a signal pathway or cascade can be judged even though the cell is lysed. This is possible if a) the lysis conditions preserve relevant post-translational modifications, protein-protein binding, or enzymatic activity associated with the pathway under investigation, and b) the measurement system can discriminate the activated form of the node protein (e.g. phosphorylation state or occupancy of a binding site) from the non activated counterpart. Typically the experimental method for mapping pathways following stimulation of cultured cells includes western blotting, and immunoprecipitation (pull down) assays. Protein microarrays, however, can dramatically multiplex, quantify, accelerate, and miniaturize, this type of analysis. Although protein arrays are often portrayed as an extension of transcript profiling arrays, in reality the two technologies provide information that is distinct and complementary. The relative level of a transcript often bears no relationship to the subsequent encoded protein level, and will not measure posttranslational events.

Where information flow through a specific node in the proteomic network includes phosphorylation of a known protein at a specific amino acid sequence, measurement of the proportion of the protein molecules that are phosphorylated reflects the activity state of that node in the signaling pathway or network. If a comparison of this measurement is made over time, or at stages of disease progression, or before and after treatment, a correlation can be made between the activity state of the node and the biologic or disease state. Expanding this concept using protein microarrays to conduct simultaneous analysis of dozens or hundreds of specific activation states, the outcome is a snapshot of the state of entire networks of cellular information at the proteomic level.

Protein microarrays may be used for: a) Discovery of novel ligands or drugs that bind to specific bait molecules on the array, b) Multiplexing immunoassays to develop a miniature panel of serum biomarkers or cytokines, and c) Profiling the state of specific members of known signal pathways and protein networks. For the purposes a) and b), a variety of other techniques exist, for example, mass spectroscopy, ICAT, 2-D gel electrophoresis, bead capture, micro-ELISA and various other clinical analyzers. Although each of these can be used for signal pathway profiling, the use of protein microarrays, especially reverse phase arrays, for profiling the signaling proteins of cellular samples and clinical material offers a number of advantages over the other methods.

Figure 1B:
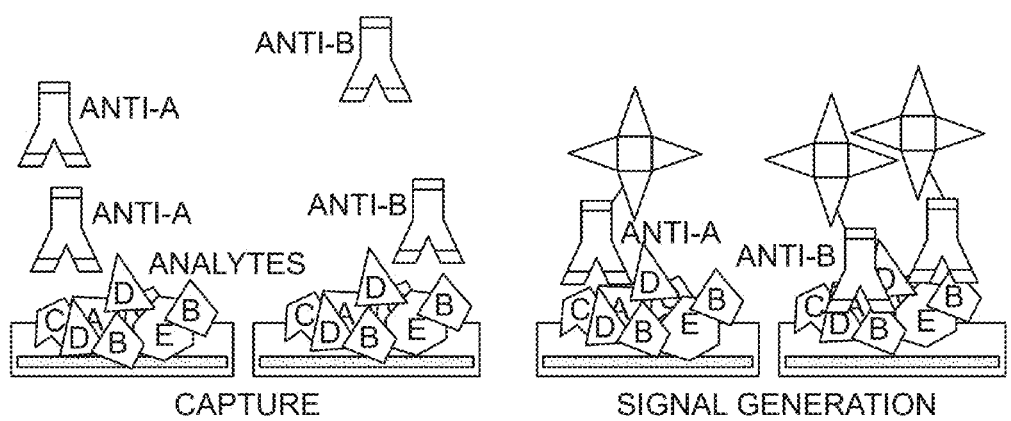

Protein microarray formats fall into two major classes, Forward Phase Arrays (FPA) and Reverse Phase Arrays (RPA), depending on whether the analyte is captured from solution phase or bound to the solid phase. Forward Phase Arrays (FIG. 1A) immobilize a bait molecule such as an antibody designed to capture specific analytes within a mixture of test sample proteins (left). The bound analytes are detected by a second sandwich antibody, or by labeling the analyte directly (right). Reverse Phase Arrays immobilize the test sample analytes on the solid phase (FIG. 1B). An analyte-specific ligand (such as an antibody; left) is applied in solution phase. Bound antibodies are detected by secondary tagging and signal amplification (right).

In the FPA format each array is incubated with one test sample (e.g. a cellular lysate from one treatment condition), and multiple analytes are measured at once. In contrast, the RPA format immobilizes an individual test sample in each array spot, such that an array is comprised of hundreds of different patient samples or cellular lysates. In the RPA format each array is incubated with one detection protein (e.g. antibody) and a single analyte endpoint is measured and directly compared across multiple samples.

Figure 2:
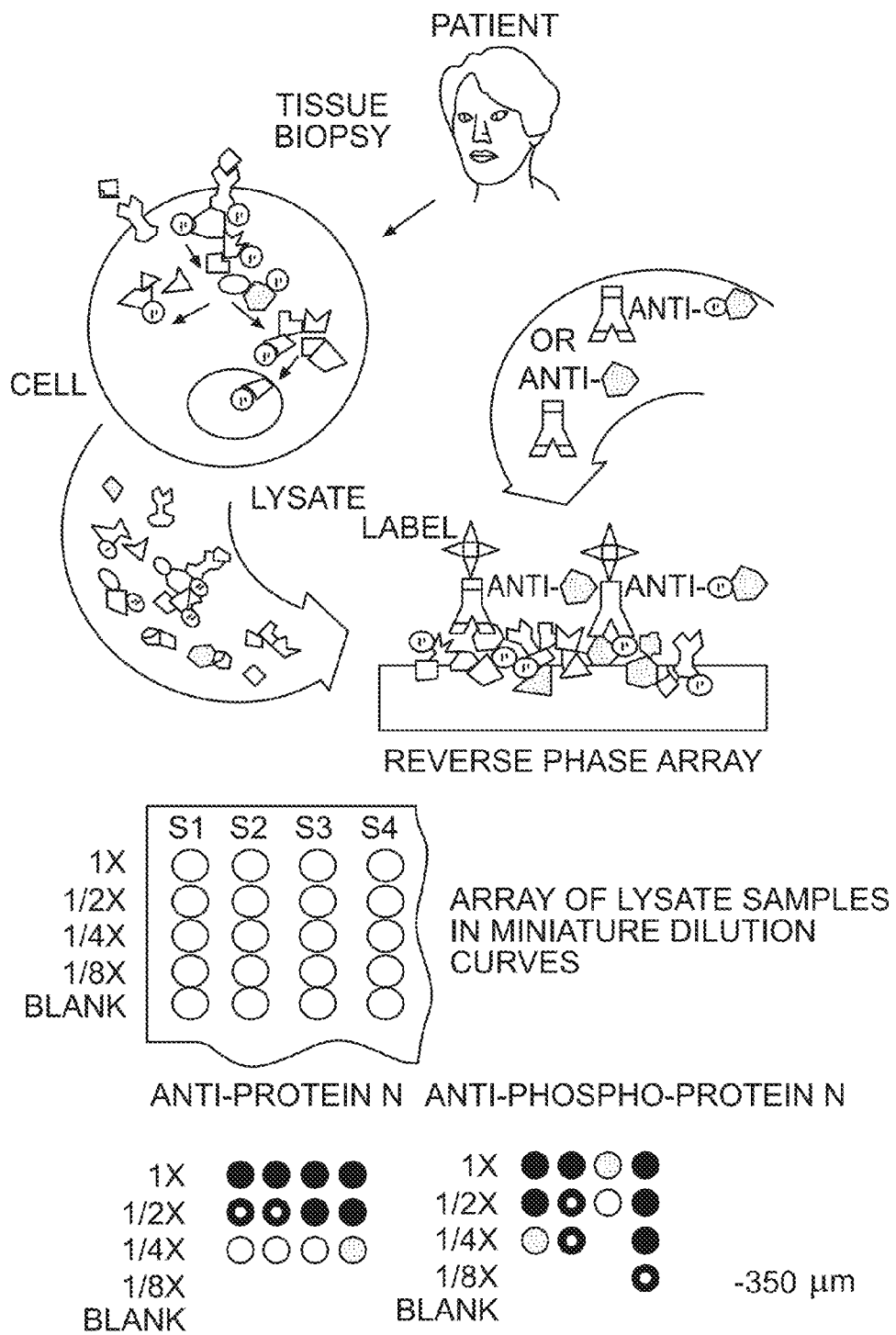
FIG. 2 is a diagram outlining an embodiment in which a reverse phase protein array is applied to analyze the phosphorylation states of signal pathway proteins.

Each spot within an RPA contains an immobilized bait zone typically measuring only a few hundred microns in diameter and containing a solubilized sample of the cellular material itself. Following tissue procurement and microdissection, the cells are lysed and the cellular proteomic repertoire is immobilized onto a solid phase (FIG. 2, top). The immobilized analyte proteins containing those signaling proteins that are phosphorylated during signal transduction are probed with two classes of antibodies that specifically recognize a) the phosphorylated (modified) form of the protein, or b) the total protein regardless of its modified state. Each test sample S1-S4 is arrayed and immobilized in a miniature dilution curve (FIG. 2, middle). Upon signal development and imaging, the relative proportion of the analyte protein molecules that are phosphorylated can be compared between test samples on the same array. For example S3 has a low ratio of phosphorylated to total protein while sample S4 has a high ratio (see FIG. 2, bottom).

The high sensitivity exhibited by RPAs is due in part to the detection probe (such as an antibody) which can be tagged and the fact that the signal is amplified independently from the immobilized analyte protein. Amplification chemistries that are available take advantage of methods developed for highly sensitive commercial clinical immunoassays (see, for example, King et al., "A highly sensitive detection method for immunohistochemistry using biotinylated tyramine," *J Pathol* 183: 237-241, 1997). Coupling the detection antibody with highly sensitive tyramide-based avidin/biotin signal amplification systems can yield detection sensitivities down to fewer than 1000-5000 molecules/spot. A biopsy of 10,000 cells can yield 100 RPA arrays, and each array can be probed with a different antibody.

Figure 3:
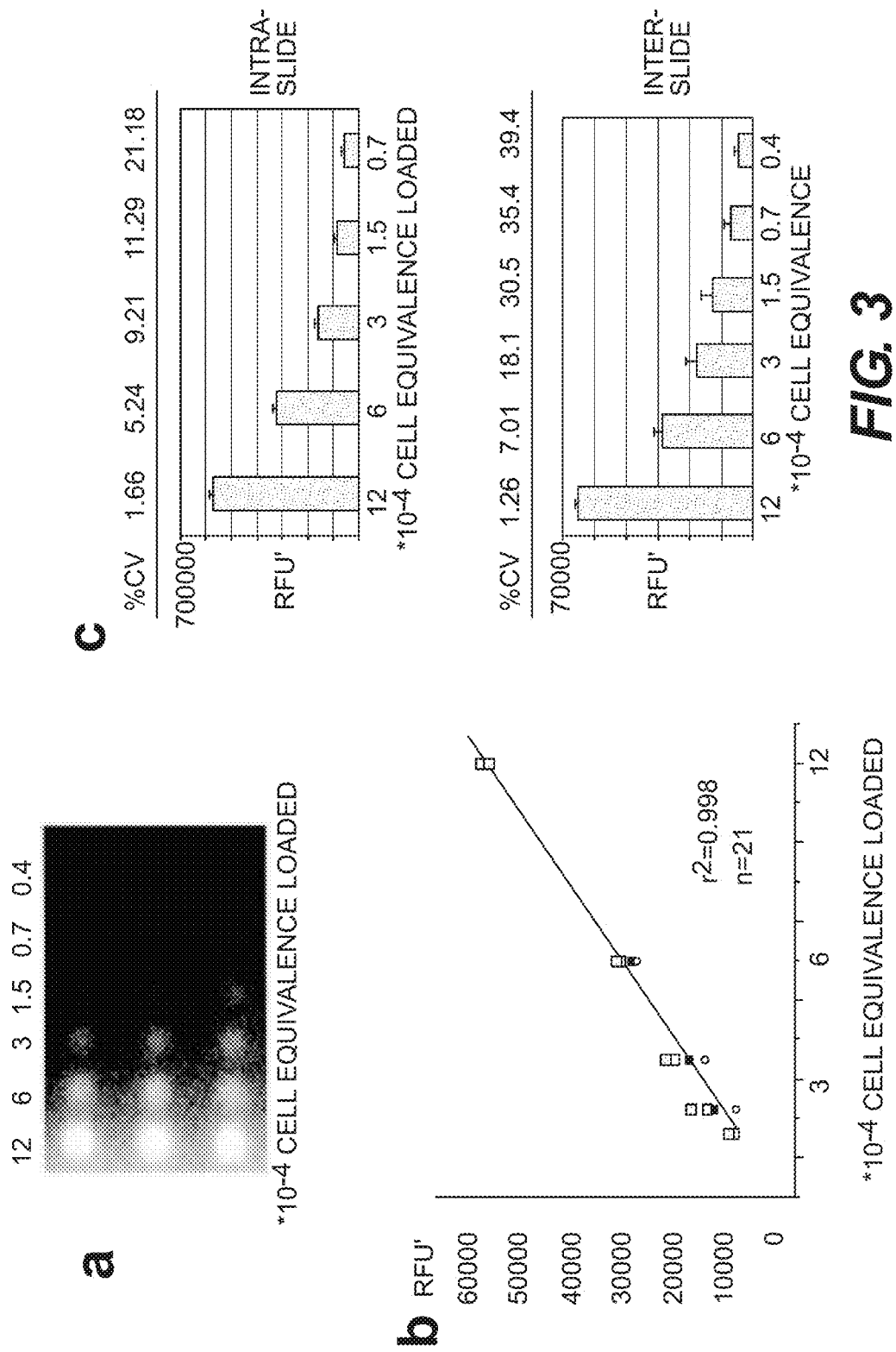
FIG. 3 is a diagram showing validation of reverse phase protein microarray analysis of microdissected lysates.

Using commercially available automated equipment, RPAs exhibit excellent within run and between run analytical precision (3-10% c.v.) (FIG. 3). RPAs do not require direct labeling of the sample analyte, and do not utilize a two-site antibody sandwich. Therefore, there is no experimental variability introduced due to labeling yield, efficiency, or epitope masking. As each array is comprised of dozens or hundreds of experimental samples, subtle differences in an analyte can be measured because each sample is exposed for the same amount of time to the same concentration of primary and secondary antibody and amplification reagents. RPA platforms can utilize reliable commercially available automated stainers designed for immunohistochemistry. FIG. 3 shows a) an annexin-1 stained slide of triplicate arrayed dilution curves ranging over one log of cellular equivalents loaded per spot, b) a graph showing the linearity between immobilized protein lysate and signal intensity between seven replicate slides, and c) a graph showing the intra and inter-spot coefficient of variance % CV.

A factor determining the linearity of a protein array, common to all immunoassays, is the match between the antibody probe concentration (affinity constant) and the unknown concentration of the analyte (Humphery-Smith et al., 2002). Another special and important attribute of the RPA is that each sample is applied in a miniature dilution curve on the array (FIG. 2). In principle a calibration curve is developed for each antibody, for each sample, and for each analyte concentration. This provides an improved means of matching the antibody concentration with the analyte concentration so that the linear range of each analyte measurement is insured.

A starting point for the development of any protein array method is the selection of antibodies with high specificity and adequate affinity. If the experimental focus is cellular signaling analysis, then the platform will employ at least two different kinds of antibodies for each protein. For example, one antibody may be chosen to recognize the phosphorylated form of the protein and the second chosen to recognize the protein regardless of its phosphorylation status. The relative signal generated by both antibodies will reflect the relative proportion of the total protein that is phosphorylated, and therefore activated, at the time the cell was lysed or the tissue was frozen. Selection of antibodies is predicated on the signal pathways to be evaluated, and commercial sources exist for many antibodies recognizing the phosphorylated form of signaling proteins (including Biosource, Camarillo, Calif.; Upstate, Waltham Mass.; Cell Signaling, Beverly Mass.; New England Biolabs, Beverly Mass.; Santa C; Oncogen; Promega; BDTrans; and Sigma). For example, if the pathway of interest emanates from the EGF receptor family, then an example set of antibodies could include those that recognize the phosphorylated and non-phosphorylated forms of, ERB1, ERB2, cRaf, ERK1/2, AKT, CREB, IkappaB, STAT1/3, ELK, BAD, FKHRL, and GSK3B.

Prior to use on an array, each antibody is validated for specificity and sensitivity. Specificity testing may be performed by western blotting, preferably using the same class of material that will be applied to the array. A criterion for specificity is a single band at the appropriate molecular weight, which can be competed with the immunizing antigen. The dilution of the primary antibody will be dictated by the relative binding affinity. This is determined empirically using a known concentration of reference antigen or control lysate. Over one hundred validated (out of approximately 400) commercially available phospho-specific or modification specific antibodies covering mitogenesis, survival, apoptosis, differentiation and motility related pathways are provided below in Table 12.

TABLE 12

| Phospho-Antibodies | MW | Company | Host | Dilution |
| --- | --- | --- | --- | --- |
| 4E-BP1 (Ser65) | <20 | NEB | rabbit | 1:1000 |
| 4E-BP1 (Thr70) | <20 | NEB | rabbit | 1:1000 |
| 14-3-3 Binding Motif | | CellSig | rabbit | 1:1000 |
| Adducin (Ser662) | 80/120 | Upstate | rabbit | 1:1000 |
| Adducin (Ser724) | 80-120 | Upstate | mouse | 1:1000 |
| AFX (Ser193) | 60 | NEB | rabbit | 1:1000 |
| Akt (Ser473) | 65 | Biosource | rabbit | 1:1000 |
| Akt (Ser473) | 64 | NEB | rabbit | 1:1000 |
| Akt (Thr308) | 65 | Biosource | rabbit | 1:1000 |
| Akt (Thr308) | 64 | Upstate | rabbit | 1:1000 |
| Akt (Thr308) | 60 | CellSig | rabbit | 1:1000 |
| AMPK (Thr172) | 62 | CellSig | rabbit | 1:1000 |
| Arrestin 1 (β) | 50 | CellSig | mouse | 1:1000 |
| ATF-2 (Thr71) | 65 | Upstate | rabbit | 1:1000 |
| ATF-2 (Thr71) | 65 | NEB | rabbit | 1:1000 |
| Aurora 2/AIK (Thr288) | 48 | CellSig | rabbit | 1:1000 |
| Bad (Ser112) | 23 | Biosource | rabbit | 1:1000 |
| Bad (Ser112) | 23 | NEB | rabbit | 1:1000 |
| Bad (Ser112) | 23 | Upstate | rabbit | 1:500 |
| Bad (Ser136) | 23 | Biosource | rabbit | 1:500 |
| Bad (Ser136) | 23 | NEB | rabbit | 1:500 |
| Bad (Ser136) | 23 | Upstate | rabbit | 1:500 |
| Bad (Ser155) | 23 | NEB | rabbit | 1:1000 |
| Bcl-2 (Ser70) | 28 | CellSig | rabbit | 1:1000 |
| BRCA1 (Ser1497) | 250 | Upstate | rabbit | 1:500 |
| C3G (Tyr 504) | | Santa C | | |
| CAD (Thr456) | | Santa C | | |
| Caldesmon (Ser789) | 140 | Upstate | rabbit | 1:250 |
| CaM Kinase II (Thr286) | 52/60 | Promega | rabbit | 1:5000 |
| CaM Kinase II α (Thr286) | 50 | Upstate | mouse | 1:500 |
| CaM Kinase II α (Thr286) | 50 | SigmaRBI | mouse | 1:1000? |
| CaM Kinase II α/β (T286/287) | 50/60 | Upstate | rabbit | 1:1000 |
| Caspase-3, cleaved (D175) | 17/19 | NEB | rabbit | 1:1000 |
| Caspase-6, cleaved (Asp162) | 18 | CellSig | rabbit | 1:1000 |
| Caspase-8, cleaved (Asp384) | 10 | CellSig | mouse | 1:1000 |
| Caspase-9 (Ser196) | | Santa C | | |
| Caspase-9, cleaved (315/316) | 10 | Biosource | rabbit | 1:500 |
| Caspase-9, cleaved (D315) | 37 | NEB | rabbit | 1:1000 |
| Catenin(beta) (Ser33/37/Thr41) | 85 | CellSig | rabbit | 1:1000 |
| Catenin(beta) (Thr41/Ser45) | 85 | NEB | rabbit | 1:1000 |
| Caveolin (Tyr14) | 22 | BDTrans | mouse | 1:2500 |
| CD3-zeta(ζ) (C415.9A) | | Santa C | | |
| CD45 (Ser940) | | Santa C | | |
| Cdc2 (Thr161) | 34 | CellSig | rabbit | 1:1000 |
| Cdc2 (Tyr15) | 35 | NEB | rabbit | 1:1000 |
| Cdc6 (Ser106) | | Santa C | | |
| Cdc25 (Ser216) 9D1 | 57 | CellSig | mouse | 1:1000 |
| Cdc25 (Ser216) | 57 | CellSig | rabbit | 1:500 |
| Cdc25C (HMIP-3) (Ser216) | 56-59 | Oncogen | rabbit | 1:2000 |
| Cdc25C (Thr48) | 80 | CellSig | rabbit | 1:1000 |
| Cdk1 (Thr14/Tyr15) | 34? | Biosource | rabbit | 1:1000 |
| Cdk2 (Thr160) | 33 | CellSig | rabbit | 1:1000 |
| Cdk5 (Ser159) | | Santa C | | |
| Cdk5 (Tyr15) | | Santa C | | |
| Chk1 (Ser345) | 56 | CellSig | rabbit | 1:1000 |
| Cofilin (Ser3) | | Santa C | | |
| Connexin-43 (Ser255) | | Santa C | rabbit | 1:500 |
| Connexin-43 (Ser279/282) | | Santa C | | |
| CREB (Ser133) | 46 | CellSig | rabbit | 1:1000 |
| CREB (Ser133) 1B6 | 43 | CellSig | mouse | 1:2000 |
| Cyclin-A (Ser154) | | Santa C | rabbit | 1:500 |
| Cyclin-E (Thr395) | | Santa C | | |
| DFF45, cleaved (D224) | ~10 | NEB | rabbit | 1:250 |
| Dynamin I (Ser795) | | Santa C | | |
| eEF2 (Thr56) | 100 | CellSig | rabbit | 1:1000 |

TABLE 12-continued

| Phospho-Antibodies | MW | Company | Host | Dilution |
|---|---|---|---|---|
| EGFR (Tyr845) | 170 | Biosource | rabbit | 1:1000 |
| EGFR (Tyr992) | 175 | CellSig | rabbit | 1:1000 |
| EGFR (Tyr1045) | 175 | CellSig | rabbit | 1:1000 |
| EGFR (Tyr1068) | 185 | Biosource | rabbit | 1:1000 |
| EGFR (Tyr1086) | 185 | Biosource | rabbit | 1:1000 |
| EGFR (Tyr1148) | 170 | Biosource | rabbit | 1:1000 |
| EGFR (Tyr1173) | 185 | Biosource | rabbit | 1:1000 |
| EGFR (Tyr1173) | 170 | Upstate | mouse | 1:1000 |
| EGFR non-phospho | 170 | Upstate | mouse | 1:1000 |
| eIF2α (Ser51) | 36 | Biosource | rabbit | 1:1000 |
| eIF2α (Ser51) | ~40 | NEB | rabbit | 1:1000 |
| eIF4E (Ser209) | 25 | Biosource | rabbit | 1:1000 |
| eIF4E (Ser209) | 27 | CellSig | rabbit | 1:1000 |
| eIF4G (Ser1108) | 200 | CellSig | rabbit | 1:1000 |
| Elk-1 (Ser383) | 55 | NEB | rabbit | 1:1000 |
| Elk-1 (Ser383) | 62 | CellSig | mouse | 1:1000 |
| eNOS (Ser116) | 132 | Upstate | rabbit | 1:500 |
| eNOS (Ser1177) | about 150 | NEB | rabbit | 1:1000 |
| eNOS (Thr495) | 132 | Upstate | rabbit | 1:1000 |
| ErbB2 (Tyr877) | 185 | CellSig | rabbit | 1:1000 |
| ErbB2 (Tyr1112) | 185 | CellSig | rabbit | 1:1000 |
| ErbB2 (Tyr1248) | 185 | CellSig | rabbit | 1:1000 |
| ErbB2 (Tyr1248) | 185 | Upstate | rabbit | 1:2000 |
| ERK 1/2 (Thr183) | 42/44 | Promega | rabbit | 1:4000 |
| ERK 1/2 (Thr202/Tyr204) | 42/44 | CellSig | rabbit | 1:1000 |
| ERK 1/2 (Thr202/Tyr204) | 42/44 | NEB | mouse | 1:2000 |
| ERK 1&2/MAPK (Thr185/Tyr187) | 42/44 | Biosource | rabbit | 1:1000 |
| ERK5/BMK1 (Thr218/Tyr220) | 88 (30-35) | Biosource | rabbit | 1:5000 |
| Estrogen Receptor α (Ser118) | 65.5 | CellSig | mouse | 1:1000 |
| Estrogen Receptor α (Ser167) | | Santa C | | |
| Etk (Tyr40) | 76 | CellSig | rabbit | 1:1000 |
| Ezrin (Tyr146) | | Santa C | | |
| Ezrin (Tyr354) | | Santa C | | |
| FADD (Ser194) | | Santa C | | |
| FAK (Ser722) | 125 | Biosource | rabbit | 1:1000 |
| FAK (Ser910) | 125 | Biosource | rabbit | 1:1000 |
| FAK (Tyr397) | 125 | Biosource | rabbit | 1:1000 |
| FAK (Tyr407) | 125 | Biosource | rabbit | 1:500 |
| FAK (Tyr576) | 125 | Biosource | rabbit | 1:1000 |
| FAK (Tyr577) | 125 | Biosource | rabbit | 1:400 |
| FAK (Tyr861) | 125 | Biosource | rabbit | 1:600 |
| FAK (Tyr925) | 125 | Biosource | rabbit | 1:1000 |
| FKHR (Ser256) | 62 | NEB | rabbit | 1:1000 |
| FKHRL1 (Ser253) | 97 | Upstate | rabbit | 1:500 |
| FKHRL1 (Thr32) | 100 | Upstate | rabbit | 1:1000 |
| FKHR(Thr24)/FKHRL1 (Thr32) | 68/97 | CellSig | rabbit | 1:1000 |
| Flg (Tyr766) | | Santa C | | |
| Gab (Tyr627) | | Santa C | | |
| GluR-1 (Ser863) | | Santa C | | |
| gp130 (Ser782) | | Santa C | | |
| GSK3alpha/beta (Ser21/9) | 51/47 | NEB | rabbit | 1:1000 |
| GSK3alpha/beta (Tyr279/216) | 51/47 | Biosource | rabbit | 1:600 |
| GSK3beta (Ser9) | 47 | Biosource | rabbit | 1:4000 |
| GSK3beta (Tyr216) | | Santa C | | |
| H2AX (Ser139) | 14 | Upstate | rabbit | 1:1000 |
| Hck (Tyr411) | | Santa C | | |
| Histone H1 hyperphosphorylated | 32 (64, 130) | Upstate | rabbit | 1:1000 |
| Histone H3 (Ser10) 6G3 | 17 | CellSig | mouse | 1:2000 |
| Histone H3 (Ser10) | 17 | Upstate | rabbit | 1:2000 |
| Histone H3 (Ser28) | 17 | Upstate | rabbit | 1:1000 |
| Histone (Acetyl-) H3 (Lys9) | 17 | CellSig | rabbit | 1:1000 |
| HSP 27 (Ser15) | 27 | Upstate | sheep | 1:200 |
| HSP 27 (Ser78) | 27 | Upstate | sheep | 1:300 |
| HSP 27 (Ser82) | 27 | CellSig | rabbit | 1:1000 |
| IκBα (Ser32) | 40 | NEB | rabbit | 1:1000 |
| IκBα (Ser32/36) 5A5 | 40 | CellSig | mouse | 1:1000 |
| InsulinR (Y1146)/IGF-IR (Y1131) | 95 | CellSig | rabbit | 1:1000 |
| InsulinR/IGF1R (Y1158) | 95 | Biosource | rabbit | 1:1000 |
| InsulinR/IGF-1R (Y1162/1163) | 95 | Biosource | rabbit | 1:1000 |
| Integrin β1 Receptor (T788/789) | 130 | Biosource | rabbit | 1:1000 |
| IRS-1 Substrate (Ab-1) | | Oncogen | rabbit | 1:5000 |
| IRS-1 (Ser616) | 165 | Biosource | rabbit | 1:300 |
| Jak1 (Tyr1022/1023) | 130 | Biosource | rabbit | 1:2000 |
| Jak2 (Tyr1007/1008) | 130 | Biosource | rabbit | 1:1000 |
| Jak2 (Tyr1007/1008) | 130 | Upstate | rabbit | 1:1000 |
| JNK 1 & 2/SAPK (Y183/185) | 46 & 54 | Biosource | rabbit | 1:1000 |
| c-Jun (Ser63) | 47 | NEB | rabbit | 1:1000 |
| c-Jun (Ser63) KM-1 | | Santa C | mouse | |
| c-Jun (Ser73) | 48 | CellSig | rabbit | 1:1000 |
| Kip1 p27 (Thr187) | 27 | Upstate | rabbit | 1:1000 |
| Lck (Ser158) | 56 | Biosource | rabbit | 1:1000 |
| Lck (Tyr192) | 56 | Biosource | rabbit | 1:1000 |
| Lck (Tyr505) | 56 | Biosource | rabbit | 1:1000 |
| Leptin Receptor (Tyr985) | 150 (90) | Upstate | rabbit | 1:1000 |
| Leptin Receptor (Tyr1138) | 150 (90) | Upstate | rabbit | 1:1000 |
| Lyn (Tyr507) | 53, 56 | CellSig | rabbit | 1:1000 |
| Lyn (Tyr508) | | Santa C | | |
| MAPKAP Kinase-2 (Thr222) | 66 | Upstate | rabbit | 1:1000 |
| MAPKAPKinase-2 (Thr334) | 47 | CellSig | rabbit | 1:1000 |
| M-CSF Receptor (Tyr723) | 175 | CellSig | rabbit | 1:1000 |
| MEK-1/2 (Ser217/221) | 45 | CellSig | rabbit | 1:1000 |
| MEK-1/2 (Ser218/222) | | Santa C | | |
| MEK-3/6 (Ser189) | | Santa C | | |
| MEK-3/6 (Ser189/207) B-9 | | Santa C | mouse | |
| MEK-4 (Thr261) | | Santa C | | |
| Met (Y1234/1235) | 140 | Upstate | rabbit | 1:250 |
| MKK-3/6 (Ser189/207) | 40/35 | NEB | rabbit | 1:1000 |
| MLC (Thr18/Ser19) | | Santa C | | |
| Mnk1 (Thr197/202) | 52 | CellSig | rabbit | 1:1000 |
| MPM-2, Ser/Thr-Pro | 100-130 | Upstate | mouse | 1:1000 |
| MSK1 (Ser360) | ~100 | NEB | rabbit | 1:1000 |
| MSK1 (Ser376) | 90 | NEB | rabbit | 1:1000 |
| MSK1 (Thr581) | 90 | NEB | rabbit | 1:1000 |
| c-myc (Thr58/Ser62) | 66 | NEB | rabbit | 1:1000 |
| MYPT1 (Thr850) | 70 | Upstate | sheep | 1:100 |
| Neu (Tyr1248) | | Santa C | | |
| NF-κB p65 (Ser536) | 65 | CellSig | rabbit | 1:1000 |
| NF-L (Ser55) | | Santa C | | |
| Nibrin (Ser343) | | Santa C | rabbit | 1:500 |
| NIK (Thr559) | | Santa C | | |
| nNOS (Ser1416) | 170 | Upstate | rabbit | 1:2000 |
| NOS3 (Ser1177) | | Santa C | | |
| Notch 1, cleaved | 110-115 | CellSig | rabbit | 1:1000 |
| NR1 (Ser896) | 120 | Upstate | rabbit | 1:500 |
| NR1 (Ser897) | 120 | Upstate | rabbit | 1:500 |
| Op18 (Ser16) | | Santa C | | |
| p21 (Ser146) | | Santa C | | |
| p27 (Ser10) | | Santa C | | |
| p38 (Thr180/Tyr182) | 38 | Biosource | rabbit | 1:1000 |
| p38 MAPK (Thr180/Tyr182) | 42 | CellSig | mouse | 1:2000 |
| p38 (Thr180/Tyr182) | 38 | NEB | rabbit | 1:1000 |
| p53 (Ser6) | 53 | NEB | rabbit | 1:1000 |
| p53 (Ser9) | 53 | CellSig | rabbit | 1:1000 |
| p53 (Ser15) | 53 | CellSig | rabbit | 1:1000 |
| p53 (Ser20) | 53 | NEB | rabbit | 1:1000 |
| p53 (Ser37) | 53 | CellSig | rabbit | 1:1000 |
| p53 (Ser392) | 53 | Biosource | rabbit | 1:600 |
| p53 (Ser392) | 53 | NEB | rabbit | 1:1000 |
| p53 (Thr55) | | Santa C | | |
| p70 S6 (Ser41) | | Santa C | | |
| p70 S6 (Thr389) | 70 | NEB | rabbit | 1:1000 |
| p70 S6 (Thr412) | 70 | Upstate | rabbit | 1:1000 |
| p70 S6 (Thr421/Ser424) | 70 | NEB | rabbit | 1:1000 |
| p90/RSK (Thr573) | 90 | CellSig | rabbit | 1:1000 |
| p95NBS1 (Ser343) | 95 | CellSig | rabbit | 1:1000 |
| p107 (probably tumor suppr.) | 107 | Pharming | mouse | 1:1000 |
| PAK1 (S199/204)/PAK2 (S192/7) | 65/59 | CellSig | rabbit | 1:1000 |
| PAK1 (Thr423) | | Santa C | | |
| PAK1 (Thr423)/PAK2 (Thr402) | 61/58 | CellSig | rabbit | 1:1000 |
| PARP (site214/215) | 85 = clvd | Biosource | rabbit | 1:1000 |
| PARP (site214/215) | 89 | NEB | rabbit | 1:1000 |
| Paxillin (Tyr31) cytosk. scaff. | 68 | Biosource | rabbit | 1:1000 |
| Paxillin (Tyr118) | 68 | BDTrans | mouse | 1:250 |
| Paxillin (Tyr118) | 68 | Biosource | rabbit | 1:1000 |

TABLE 12-continued

| Phospho-Antibodies | MW | Company | Host | Dilution |
|---|---|---|---|---|
| Paxillin (Tyr181) | 68 | Biosource | rabbit | 1:1000 |
| PDGF Receptor β (Tyr716) | 190 | Upstate | rabbit | 1:250 |
| PDGF Receptor β (Tyr751) | | Santa C | | |
| PDGF Receptor β (Tyr857) | | Santa C | | |
| PDGF Receptor β (Tyr1009) | | Santa C | | |
| PDGF Receptor β (Tyr1021) | | Santa C | | |
| PDK1 Docking Motif (Ser/Thr) | many | CellSig | rabbit | 1:2000 |
| PDK1 (Ser241) | 63 | CellSig | rabbit | 1:1000 |
| PERK (Thr980) | 170 | CellSig | rabbit | 1:1000 |
| Phospholamban (Ser16) | 5-25 | Upstate | rabbit | 1:800 |
| Phospholipase C g-1 (Tyr783) | 135 | Biosource | rabbit | 1:1000 |
| PI 3-Kinase p85a (Tyr508) | | Santa C | | |
| PKA, RII (Ser96) | 51 (40 unk) | Upstate | rabbit | 1:100 |
| PKC (Ser) Substrate | N/A | CellSig | rabbit | 1:1000 |
| PKC alpha (Ser657) | ≈80 | Upstate | rabbit | 1:500 |
| PKC beta(pan) (Ser660) | | NEB | rabbit | 1:1000 |
| PKC delta (Ser643) | 76 | NEB | rabbit | 1:1000 |
| PKC delta (Thr505) | 80-90 | NEB | rabbit | 1:1000 |
| PKC epsilon (Ser719) | 90 | Upstate | rabbit | 1:500 |
| PKC epsilon (Ser729) | | Santa C | | |
| PKC theta (Thr538) | 79 | NEB | rabbit | 1:1000 |
| PKC zeta/lambda (Thr410/403) | 76 | CellSig | rabbit | 1:1000 |
| PKD/PKCμ (Ser744/748) | 115 | NEB | rabbit | 1:1000 |
| PKD/PKCμ (Ser916) | 115 | NEB | rabbit | 1:1000 |
| PKR (Thr446) | 74 | CellSig | rabbit | 1:1000 |
| PKR (Thr451) | 65-68 | Biosource | rabbit | 1:500 |
| PKR (Thr446/451) | 74 | CellSig | rabbit | 1:1000 |
| cPLA$_2$ (Ser505) | 110 | CellSig | rabbit | 1:1000 |
| PLCβ3 (Ser537) | 150 | CellSig | rabbit | 1:1000 |
| PLCγ1 (Tyr783) | | Santa C | | |
| PP2A (Tyr307) | | Upstate | mouse | |
| PRC1 (Thr481) | | Santa C | | |
| PRK1 (Thr778)/PRK2 (Thr816) | 120 & 140 | CellSig | rabbit | 1:1000 |
| PRK2 (Thr816) | 60 | Upstate | sheep | 1:400 |
| PTEN (Ser380) | 54 | CellSig | rabbit | 1:1000 |
| PTEN (Ser380/Thr382/383) | 54 | CellSig | rabbit | 1:1000 |
| PTEN (A2B1) C-terminus | 54 | Santa C | mouse | 1:100 |
| PTEN (N-19) N-terminus | 54 | Santa C | goat | 1:100 |
| Pyk2 (Tyr402) | 116 not ph | Biosource | rabbit | 1:1000 |
| Pyk2 (Tyr579) | 125 | Biosource | rabbit | 1:500 |
| Pyk2 (Tyr580) | 116 | Biosource | rabbit | 1:130 |
| Pyk2 (Tyr579/580) | 116 | Biosource | rabbit | 1:500 |
| Pyk2 (Tyr881) | 116 | Biosource | rabbit | 1:600 |
| Rac1/cdc42 (Ser71) | 28 | CellSig | rabbit | 1:1000 |
| Raf(c-) (Ser259) | | NEB | rabbit | 1:1000 |
| Raf(c-) (Ser621) | | Biosource | rabbit | 1:300 |
| Raf(c-) (Tyr340/341) | | Biosource | rabbit | 1:500 |
| Raf-1 (Ser338) | | Santa C | | |
| Raf-1, A-Raf (Ser338) | 74 | Upstate | rat | 1:1000 |
| Rb | 110 | Translab | mouse | 1:250 |
| Rb (IF8) sc-102 | 110 | Santa C | mouse | 1:200 |
| Rb (C-15) sc-050 | 110 | Santa C | rabbit | 1:200 |
| Rb (Ser249/Thr252) | 110 | Biosource | rabbit | 1:1000 |
| Rb (Ser780) | 110 | NEB | rabbit | 1:1000 |
| Rb (Ser807/811) | 110 | Biosource | rabbit | 1:1000 |
| Rb (Thr356) | 110 | Biosource | rabbit | 1:1000 |
| Rb (Thr821) | 110 | Biosource | rabbit | 1:1000 |
| Rb (Thr826) | 110 | Biosource | rabbit | 1:800 |
| Rb2 | 130 | Translab | mouse | 1:1000 |
| Ribosomal Protein S6 (Ser235) | 40 | Upstate | sheep | 1:1000 |
| RNA polymeraseII, cloneCTD4H8 | 210-220 | Upstate | mouse | 1:800 |
| RON (Tyr1330/1337) | 185 | Biosource | rabbit | 1:500 |
| Rsk1/MAPKAP-K1a | 90 | Upstate | rabbit | 1:500 |
| Rsk1 (Ser227) | | Santa C | | |
| Rsk1/MAPKAP (Ser363) | 90 | Upstate | sheep | 1:250 |
| Rsk1 (Ser376) | | Santa C | | |
| Rsk1 (Ser380) | | Santa C | | |
| Rsk1/MAPKAP (Ser380) | 90 | Upstate | sheep | 1:250 |
| Rsk1 (Ser381) | 90 | NEB | rabbit | 1:1000 |
| Rsk1/MAPKAP (Thr359) | 90 | Upstate | sheep | 1:500 |
| Rsk1 (Thr359/Ser363) | | Santa C | | |
| Rsk3 (Thr353/356) | 90 | NEB | rabbit | 1:1000 |
| SAPK/JNK (Thr183/Tyr185) | 46/54 | NEB | rabbit | 1:1000 |
| SHC (Y239) | 46, 52, 67 | Upstate | rabbit | 1:2000 |
| SHC (Y317) | 46, 52, 67 | Upstate | rabbit | 1:500 |
| Smad1 (Ser463/465) | 65-66 | Upstate | rabbit | 1:1000 |
| Smad2 (Ser465/467) | 55-60 | Upstate | rabbit | 1:500 |
| Smad2/3 (Ser433/435) | | Santa C | | |
| Src (Tyr139) | | Santa C | | |
| Src (Tyr215) | 60 | Biosource | rabbit | 1:500 |
| Src (Tyr416) | | Santa C | | |
| Src (Tyr418) | 60 | Biosource | rabbit | 1:1000 |
| Src (Tyr527) | 60 | CellSig | rabbit | 1:1000 |
| Src (Tyr529) | 60 | Biosource | rabbit | 1:500 |
| STAT1 (Ser727) | 92 | Biosource | rabbit | 1:1000 |
| STAT1 (Ser727) | 92 | Upstate | rabbit | 1:1000 |
| STAT1 (Tyr701) | 92 | Biosource | rabbit | 1:2000 |
| STAT1 (Tyr701) | 92 | Upstate | rabbit | 1:1000 |
| STAT2 (Tyr689) | 113 | Upstate | rabbit | 1:1000 |
| STAT3 (Ser727) | 89 | Biosource | rabbit | 1:500 |
| STAT3 (Ser727) | 89 | CellSig | rabbit | 1:1000 |
| STAT3 (Ser727) | 89 | Sigma | rabbit | 1:1000 |
| STAT3 (Tyr704) | 92 | Upstate | mouse | 1:10000 |
| STAT3 (Tyr705) | 90 | Biosource | rabbit | 1:1000 |
| STAT3 (Tyr705) | 89 | CellSig | rabbit | 1:1000 |
| STAT3 (Tyr705) | 89 | Sigma | rabbit | 1:1000 |
| STAT5A/B (Ser726/731) | 97 | Upstate | rabbit | 1:1000 |
| STAT5A/B (Tyr694/699) | 95 | Sigma | rabbit | 1:1000 |
| STAT5A/B (Tyr694/699) | 92 | sigma | mouse | 1:1000 |
| STAT5A/B (Tyr694/699) | 92 | Upstate | rabbit | 1:1000 |
| STAT5A/B (Tyr694/699) | 92 | Upstate | mouse | 1:1000 |
| STAT6 (Tyr641) | >105 | NEB | rabbit | 1:1000 |
| Synapsin 1 (Ser553) | | Santa C | | |
| Syndecan-4 (Ser179) | | Biosource | rabbit | 1:100 |
| TAL1 (Ser122) | | Santa C | | |
| Tie2 (Ab-1) (Tyr1094/1102) | 140 | Oncogen | rabbit | |
| Tie2 (Ab-2) (Tyr1106/1111) | 140 | Oncogen | rabbit | |
| TrkA (Tyr490) = high aff. NGFR | 165 | NEB | rabbit | 1:1000 |
| TrkA (Tyr496) (E-6) | | Santa C | mouse | |
| TrkA (Tyr496) | | Santa C | | |
| TrkA (Tyr674/675) | about 130 | NEB | rabbit | 1:750 |
| TrkA (Tyr680/681) | | Santa C | | |
| Tyk2 (Tyr1054/1055) | 140 | CellSig | rabbit | 1:1000 |
| VEGF Receptor-1 (Ab-1) | 180 | Oncogen | rabbit | |
| VEGF Receptor-1 (Ab-2) | 180 | Oncogen | rabbit | |
| VEGF Receptor-2 (Ab-1) (Y1169) | 180 | Oncogen | rabbit | |
| VEGF Receptor-2 (Tyr951) | 180 | CellSig | rabbit | 1:1000 |
| VEGF Receptor-2 (Tyr996) | 180 | CellSig | rabbit | 1:1000 |
| VEGF Receptor-2/3 (Ab-1) | 180 | Oncogen | rabbit | |
| Vimentin (Ser72) | | Santa C | | |
| WT (Ser363) | | Santa C | | |
| Zap-70 (Tyr292) | | Santa C | | |
| Zap-70 (Tyr319) | | Santa C | | |
| Zap-70 (Tyr493) | 70 | CellSig | rabbit | 1:1000 |

Table 1 - Validated phospospecific antibodies for use in the disclosed methods.

Since cellular signaling processes are dominated by the context of the cell type and the tissue microenviroenment, microdissection such as LCM of the heterogeneous tissue sample is therefore helpful for obtaining especially relevant information on the in vivo state of signaling pathways (Laser Capture Microdissection; see, for example, Emmert-Buck et al., "Laser capture microdissection," *Science,* 274:998-1001, 1996 and U.S. Pat. Nos. 6,251,516 and 6,251,467, and U.S. patent application Ser. No. 09/913,667 (now U.S. Pat. No. 6,969,614) which are all incorporated herein by reference). LCM is a technique whereby pure populations or subpopulations of desired cell types may be isolated that enables direct comparisons of the protein content and protein characteristics of proteins isolated from tumor and normal cells, even from the same tissue sample. In one example of the LCM process, a transparent polymeric transfer film is applied to the surface of the tissue section. Under a microscope, the operator views the thin tissue section through the glass slide on which it is mounted and chooses microscopic clusters of cells to study. When the cells of choice are in the center of the field of view, the operator pushes a button that activates a near IR laser diode integrated with the microscope optics. The pulsed laser beam activates a precise spot on the transfer film immediately above the cells of interest. At this precise location the film melts and fuses with the underlying cells of choice. When the film is removed, the chosen cell(s) are tightly held within the focally expanded polymer, while the rest of the tissue is left behind. The exact morphology of the procured cells is retained and held on the transfer film, ensuring preservation of the cells' intracellular components such as DNA, RNA, and proteins for future analysis. The removed transfer film and cells are transferred onto a plastic cap (referred to as an LCM cap) for subsequent analysis. Alternatively, the transfer film over particular cells may be ablated to expose the desired cells underneath, which are then treated to extract their constituent proteins, while the proteins of other cells which remain covered are not extracted.

The LCM process makes it possible to obtain only cells exhibiting the desired morphology for study. In addition, identifying cells under microscopic view using immunohistochemical methods, for example, fluorescent antibodies and fluorescence microscopy, makes it possible to isolate cells based on other characteristics, such as the presence of marker proteins on the surface that are characteristic of particular types of cells, such as tumor cells.

In order to reduce protein degradation by phosphatases and proteinases, the tissue may be snap-frozen, for example, in liquid nitrogen, immediately after procurement. Protein extraction buffers with ionic and non-ionic detergents, may be used to effectively solubilize the cells, while preserving phosphorylated proteins. Moreover, Laser Capture Microdissection can employ proteinase and phosphatase inhibitors directly in the fixation and staining baths (Simone et al., "Sensitive immunoassay of tissue cell proteins procured by laser capture microdissection," *Am J Patho*, 156: 445-452, 2000, incorporated herein by reference).

Protein microarrays may be printed using the same technology used for DNA microarrays, but the protein array layout is vastly different than a typical DNA array. Both printing technologies transfer sample fluid from a microtiter plate onto a substratum, usually a coated glass slide. The substratum requirements for protein arrays are 1) high binding capacity 2) minimum effect on the protein structure and 3) low background. Nitrocellulose coated glass slides are a common substratum for protein arrays (FAST slides, Schleicher & Schuell BioSciences, Keene, N.H.). Proteins bind to nitrocellulose via electrostatic interactions in an irreversible manner. The nitrocellulose polymer coating of FAST slides permits protein binding capacities of 75-150 ug/cm$^2$ in a volume of 0.3-2 nL/spot. Chromogenic, fluorometric and luminescent detection methods may be used with FAST slides with an adequate signal/noise ratio. Protein arrays may also be printed in sector formats. A sector array consists of multiple small pads of substratum on a slide. A reservoir placed around each sector permits a different antibody to be used for probing the samples. The sector format miniaturizes the array, providing an increased signal/noise ratio.

Microarrays may be printed in a variety of configurations using several different types of printing methods (see, for example, Schena, "Microarray biochip technology,", Eaton Pub., Natick, Mass., 2000, incorporated herein by reference). Printing technology currently exists in two forms: contact and non-contact devices. Contact printing is accomplished by direct contact between the print head and the substratum. Non-contact printing dispenses a minute volume of sample above the substratum. Examples of contact printing formats are solid pin, quill, and pin and ring assemblies. Non-contact printing technology utilizes piezoelectric or syringe solenoid devices.

Sample volume, viscosity, number of arrays required and substratum are parameters to be considered prior to selecting a printing system. Pinhead spacing determines the configuration for the microtiter plate that holds the sample. Pin spacing of 9.0 mm may be used with 96-well or 384-well plate formats. Pin spacing of 4.5 mm is compatible with 384-well plates. Reproducibility of printing is affected by variations in the slide surface properties, mechanical differences between the pins and pin cleanliness. The pins are subject to corrosion due to the cell lysis extraction buffers. Periodic cleaning of the pins ensures reproducible printing. The printing assembly should accommodate the choice of substratum surface, usually coated 25×75 mm glass slides. Repeatability, accuracy and resolution of the print assembly determine the final quality of the array printing. The array density is determined by the spot spacing, which is a function of the pin size. Spots are preferably printed at a minimum distance of 1.5 times the pinhead diameter. For example, a 500 µm pin will utilize printing spots no closer than 750 um. This spacing allows adequate space between each spot for analysis and avoids sample carryover from spot-to-spot.

A variety of protein array labels and amplification chemistries are available (see, for example, King et al, *J. Pathol*, 183: 237-241, 1997; Kukar et al., "Protein microarrays to detect protein-protein interactions using red and green fluorescent proteins," *Anal Biochem*, 306: 50-54, 2002; Morozov et al., "Direct detection of isotopically labeled metabolites bound to a protein microarray using a charge-coupled device," *J Biochem Biophys Methods* 51: 57-67, 2002; Schweitzer et al., "Multiplexed protein profiling on microarrays by rolling-circle amplification," *Nat Biotechnol*, 20: 359-365, 2002; and Wiese, "Analysis of several fluorescent detector molecules for protein microarray use," *Luminescence* 18: 25-30, 2003). These include fluorescent, radioactive, luminescent, and colorimetric read-outs. Amplification can be achieved by enzymatic cleavage of colorimetric, luminescent and fluorescent substrates. Several amplification systems employ coupling of nucleic acids to proteins, and thereby take advantage of the PCR method. Amplification may be helpful to achieve the sensitivity adequate for routine analysis of relatively low abundance proteins.

The baseline sensitivity of detection dictates the minimum number of cells that can be profiled on the array. Using a dilution curve of a known concentration of reference antigen, the first step is to determine the intra- and inter-slide coefficients of variance. Baseline sensitivity is defined as a signal 2 standard deviations above background. Using the same amplification or labeling chemistries, the baseline sensitivity is different for each antibody choice. This is because each antibody has a different affinity and background binding, and its cognate antigen falls within a different dynamic range.

Figure 4:
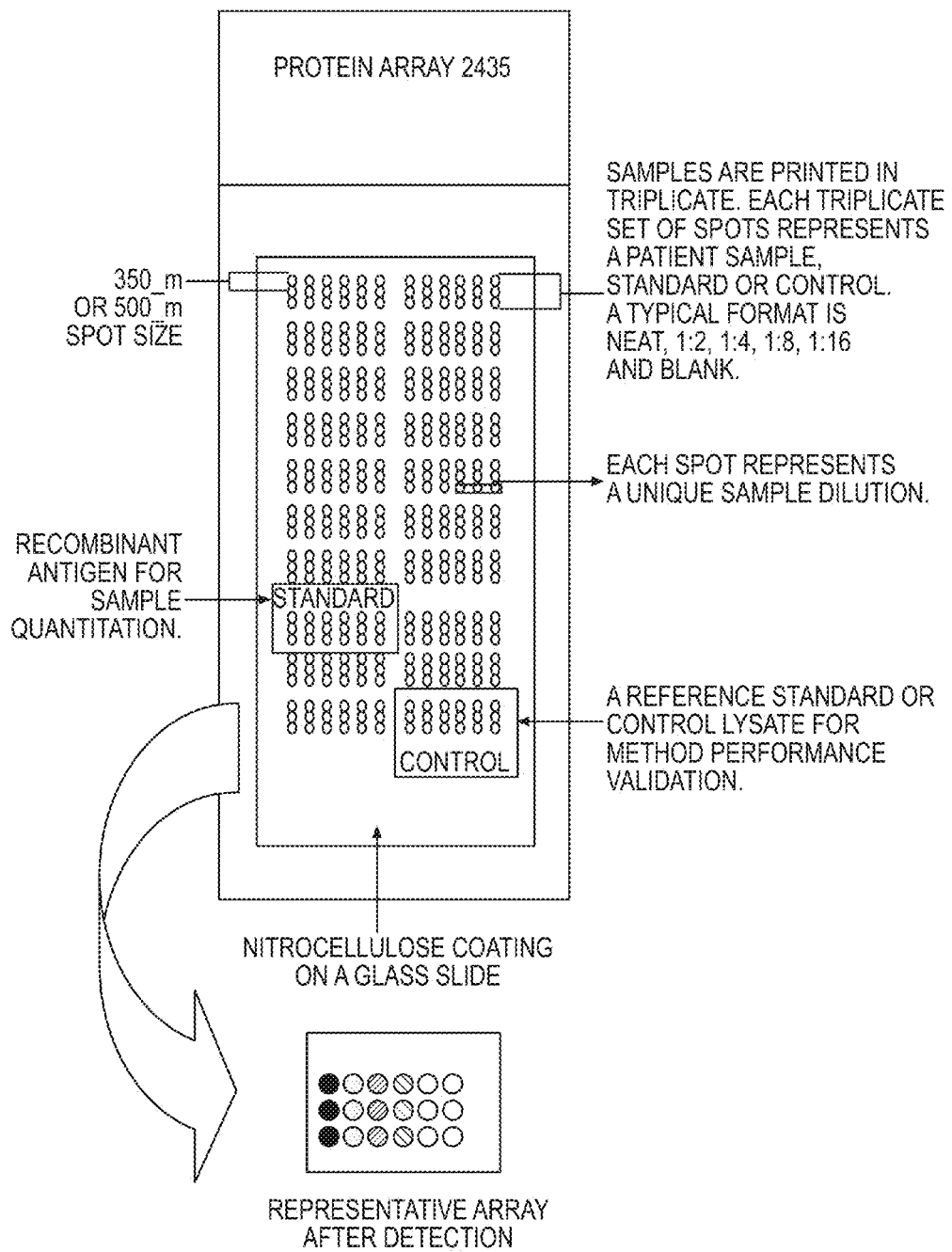
FIG. 4 is a diagram showing an idealized reverse phase array format.

Each patient or treatment sample may be arrayed on the RPA in a miniature dilution curve such that each analyte query will always be within the linear dynamic range of the assay (FIG. 3). Moreover, as the dilution curve contains a fixed amount of lysate at each dilution point, the curve also serves as a reproducibility assay (ie. a five point dilution curve that includes a series of 1:2 dilutions also serves as a quintiplicate run of the same sample on the array). Optimally, each point in the dilution curve is applied at random, but known points on the array, to eliminate bias caused by substratum heterogeneity. Dilution sets of pooled lysates, and recombinant antigens or phospho-peptides may be printed on the same arrays to achieve parallel calibration and quality control. Such internal reference standards serve to normalize signal intensities, provide intra array performance, and allow for comparison across experiments and conditions (FIG. 4). As shown in FIG. 4, triplicate samples are printed in dilution curves representing undiluted, 1:2, 1:4, 1:8 and 1:16 dilutions. The sixth spot represents a negative control, consisting of extraction buffer without sample. Each set of triplicate spots represents a patient sample before or after treatment, or microdissected normal, premalignant or stromal tissue cells. A reference lysate or control lysate is printed on each array for monitroing assay performance. A recombinant antigen is printed on each array for comparative quantitation of patient samples. Altering spot size, and/or spot spacing may vary array capacity.

A variety of bioanalytical methods have been successfully used for protein microarrays (see, for example, Brazma et al., "Minimum information about a microarray experiment (MIAME)-toward standards for microarray data," *Nat Genet* 29: 365-371, 2001; Carlisle et al., "Development of a prostate cDNA microarray and statistical gene expression analysis package," *Mol Carcinog*, 28:12-22, 2000; Cutler, "Protein arrays: The current state-of-the-art," *Proteomics* 3: 3-18, 2003; Miller et al., "Antibody microarray profiling of human prostate cancer sera: Antibody screening and identification of potential biomarkers," *Proteomics* 3:56-63, 2003; and Sreekumar et al., "Profiling of cancer cells using protein microarrays: discovery of novel radiation-regulated proteins," *Cancer Res* 61:7585-7593, 2001). A specific bioanalytical protocol including pattern recognition that was developed using public software is outlined in FIG. 5. The example illustrated in this figures displays a cluster analysis of microdissected human breast cancer and normal breast epithelium (vertical axis) compared across the phosphorylation states of a series of proteins within the EGF-receptor family signal pathway (horizontal axis lower right). The data collection and analysis steps depicted are described below.

Figure 5:
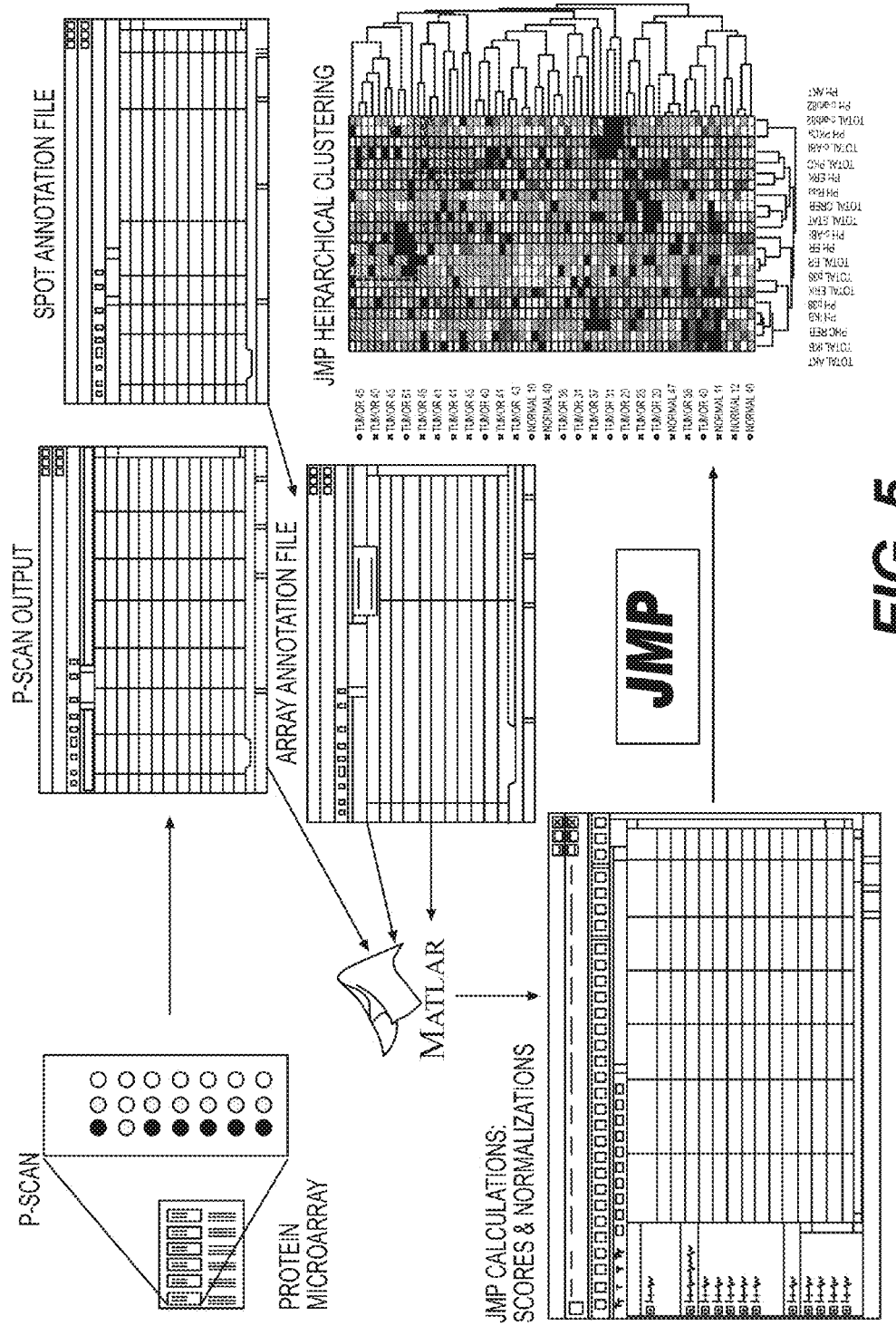
FIG. 5 is a diagram showing an embodiment of scanning and bioinformatic (pattern recognition) analysis of reverse phase arrays for protein signaling profiling.

With reference to FIG. 5, multiple RPAs, each analyzing a different phosphorylated protein, are scanned, spot intensities calculated, normalized, and the dilution curve collapsed to a single intensity value. This value is then assigned a relative colorized intensity value referenced to the other patient samples on the array. The data output is in the form suitable for traditional unsupervised and supervised learning (pattern recognition) systems. In this way, protein array data is displayed as traditional "heat maps" and can, for example, employ powerful Baysean clustering analysis for signal pathway profiling.

In the embodiment of FIG. 5, images are analyzed with P-SCAN (reference) yielding a raw intensity for each spot on each array. MATLAB scripts are then used to combine the intensity data for each array with annotations. The data are then imported into the JMP statistical package for further analysis and visualization. Since each sample appears in a dilution curve on the array, a binding score for each sample is determined with the following formula (assuming a three point dilution curve):

$$\text{Binding Score}=(P1-P3)/((P2+P3)/2+b),$$

where Pn is the spot intensity for the n-th point in the dilution.

The binding score attempts to reconstruct the specific binding (total minus non-specific), and express the result relative to the nonspecific binding in that assay. The bias term b, set to 50 in this example, increases the statistical reliability of the score by preventing very small denominator values. Other values for b of course may be used.

Empirically, the Binding Score usually demonstrates stability across different arrays, and is largely resistant to variations in overall slide staining intensity. However, a remaining trend in the scores across each slide, possibly arising from the small regional variance of the staining and washing procedure, may still yet exist. To correct for regional variability, local average scores for left-, middle- and right-portions of each array can be compared.

$$\text{Corrected Score}=\text{Binding Score}-\text{Local Average Score}$$

Correction for regional variance can be achieved by randomization of the sample placement on the array. "Empty" positions on the array may be purposely employed and can serve as a measure of the background precision attained with each antibody-stained array. With some antibodies, the spread of corrected score values for the "empty" spots may overlap that of the real negative samples. To effectively combine scores from different antibodies, the standard deviation of the empty spots can be used to standardize the Corrected Score as follows.

$$\text{Standardized Score}=\text{Corrected Score}-\text{Average(Corrected Score)}/(\text{std dev}(\text{"empty"}\text{ scores}))$$

The results from each antibody-labeled array in standardized-score units can then be combined into a single data matrix. The maximum Standard Score for each array can be interpreted as a signal-to-noise ratio. Two-way hierarchical clustering of samples (rows) and antibodies (columns) may then performed using Ward's method on the data matrix, and colored according to the standardized-score. Fisher's discriminant analysis can then be used to compare different phenotypes or treatment conditions.

EXAMPLE 3

Experimental Model for Individualized Combinatorial Therapy of EGFr Pathway Derangements The method for treating deranged signaling pathways based on targeting two or more different nodes (signaling proteins or events) in an aberrant signaling pathway was demonstrated in cell culture experiments. The epidermal growth factor receptor (EGFr) signaling pathway, which is a well-characterized pathway where interdependence is already known, was investigated. In cancer cells, the EGFr pathway is dominant and over-expressed in various types of cancers, and thus, has become a standard for evaluation of cancer therapy. Using reverse phase protein microarrays, the time course of protein phosphorylation events along the EGFr signaling pathway, following administration of EGF to EGFr positive colorectal carcinoma cells, was followed. The effects of multiple specific kinase inhibitors; each acting at individual interdependent steps in the EGF signal transduction process were compared. Specifically, the MEK-1 tyrosine kinase inhibitor, PD98059 [2-(2'-amino-3'-methoxyphenyl)-oxanaphthalen-4-one; see, for example, Reiners et al., *Mol. Pharmacol.*, 53: 438-45, 1998), and the EGFr tyrosine kinase inhibitor, AG1478 [4-(3-chloroanilino)-6,7-dimethoxyquinazoline; see, for example, Liu and Liang, *Acta. PHamacol. Sin.*, 23: 556-561, 2002], were applied to the cells, and the activity state of nodes along the EGF pathway, such as pEGFr, pERK, pMEK, pCREB, pAKT, pSTAT-3, and p38 was followed.

In these experiments, colon cancer cells, ATCC CCL-250, which over-express EGFr 25-75% of the time, were cultured. Once the cells had grown to approximately 80% confluency in 24 well plates, the media or drug solution was replaced with serum-free media. Impact of drug compounds on the pathway was evaluated by treating the cells with a drug compound or a combination of drug compounds for 30 minutes. Following treatment, approximately $5*10^5$ cells were stimulated (before the cells have remained on the serum-free media for over 24 hours) with ½ mL of EGF at 0.1 µg/mL concentration diluted in serum-free media. After each different elapsed time, the EGF solution was removed, and 100 µL of boiling lysis buffer (50% TPER, 48% SDS, & 2% β-mercapto-ethanol) was added. Cells were then scraped from the bottom surface of the wells using a pipet tip and placed into mini-centrifuge tubes. The lysates were then vortexed, boiled for 5 minutes, and centrifuged for 20 minutes at 14,000 rpm. The lysates were arrayed using the reverse phase microarray techniques described in Paweletz et al. (Paweletz et al., "Reverse phase protein microarrays which capture disease progression show activation of pro-survival pathways at the cancer invasion front," *Oncogene* 20: 1981-1989, 2001, incorporated by reference herein). In contrast to forward-phase protein arrays that immobilize the probe, the reverse phase protein array immobilizes the whole repertoire of patient proteins (e.g. by a nitrocellulose substrate) that represent the state of individual tissue cell populations. Probes are then applied to the immobilized proteins. Staining the arrays with antibodies to the phosphorylated signaling protein, which are denoted as the activated state of the node, and antibodies that bind to both the phosphorylated and unphosphorylated signaling protein, denoting the total concentration of the protein, for individual nodes in the pathway, reveals the impact of the stimulation and drug compounds on the activity state of various nodes along the pathway.

Figure 6A:
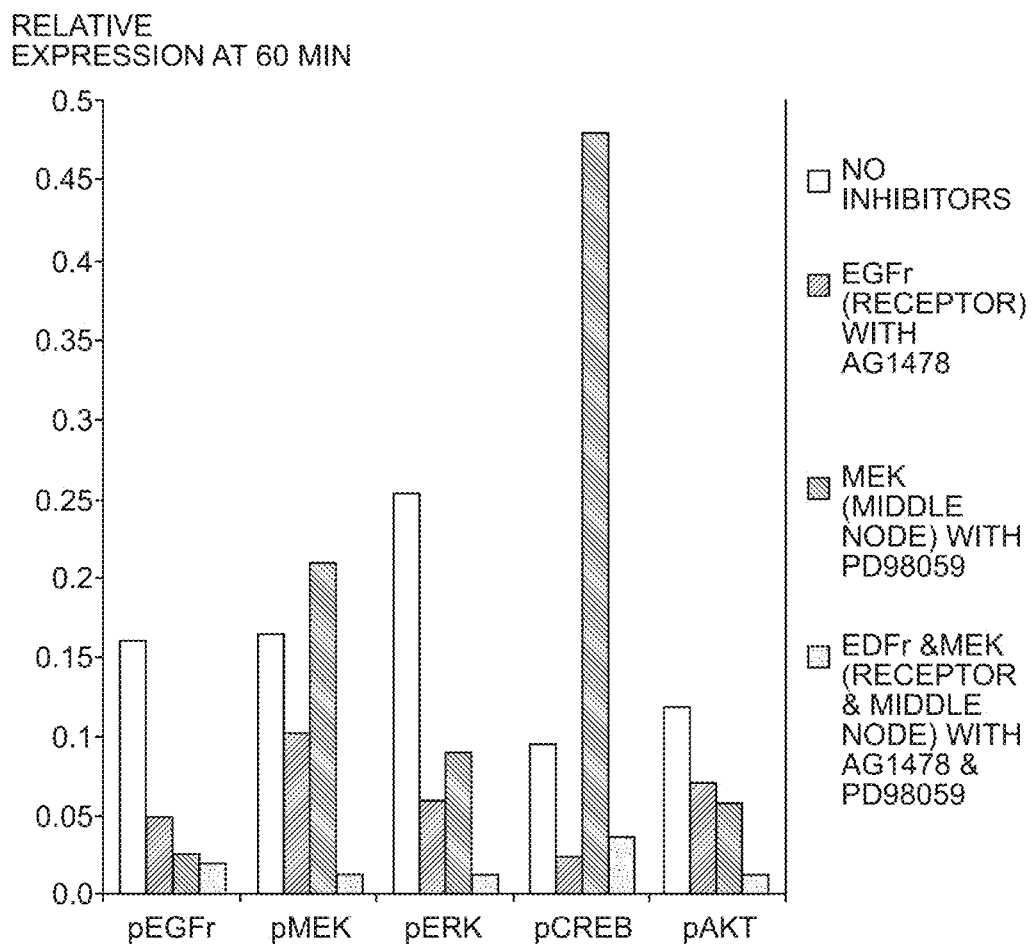
FIG. 6A is a bar graph showing the effect of treatment at particular nodes in the EGFr pathway on the activity levels of several components of the EGFr pathway, which is illustrated in FIG. 6B.
Figure 6B:
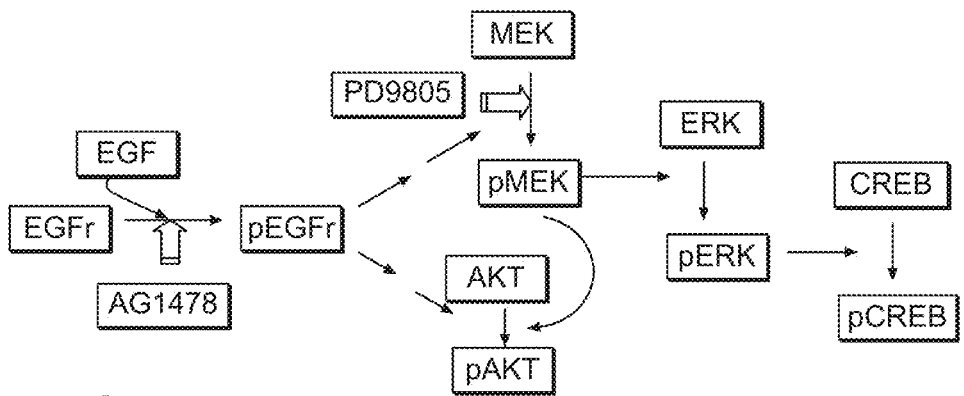

The results for the activity state of the various nodes along the EGFr signaling pathway are shown in FIG. 6A, where the activity state is expressed as the relative amounts of the phophorylated signaling proteins (phophorylated/total). A diagram showing the EGFr signal pathway and the signaling events targeted by the drug compounds is shown in FIG. 6B. Here, the EGFr signal pathway activation inhibition experiments reveal that a combination of inhibitors has a greater effect than any inhibitor administered alone evaluated at any node along the pathway. Also, these experiments display how the tyrosine kinase inhibitor has different impacts on different nodes depending on their location within the pathway. The impact of the MEK tyrosine kinase inhibitor PD98059 is expressed through diminishing the activation of the next node along the pathway, ERK. Through the relative expression of CREB, we see how using the MEK inhibitor alone causes shunting through this node (a result that also demonstrates that therapies directed to diseases such as Alzheimer's which are characterized by diminished activity at particular nodes, rather than hyperactivity, may be selected according to the disclosed methods). This shunting via the CREB node is not seen with either the EGFr inhibitor AG1478 or a combination of the MEK and EGFr inhibitors. The relative expression of the AKT node exemplifies the impact on a branch of the pathway that is not directly inhibited by the drug compounds, yet is interconnected. As a control, the impact of various treatments on a node (STAT), not associated with the EGF signaling pathway, was investigated and revealed that the treatments had no influence on the non-associated, and non-interconnected node (data not shown).

Figure 7:
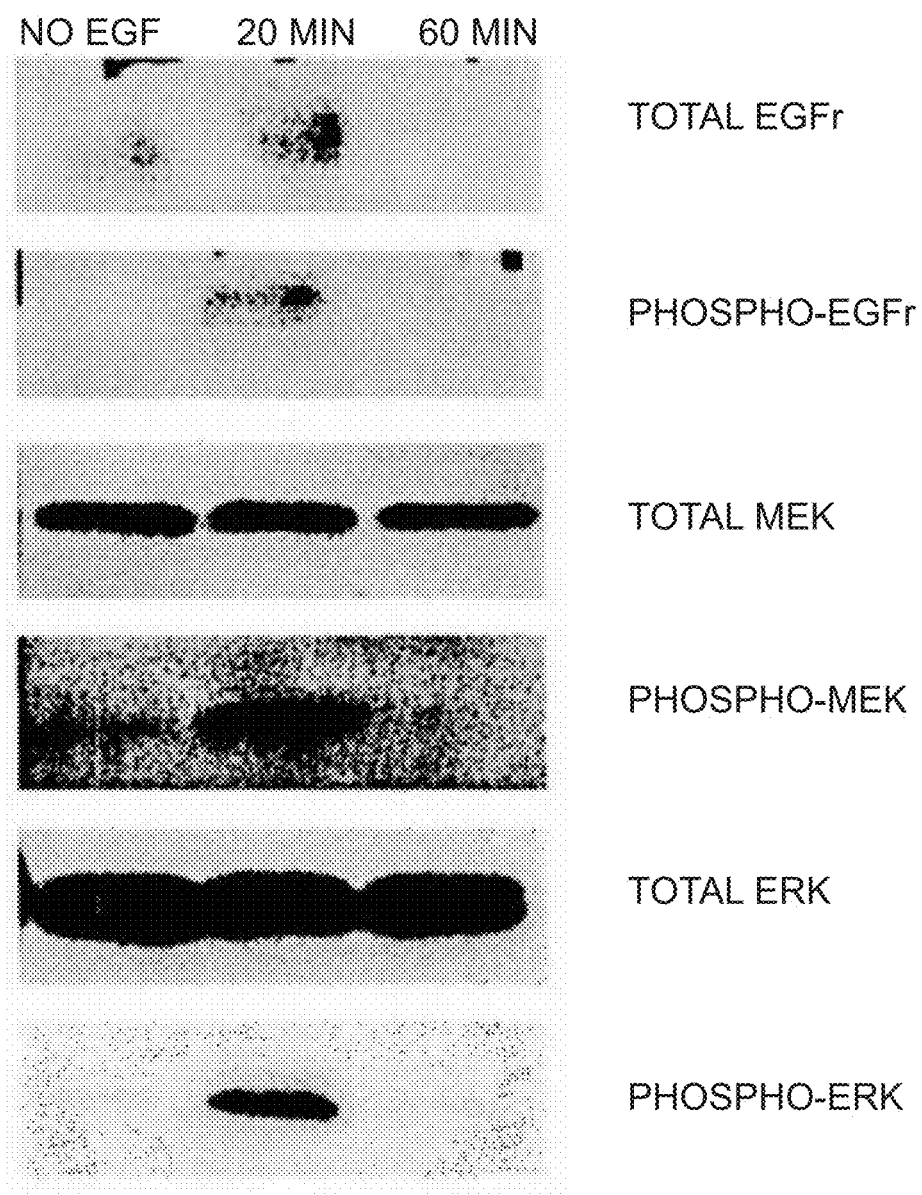
FIG. 7 is an image showing a representative Western blot used to validate a phospho-specific antibody for use in the disclosed methods.

FIG. 7 is a western blot demonstrating (validating) the specificity of two of the antibodies used to stain the reverse phase arrays and generate the graph of FIG. 6A. The phospho-antibodies bind to the phosphorylated, or activated, form of the protein. The other antibody binds to and is used to determine the total amount of the protein in the sample. Using the values from these two antibodies, the relative activation of that proteins may be calculated as the ratio of phosphorylated protein to total protein.

EXAMPLE 4

Figure 8:
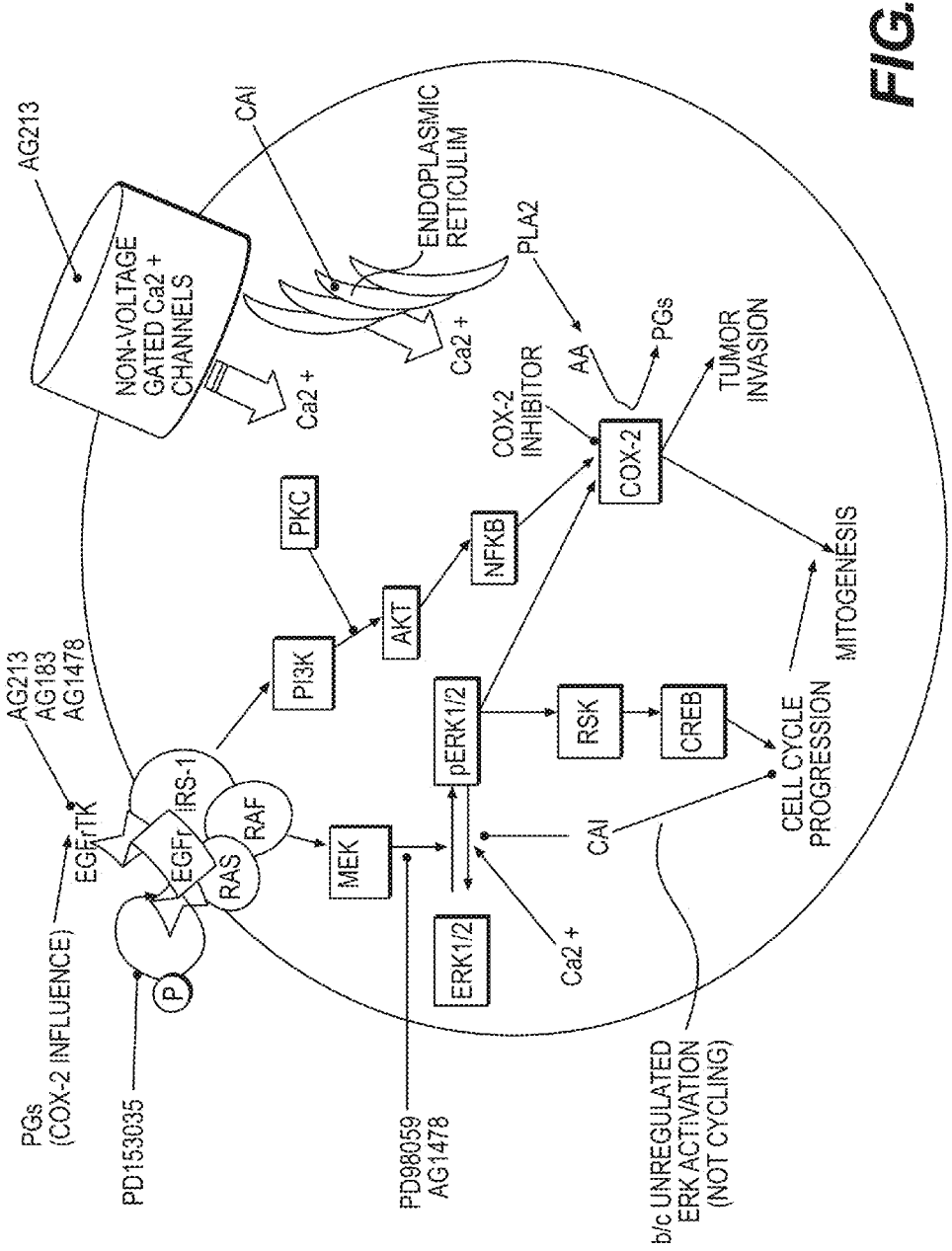
FIG. 8 is a diagram showing a protein signaling network and the site of action of several therapeutic agents directed to interconnected network components.

Identification of a Synergistic Therapeutic Combination by Protein Array Screening and Screening Using the Cellular Response of Interconnected Pathways in a Protein Network This example demonstrates synergistic effects of targeting interconnected pathways with a common cellular response, on that cellular response. Proteomic microarray analysis of biopsied human breast cancer samples were conducted. The samples were from subjects that were untreated, and from patients before and after experimental therapy with Herceptin, which inhibits the EGF class of pathways (FIG. 8). In these studies, enhanced activity of the AKT/COX-2 arm of the EGFr signal transduction pathway was observed. In particular, downregulation of pPKC-α and an upregulation of pAKT were observed (array data not shown). Using this information, a combination of a COX-2 Inhibitor and carboxyamidotriazole (CaI), a non-voltage gated channel calcium inhibitor, was selected as a candidate synergistic combination to target two of the pathways that converge in a network of signaling pathways that leads to tumor invasion (see FIG. 8). Additional potential targets along the pathways that converge at the cellular response of tumor invasion, and agents that can be used to target them also are shown in FIG. 8.

Figure 9:
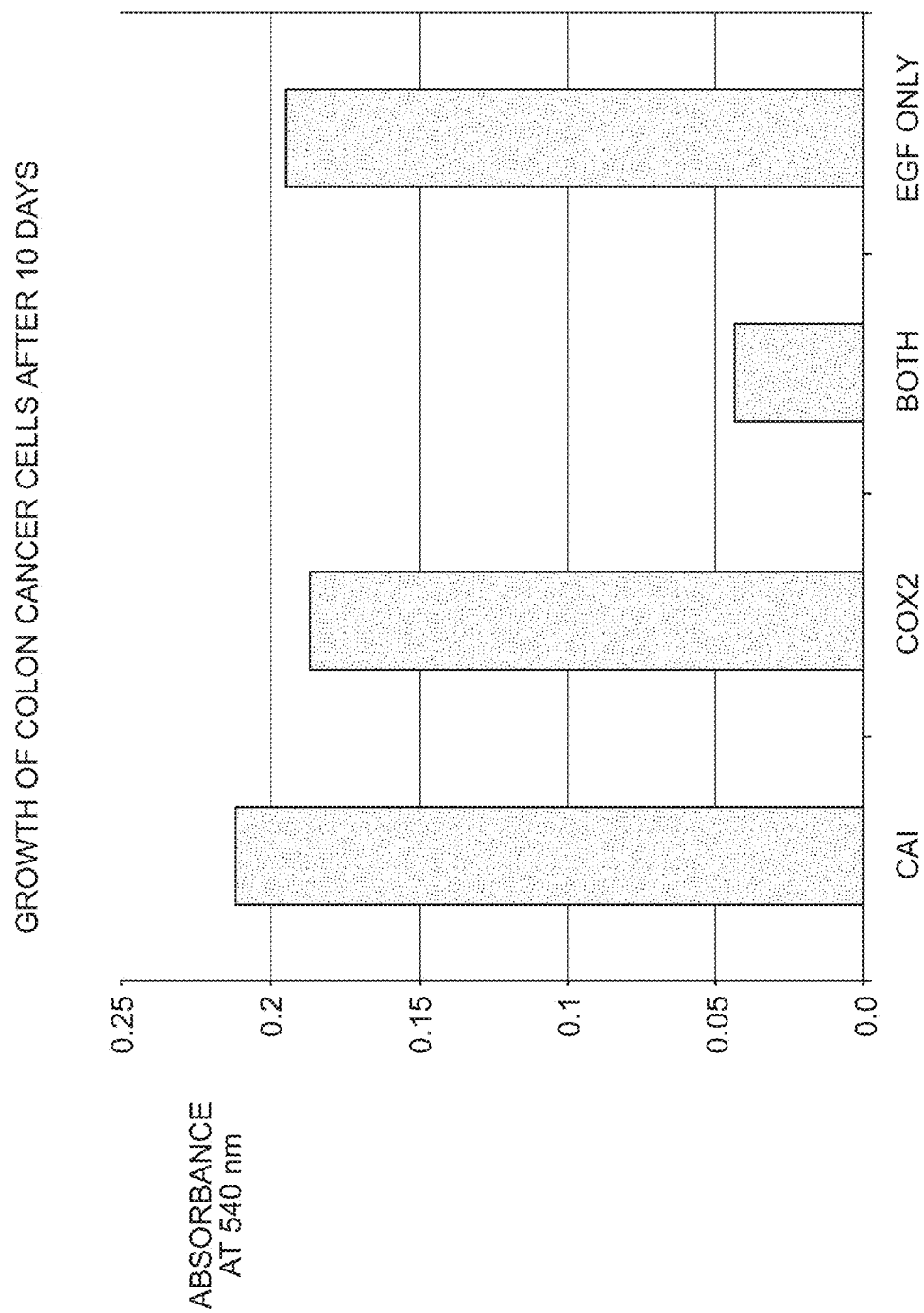
FIG. 9 is a bar graph comparing the effect of CaI and a COX-2 inhibitor, alone and in combination, on EGF stimulated growth of colon cancer cells.

The selected combination was assessed in a 10 day colony growth bioassay applied to EGF stimulated ATCC CCL-250 cancer cells. These cells are established to have augmented EGF receptors. The selected combination inhibited cell proliferation by 88%, using doses of the compounds that individually had no significanti-growth inhibition when used as single agent treatment (FIG. 9). This experiment demonstrates that multiple interdependent targets in a protein signaling network may be identified using protein-array data, and used to select a combination of drugs that can be applied to synergistically alter a cellular response under the control of the interconnected pathways. Perhaps most surprisingly, aberrations observed in a signaling pathway in one type of cell permitted selection of a combination of drugs that inhibited the same pathway in another type of cell.

EXAMPLE 5

Supra-Additive Anti-Proliferative Effects and Cell Signaling Changes in Human Cancer Cell Lines Treated with Carboxyamidotriazole and a Cyclooxygenase-II Inhibitor This example further demonstrates the effect of targeting components of interconnected signaling pathways that form a complex signal transduction network controlling a cellular response. Aberrant epidermal growth factor receptor (EGFR) signaling has been implicated in the progression of many human tumors. Ligand binding of EGFR leads to the activation of multiple signaling pathways that regulate processes that are important for a variety of cellular responses including tumor growth such as cell proliferation, survival, angiogenesis, invasion and metastasis. These pathways are exquisitely interrelated and can be targeted with the disclosed method; in addition, evidence suggests that crosstalk between EGFR pathways and other receptor pathways offer additional targets for the disclosed methods. For these reasons, targeting multiple nodes in the extensive network of EGFR signaling pathways is a rational approach to cancer treatment.

In particular, interconnected EGFr and nonvoltage-gated $Ca^{2+}$ channel pathways were targeted with a combination of carboxyamidotriazole (CAI) and the cyclooxygenase-II inhibitor LM-1685 (see, Palomer et al., *J. Med. Chem.*, 45: 1402-1411, 2002). The two agents, which disrupt growth-promoting signaling pathways at separate targets (nodes), were used, and synergistic effects were observed for combinations of the agents. Specifically, CAI targets NVGCCs and LM-1685 specifically targets the COX-II enzyme (as do phenylsulfonyl tricyclics such as Celecoxib and Rofecoxib). Antiproliferative effects and cell signaling changes induced by treatment with a combination of carboxyamidotriazole (CAI), a calcium influx inhibitor, and LM-1685, a cyclooxygenase-2 inhibitor, was assessed in an EGFR overexpressing cell line, CCL-250. Treatment with the combination produced supra-additive growth inhibition as compared with treatment with either agent alone. In addition, the CAI/LM-1685 combination induced cell signaling changes reflected by suppression of survival proteins and activation of apoptosis. These results suggest that CAI and LM-1685 create a combined blockade of the signaling network created by the functional interactions of EGFR, COX-2 and calcium, and demonstrate the use of multiple agents targeting different nodes to disrupt interrelated pathways in aberrant signaling networks.

Activation of the EGFR-related pathways was accomplished using 100 ng/ml recombinant EGF. Time course experiments indicate that receptor phosphorylation can be induced by PGE2 as well as the EGFR ligands, EGF and TGF-alpha. In addition, COX-2 protein expression is induced by treatment with PGE2. Together, these data support the existence of a forward feedback loop between EGFR, Cox-2 and PGE2.

Cancer cell lines (CCL-250, SK-OV-3, HeLa, HT-1080, PANC-1 and NCI-H23) were obtained from American Type Cell Collection (Manassas, Va.) and grown according to the enclosed instructions. Early passage murine embryonal fibroblasts (MEFs) (p3-6) were prepared from either LSL-K-ras$^{G12D}$ or p53$^{-/-}$, LSL-K-ras$^{G12D}$ embryos, and cre recombinase was added in-vitro to generate L-K-ras$^{G12D}$ MEFs as previously described (Tuveson et al.). MEFs were grown in 10% FCS/DMEM/25 mM Hepes.

The following antibodies yielded a single band on western blots and were affinity purified, rabbit polyclonal: (EGFR, MEK1/2, phospho-MEK1/2, ERK1/2, phospho-ERK1/2 (Thr202/Tyr204), AKT (Cell Signaling, Beverly, Mass.)); COX-2 and Cyclin D1 (Upstate Biotechnology, Lake Placid, N.Y.); phospho-AKT (Ser472/473/474) (BD Biosciences, San Jose, Calif.); and actin (Zymed, San Francisco, Calif.)). CAI was obtained from the NCI Chemotherapeutics Repository. COX-2 inhibitor and prostaglandin E2 were purchased from Calbiochem (San Diego, Calif.). Epidermal growth factor and 2× Tris-Glycine SDS Sample Buffer were purchased from Invitrogen (Carlsbad, Calif.). Tissue Protein Extraction Reagent was purchased from Pierce Biotechnology (Rockford, Ill.). The neutralizing anti-TGF-α,β-mercaptoethanol, and protease inhibitor cocktail were purchased from Sigma (St. Louis, Mo.).

For the time course assays, colon cancer cells were plated in 24-well plates (1×10e5 cells/well), grown to 80% confluency, and serum-starved for 24 hours. To assess EGFR activation, cells were treated with 100 ng/ml EGF, 10 μM PGE2, or 25 ng/ml TGF-α. Unstimulated cells were used as a control for basal activity. To assess TGF-inhibition, cells were pretreated with 100 ng/ml neutralizing TGF-α antibody for 1 hour before stimulation. To assess later cellular events, cells were grown in media containing 1% FBS with inhibitors added (5 μM CAI, 25 μM LM-1685, or 10 μM PD98059 with 5 μM CAI, 25 μM cox-2) or vehicle alone. To harvest cells at each timepoint, a number of cells were removed from wells by gentle scraping and suspended in 100 μL of heated SDS sample buffer (50% Tissue Protein Extraction Reagent, 48% 2× Tris-Glycine SDS Sample Buffer and 2% β-Mercaptoethanol) containing 10 μL of protease inhibitor cocktail per ml of lysate. Cells were immediately transferred to a chilled tube.

The reverse-phase protein array were as previously described (Paweletz et al). Briefly, cell lysates were subjected to one freeze/thaw cycle followed by vigorous vortexing to ensure complete liberation of proteins from the cytosol and the cell membrane. Immediately prior to spotting onto nitrocellulose slides, the samples were boiled for 5 minutes to ensure complete denaturation. Samples were spun at high speed in a microcentrifuge to remove any remaining cellular debris. Nanoliter amounts of the samples were arrayed onto nitrocellulose coated slides (Schleicher and Schuell Bioscience Inc., Keene, N.H.). Each sample was spotted nine times to form a "square" pattern consisting of three dilutions, left to right (neat, 1:2, 1:4), and three replicates of each dilution, top to bottom. Sample buffer alone was spotted as a negative control.

Slides were prepared for signal development by incubating for 10 minutes in a 10% solution of Mild Re-Blot Plus (Chemicon Intl, Temecula, Calif.) to expose antigenic sites embedded in the nitrocellulose. This was followed by two 5-minute washes in PBS and incubation in a casein-based blocking solution (Applied Biosystems, Foster City, Calif.) for at least 1 hour. Signal was developed using an automated staining system based on avidin/biotin and peroxidase methodologies (DakoCytomation, Carpinteria, Calif.). Staining is completed by a 5-minute incubation with 3,3'diaminobenzidine tetrahydrochloride (DAB) which results in a brown-colored precipitate at the antigen site. After signal development, slides were scanned on an Epson flatbed scanner at 1200 dpi. Scanned images (saved as an inverted grayscale TIFF file in Adobe Photoshop version 5.5) were analyzed with ImageQuant version 5.2 software (Molecular Dynamics, Amersham, UK). The spot intensity after background correction was proportional to the concentration of the target protein. Protein loading was normalized for phospho- and non-phospho-proteins with the total self-protein and β-actin, respectively (phospho-X/total X or X/actin).

For cell survival assays, six-welled plates were plated with 3×10e5 colon cancer cells per well. Cells were grown in appropriate media supplemented with 1% FBS. Inhibitors were added to the media at the $IC_{50}$ concentration, singly and in combination. (Each experimental condition was performed in triplicate). Media and inhibitors were replenished daily. At day 11 the cells were washed twice with PBS and stained with crystal violet stain (0.5% crystal violet in 20% methanol). Dye was eluted from each well using a solution of 50% sodium citrate (pH 4.2) and 50% absolute ethanol. Light absorbance of dye solutions was read at 540 nm on a spectrophotometer. The average O.D. for each condition was proportional to the net cell survival.

BrdU labeling and detection assays were purchased from Roche Applied Biosciences (Indianapolis, Ind.) and performed according to the manufacturer's instructions.

Cell cycle progression and apoptotis was determined by flow cytometric analysis. Cells were harvested by trypsinization, washed with PBS, and fixed with cold ethanol (70% v/v).

Immediately prior to analysis, the cells were centrifuged at high speed (4000 r.p.m.) and resuspended in PBS. Cell suspensions were incubated with RNAse (25 µg/10e6 cells) for 30 minutes at 37° C. After addition of 0.05% propidium iodide (PI), cells were analyzed for cell cycle distribution and DNA content by the Beckton FACStar flow cytometer. Quantitative analysis of apoptotic cells was performed by analyzing FACStar data with ModFit software.

Lysates that were analyzed by Western blot were evaluated for protein concentration with the BCA Protein Assay Kit (Pierce, Rockford, Ill.). Details of Western analyses are well known. Briefly, equal amounts of proteins were fractionated on 4-20% SDS-PAGE gels and transferred to PVDF membranes. After sequential incubations with primary antibodies and peroxidase-conjugated goat anti-rabbit antibodies (Tropix, Bedford, Mass.), signal was developed using an enhanced chemiluminescent staining system (Tropix, Bedford, Mass.). Protein loading was normalized for phospho- and nonphospho-proteins with the total self-protein and β-actin, respectively.

Statistical analysis of the data was performed using the Student's t-test to determine the statistical difference between various experimental and control groups. A p-value of <0.01 was considered significant.

Figure 10:
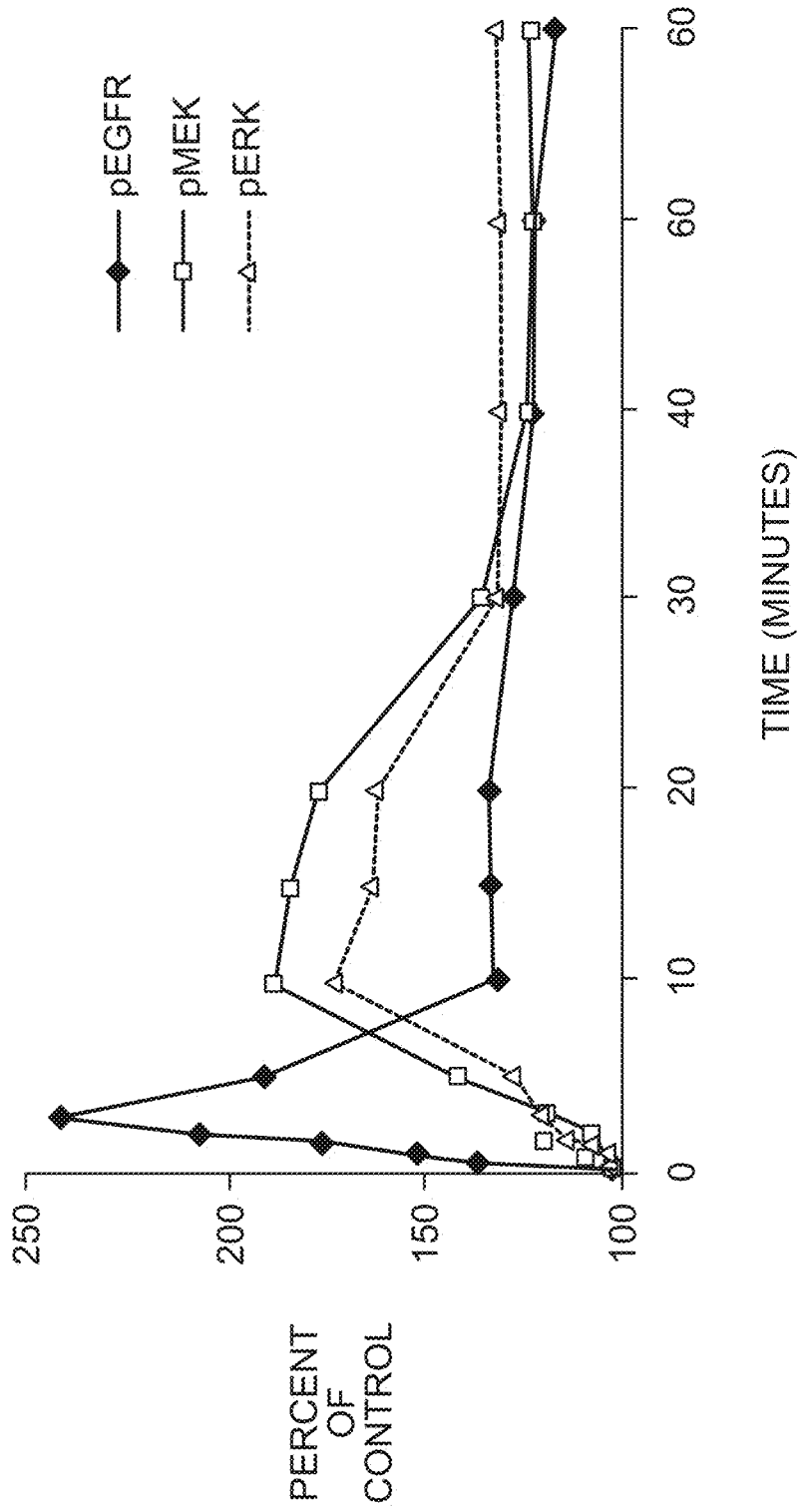
FIG. 10 is a graph showing the time course of activation of members of the EGFR pathway after stimulation of CCL-250 cells.

The ability of EGF to activate EGFR and downstream proteins in CCL-250 cells was assessed. Reverse phase protein microarrays of time course assay lysates of EGF-stimulated CCL-250 cells were prepared and hybridized with antibodies to components of the EGFR activated, mitogenic ERK 1/2 pathway. FIG. 10 illustrates the sequence, duration, and intensity of the signal generated by the activated pathway components. Cells are treated with 100 ng/ml EGF and assessed for phosphoproteins in the EGFR pathway. Activation is expressed as the relative intensity of stimulated cells compared with unstimulated cells on reverse phase protein microarray. The values shown represent the average of three separate experiments. EGFR activation (phosphorylation) generated a signal which reached maximum intensity within 5 minutes and quickly returned to near-basal levels. This was followed sequentially by broader, less intense peaks generated by phosphoMEK1/2 and phosphoERK1/2.

Figure 11:
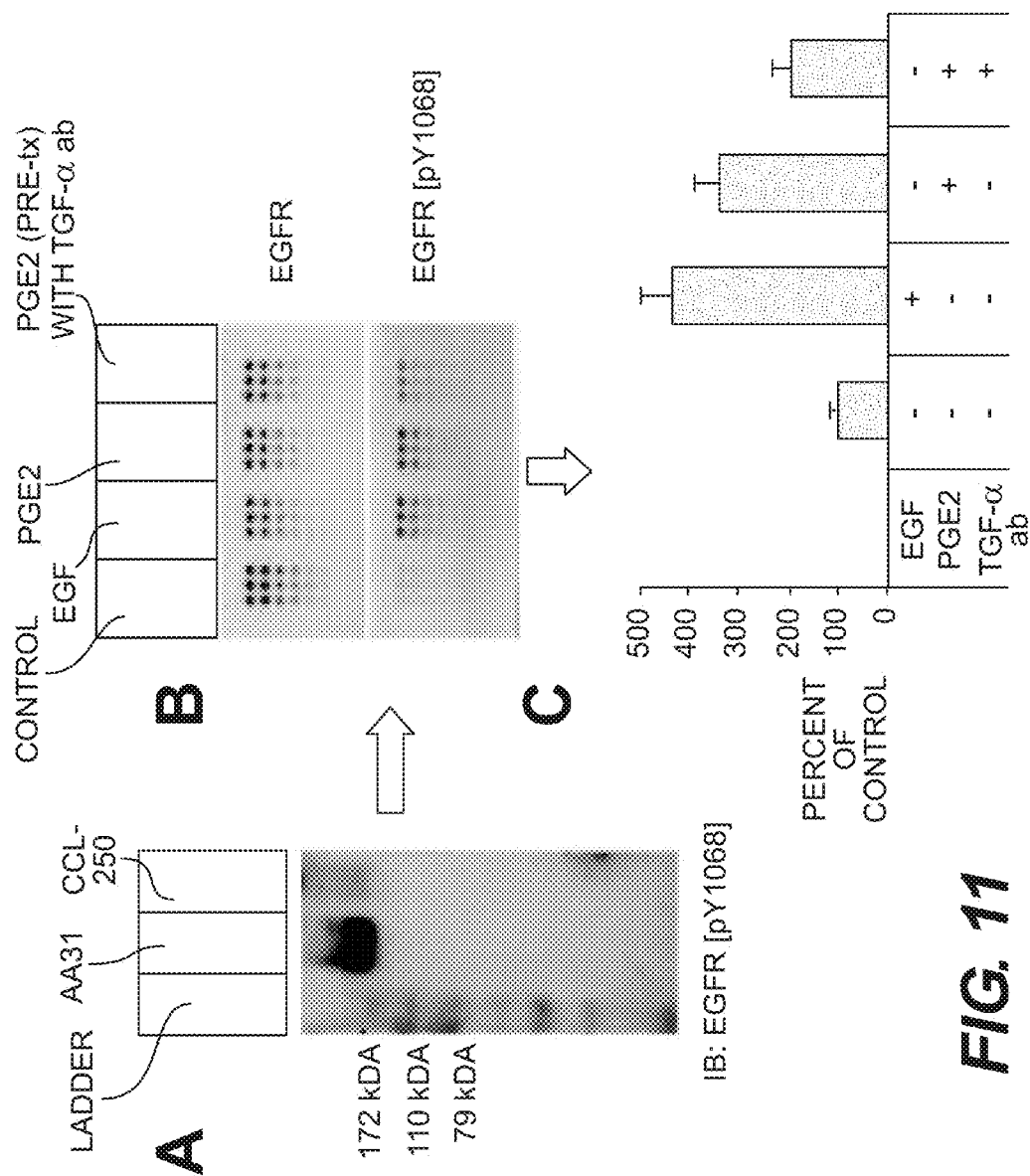
FIG. 11 (A, B, & C) shows the results of experiments that demonstrate the requirement of TGF-α for PGE2 transactivation of EGFR.

The ability of PGE2 to activate EGFR was determined, and the mechanism through which this occurs was demonstrated. Colon cancer cells pretreated with or without TGF-α inhibitor were stimulated with EGF or PGE2 and harvested at 5 minutes. After antibody validation by western blot (FIG. 11A), treated cell lysates were assayed for EGFR and phospho-EGFR protein by reverse phase protein array (FIG. 11B). The graph of FIG. 11C represents ratio of signal for EGFR: EGFR[pY1068]. The results show: 1) the ability of PGE2 to activate EGFR, and 2) the requirement of TGF-α for the activation of EGFR by PGE2. Values represent the mean+–SEM, p<0.01 (treated cells compared with control).

The effects of EGF and PGE2 on the expression of COX-2 protein also were assessed. After serum starvation, colon cancer cells grown in the presence of EGF or PGE2 were harvested every 24 hours over a 72 hour period and analyzed for COX-2 protein expression. Stimulation of cells with EGF or PGE2 induced increased expression of COX-2 protein as compared with a control as assessed by reverse phase protein array and Western blot (data not shown). Protein loading was controlled for by expressing COX-2 protein relative to β-actin.

Figure 12:
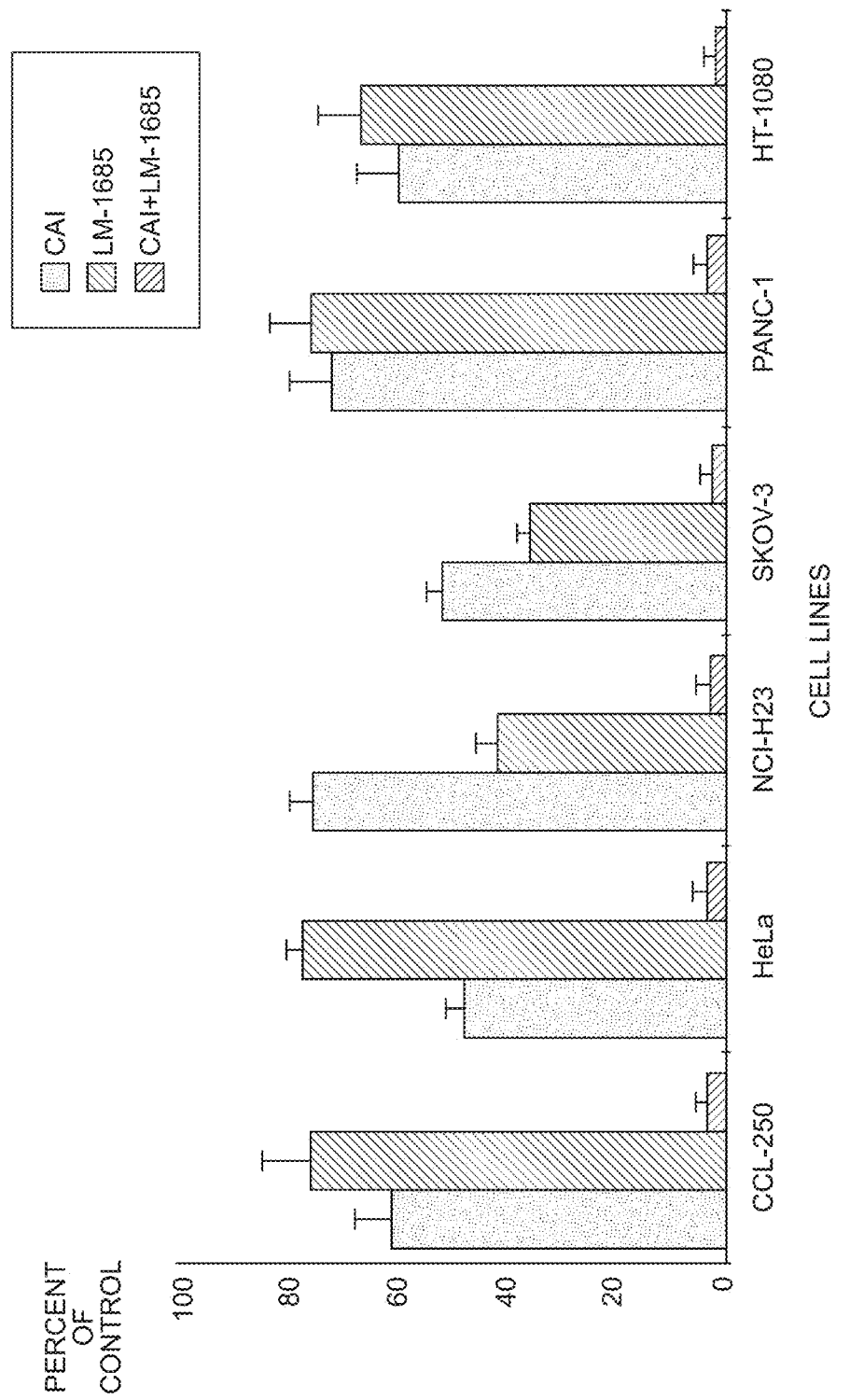
FIG. 12 is a bar graph showing the survival of CCL-250 cancer cells as measured by crystal violet dye uptake that were treated for 10 days with CAI, LM-1685, or combination of the two agents.

That a COX-2 inhibitor and carboxyamidotriazole (CAI) supra-additively inhibit growth of cultured cancer cells was demonstrated by crystal violet dye uptake cell survival assays. The assays were performed to assess the effect of COX-2 inhibitor and CAI alone, or in combination, on cultured cancer cells. Six of 6 cancer cell lines tested demonstrated profoundly decreased cell survival when treated with the COX-2 inhibitor/CAI combination as compared with cells treated with either drug alone. Cells treated with DMSO served as a vehicle control. On day 10, cells were stained with 0.5% crystal violet and dye was eluted with sodium citrate solution. Eluted dye was measured on a spectrophotometer at 540 nm. FIG. 12 shows net cell survival as measured by optical density of eluates. The CAI/LM-1685 combination shows a profound negative effect on cell survival. Cell survival assays of CCL-250 cells that included treatment with the MEK inhibitor PD98059 showed that the effect of the CAI/LM-1685 combinations was partially attenuated by the addition of the MEK inhibitor (data not shown).

Figure 13A:
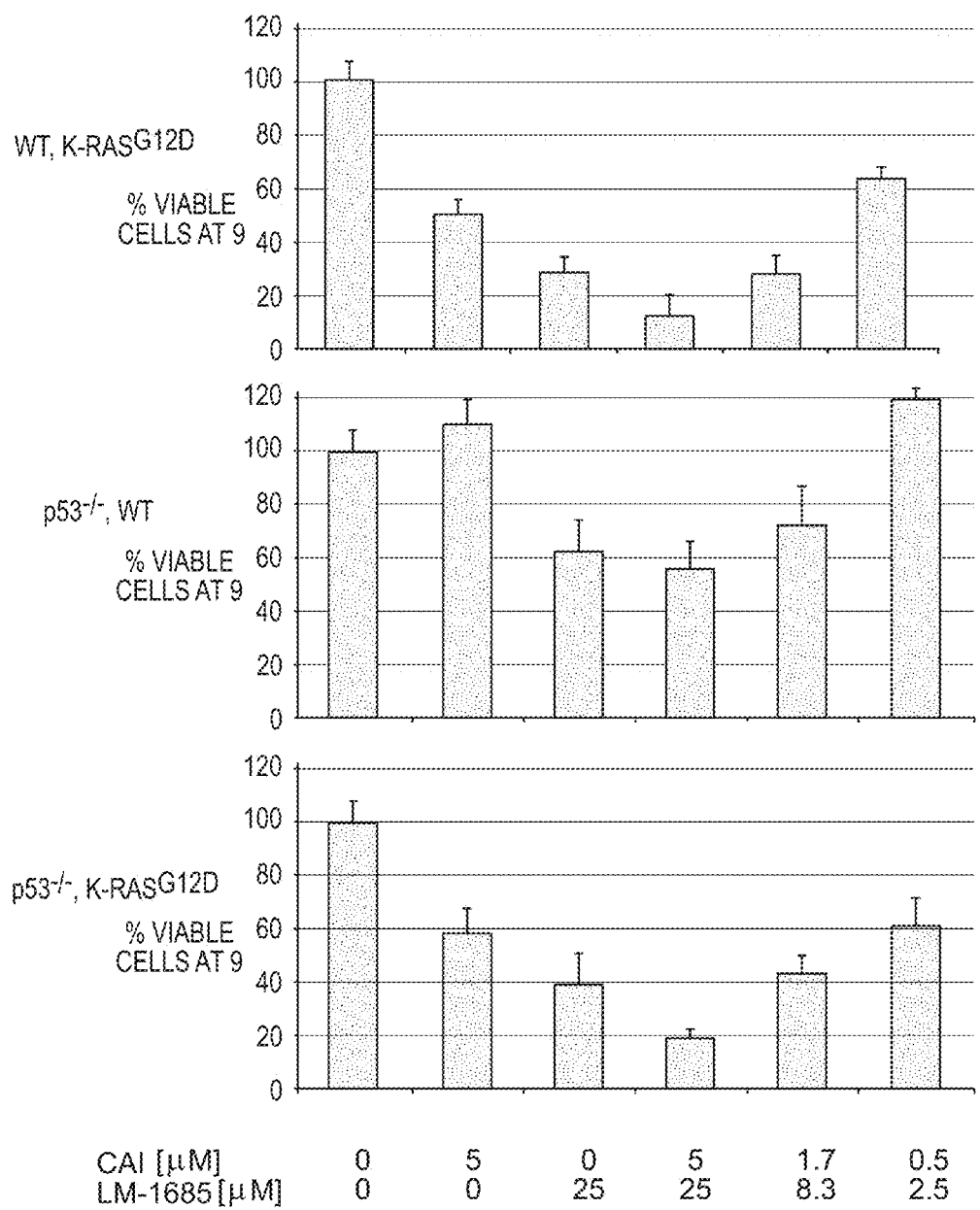
FIG. 13 (A & B) is a series of graphs showing the sensitivity of ras-transformed cells to a CAI/LM-1685 combination.
Figure 13B:
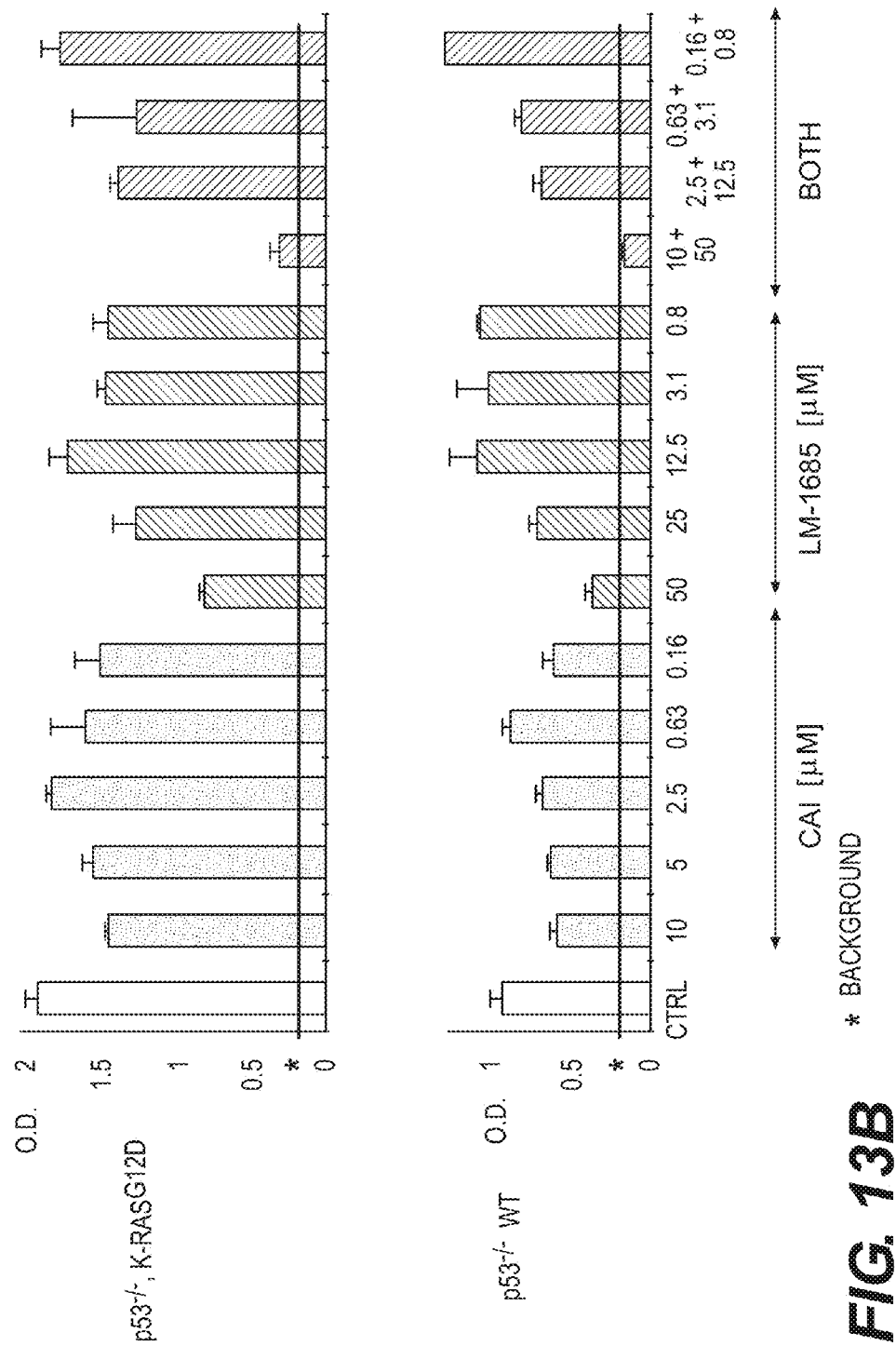

CAI and LM-1685 cooperate to inhibit proliferation and DNA synthesis in ras-transformed cells. Embryonal fibroblasts (MEFs) harboring an endogenous K-ras$^{G12D}$ allele (K-ras$^{G12D}$, 53$^{-/-}$, or both) were treated with varying concentrations of CAI, LM-1685, or both, and assessed for growth after 96 hours by trypan blue dye exclusion. Murine embryonal fibroblasts (MEFs) harboring an endogenous K-ras$^{G12D}$ allele (K-ras$^{G12D}$, 53$^{-/-}$, or both) were plated at an initial density of 6000 cells per well in 24 well plates. Drugs were added 12 hours later, and live cells were counted in triplicates 96 hours afterwards. Cell growth was plotted as the percentage of live treated cells in the total number of untreated cells (mean±s.e). Cells containing the K-ras$^{G12D}$ allele were 2-3 times more sensitive to the CAI/LM-1685 combination than wild-type MEFs (p53–/–), suggesting the combination targets ras-mediated signal transduction pathways (FIG. 13A). To assess DNA synthesis, transformed MEFs were treated with specified doses of CAI and LM-1685 (Control untreated cells designated as CTRL) for 48 hrs, and assayed for DNA incorporation of BrdU. As shown in FIG. 13B, CAI and LM-1685 cooperate to inhibit DNA synthesis. p53$^{-/-}$ MEFs harboring a silent or activated K-ras$^{G12D}$ mutation were treated with specified doses of CAI and LM-1685 (Control untreated cells designated as CTRL) for 48 hrs, and assayed for DNA incorporation of BrdU. Results are mean O.D. (±s.e.) of triplicate wells. Background O.D. (no BrdU added) is denoted by the horizontal line.

Figure 14A:
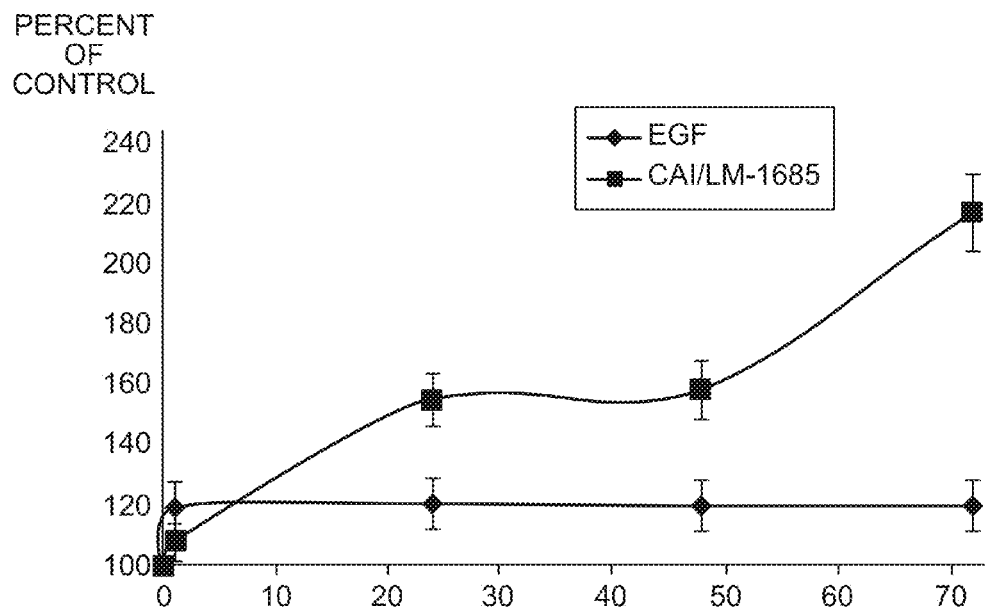
FIGS. 14A and B are graphs showing stimulation of ERK1/2 by a combination of CAI and LM-1685.
Figure 14B:
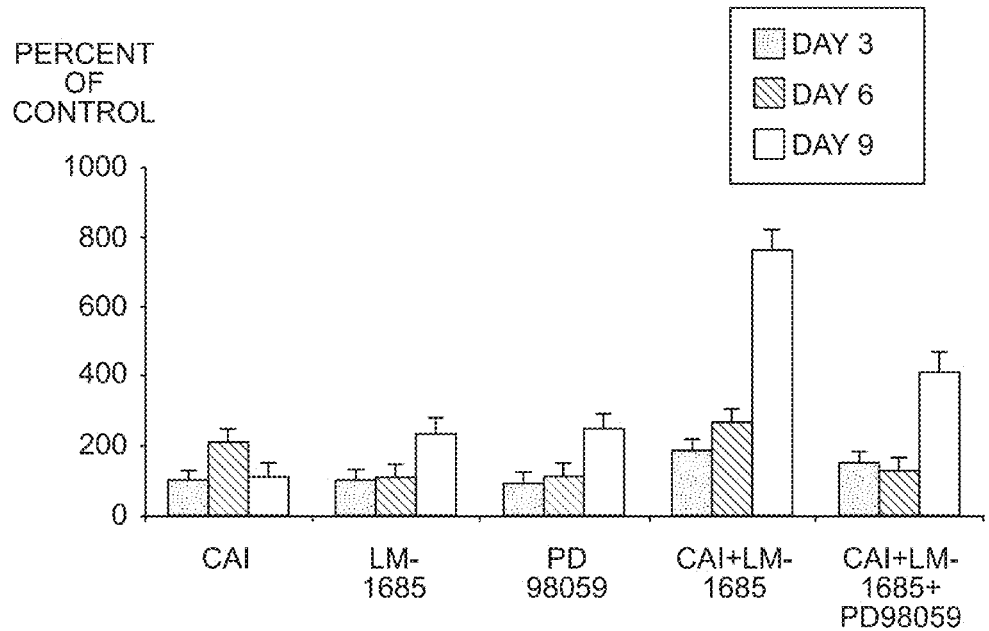

The CAI/LM-1685 combination also causes sustained activation of ERK1/2. A test of the ability of the CAI/LM-1685 inhibitor combination to suppress the mitogenic ERK1/2 pathway unexpectedly showed that the combination induced sustained activation of ERK1/2. Activation by EGF versus the CAI/LM-1685 combination was compared on reverse phase protein array. FIG. 14A shows activation of ERK1/2 over 72 hours in colon cancer cells grown in the presence of the CAI/LM-1685 combination relative to the control. Activation is expressed as the relative intensity of phosphorylated ERK in treated cells compared with untreated control cells after signal development, and values represent the mean+–SEM for 3 separate experiments. FIG. 14B shows activation of ERK1/2 in the presence of CAI, LM-1685, PD98059 or combinations of inhibitors. CCL-250 cells were treated with inhibitors and harvested every 3 days. Phosphorylated ERK was measured by reverse phase protein microarray, and values represent the mean+–SEM for 3 experiments, and p<0.01 (treated cells compared with control). FIG. 14B shows that the addition of the MEK inhibitor, PD98059, to the CAI/LM-1685 combination partially attenuates ERK activation.

Figure 15:
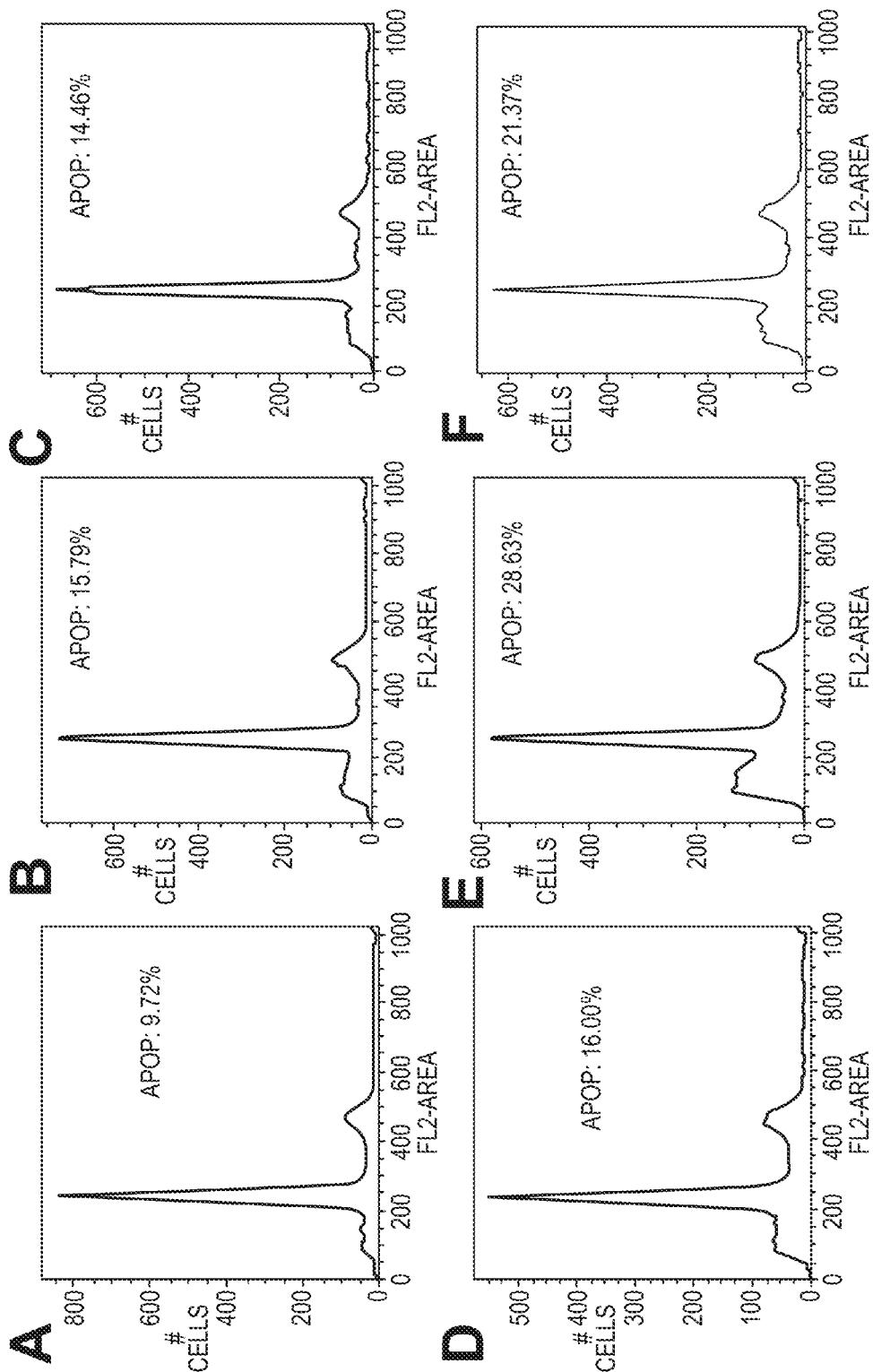
FIG. 15(A-F) are a series of fluorescence histograms of apoptotic cancer cells treated with various agents and combinations of agents. Treatment conditions were as follows: control (a), CA1 (b), LM-1685 (c), PD98059 (d), CAI+LM-1685(e), and (f) CAI+LM-1685+PD98059.
Figure 16A:
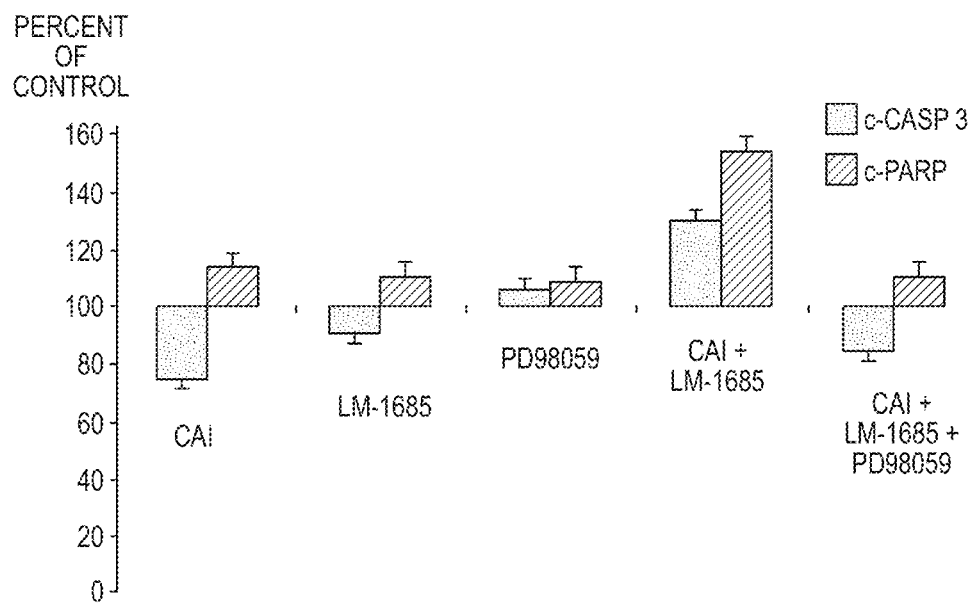
FIG. 16 (A & B) is pair of graphs showing expression levels of apoptisis proteins (c-casp 3 and c-PARP) and survival proteins (pAKT and cyclin D1) in cancer cells treated with CAI, LM-1685, PD98059 and combinations thereof.
Figure 16B:
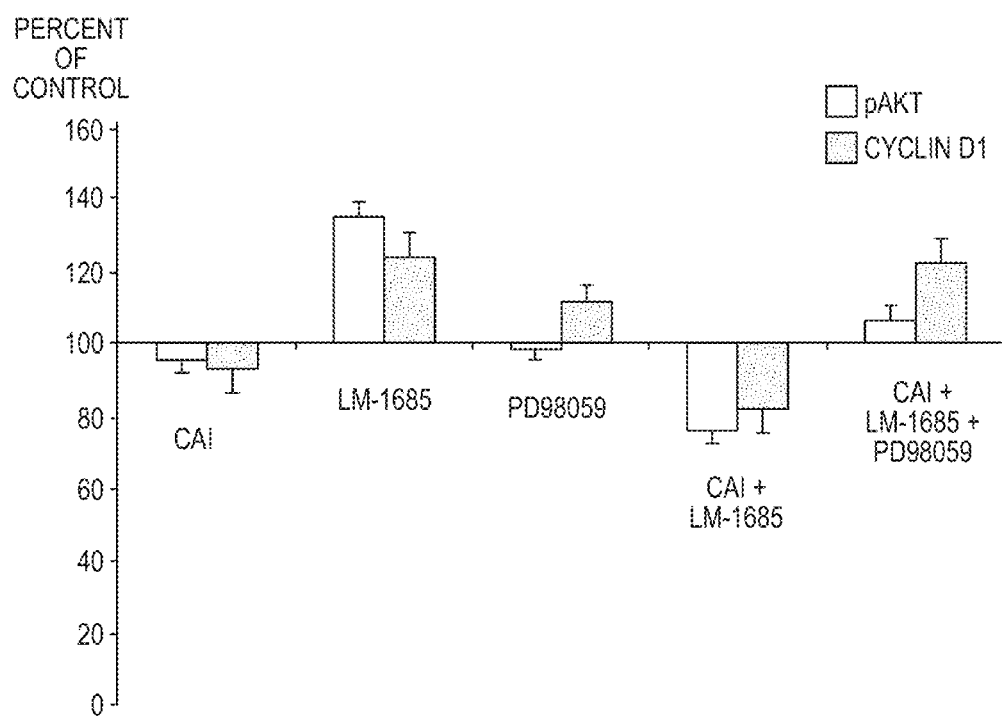

Cell cycle status of CAI/LM-1685 treated cells was also examined. Induction of apoptosis and growth arrest in treated cells were assessed by reverse phase protein array and flow cytometry. CCL-250 cells were treated for 3 days with inhibitor alone, the CAI/LM1685 combination, or the combination with PD98059 (MEK1 inhibitor). Fluorescence histograms (FIG. 15) of synchronous cells [control (a), CAI (b), LM-1685 (c), PD98059 (d), CAI+LM-1685(e), and CAI+ LM-1685+PD98059] and stained with propidium iodide showed a marked increase in apoptotic cells treated with the CAI/LM-1685 combination; whereas addition of a MEK inhibitor led to a slightly lower number of apoptotic cells. These results are representative of 3 experiments. The results of reverse phase protein array analysis of the cells are shown in FIG. 16. Assessment by reverse phase protein array showed significant induction of caspase 3 and PARP cleavage, which are hallmarks of apoptosis (FIG. 16A). Suppression of survival proteins in CAI/LM-1685 treated cells also was evident (FIG. 16B). PhosphoAKT and Cyclin D1 also were assessed with a reverse phase protein array. Cells were treated for 72 hours with CAI, LM-1685, PD98059, or a combination of the inhibitors.

In summary, the combination of a selective cox-2 inhibitor, LM-1685 and carboxyamidotriazole (CAI) has supra-additive antiproliferative effects and induces cell signaling changes resulting in growth arrest and induction of apoptosis in CCL-250 cells. These agents impact the EGFR pathways in multiple ways indicative of highly interconnected complex signal transduction networks. For example, the results show that TGF-α can activate EGFR in CCL-250 cells directly, or indirectly by TGF-α-dependent PGE2. Because cyclooxygenase-2 (COX-2) mediates the conversion of arachidonic acid to PGE2, our finding that PGE2 stimulates COX-2 expression as well as activates EGFR suggests the existence of a forward feedback loop between EGFR and COX-2. The disruption of this feedback loop by a selective COX-2 inhibitor (LM-1685) is one explanation for the effect of LM-1685 on the EGFR pathways. Overall, the observations indicate a connection between calcium pathways, Cox-2, and EGFR. By inhibiting the function of Cox-2 as well as the influx of calcium via non-voltage gated calcium channels (NVGCCs), multiple pathways influencing cancer progression can be blocked, and feedback loops can be disrupted. Transfected ras oncogenes have been shown to induce mitogenic and oncogenic properties in some cells. This altered behavior is likely due to changes in ras-mediated signal transduction pathways resulting in activation of downstream signaling proteins, including EGFR and the downstream ERKs. The result that ras-transformed cells show greater sensitivity to the CAI/LM-1685 combination than their corresponding wild-type cells suggests that these agents selectively target ras-mediated oncogenic signaling. Surprisingly, our experiments showed that the CAI/LM-1685 combination, rather than inhibiting the mitogenic MEK-ERK pathway, resulted in sustained activation of ERK. Addition of a MEK inhibitor reduced ERK activation. The prolonged activation of the MEK-ERK pathway appears to regulate apoptotic, rather than mitogenic events. Since CAI prevents the extracellular influx of calcium through NVGCCs and COX-2 inhibitors are thought to prevent release of calcium from the endoplasmic reticulum stores, together, these compounds could effect a total depletion of cytoplasmic calcium. Furthermore, since cytoplasmic phosphatases (PP2A, PTPase) help maintain a low basal activity of ERK but are inhibited by calcium depletion, an inactivation of phosphatases provides a possible mechanism for sustained activation of ERK in CCL-250 cells. Activation of Caspase 3 and suppression of Cyclin D1 in these cells suggests that sustained ERK activation leads to cell cycle arrest and apoptosis. The data presented in this example demonstrates that use of multiple agents directed against key nodes within these pathways may be used for the treatment of cancer, and in particular that a combination of a nonvoltage-gated calcium influx inhibitor and a selective cyclooxygenase-2 inhibitor has a potent antitumor effect by modulating downstream cytoplasmic signaling events in a cooperative and synergistic manner.

EXAMPLE 6

Mapping Molecular Networks: Kinase Substrate Protein Microarray Analysis of Human Breast Cancer Kinase substrate phosphorylation portraits derived from microdissected human breast cancer and normal epithelium revealed new pathway interconnections such as linkage of estrogen receptor activation (EGR pathway) with the c-kit pathway. Elevated phosphorylated PKCα was a discriminator for normal epithelium and significantly ($p<0.01$) correlated inversely with lymph node metastasis. Since these pathways are interconnected, combinations of agents that target specific nodes along these pathways may be used to correct signaling defects in human breast cancer.

A study set of human breast cancer and histologically normal epithelium was used for this analysis to determine functionality and feasibility of using the disclosed methods of signaling network profiling with clinical material, and using the profiles to select combinations of therapeutic agents that target multiple interdependent nodes within aberrant signaling pathways and networks. Two types of controls were analyzed: a) normal appearing mammary ducts adjacent to the cancer, and b) normal appearing mammary ductal epithelium microdissected from unaffected women undergoing reduction mammoplasty.

Frozen breast tumor tissues were collected at the Lombardi Cancer Center at the Georgetown University and Massachusetts General Hospital Cancer Center and Harvard Medical School. Reduction mammoplasty specimens were obtained from Northwestern University Hospital. The study set consisted of 45 primary human breast cancer cases, (6 of which had patient-matched normal and 1 which had both normal and premalignant cells available), and 9 healthy controls taken from patients undergoing breast reduction surgery. All neo-adjuvant treatment specimens were obtained from the UCSF Breast Cancer Center. The tissues were anonymized, and the histopathology of each case was confirmed by a pathologist before use in these studies. To ensure that surgical intervention and ischemia-induced signaling changes were minimized, tissue processing was performed such that tissue was frozen within 15 minutes after surgery. This time point compares favorably to a recent report where at a 1 hour post-surgery time point less than 0.6% of the 9000 genes analyzed showed any statistically significant ischemia induced changes.

8.0 µm frozen tissue sections were placed on uncoated glass slides and stored at −80° C. prior to use. Immediately before laser capture dissection, the sections were thawed and fixed in 70% ethanol for 5 sec, lightly stained with hematoxylin for 8 sec and dehydrated in 70, 95 and 100% ethanol for 1.5 min each followed by xylene for 2 min and then air-dried. The 70% ethanol and hematoxylin staining solutions were supplemented with Complete™ Mini protease inhibitor tablets (Roche Applied Science, Indianapolis, Ind.). Ovarian tumor epithelial cells or other relevant cell populations were microdissected with a PixCell II Laser Capture Microdissection system (Arcturus Engineering, Mountain View, Calif.). Approximately 5,000 LCM shots (20,000-25,000 cells) were microdissected for each case and stored on microdissection caps at −80° C. until solubilized. Additionally, multiple separate microdissections were performed on a subset of the patient samples to determine the variance in the levels of phosphorylated and total proteins measured in this analysis within a given patient sample. Endogenous protein phosphatase activity was reduced by incorporation of freshly prepared sodium orthovanadate (1 mM) and sodium molybdate (1 mM) into the staining baths for tissue processing. To ensure that surgical intervention and ischemia-induced signaling changes were minimized, tissue processing was performed such that tissue was frozen within 15 minutes after surgery.

Microdissected cells were lysed directly from the microdissection caps into 50 μL of lysis buffer containing a 1:1 mixture of 2× Tris-Glycine SDS Sample buffer (Invitrogen, Carlsbad, Calif.) and Tissue Protein Extraction Reagent (Pierce, Rockford, Ill.) plus 2.5% 2-mercaptoethanol (Sigma, St. Louis, Mo.) for 30 min at 75° C. The samples were boiled for 8 min, centrifuged briefly and stored at 4° C. Immediately prior to arraying, lysates were loaded into a 384-well plate and serially diluted with lysis buffer into a 4-point curve (neat, 1:3, 1:9, buffer alone). The arrays were constructed using a protocol detailed in Liotta et al. (Liotta et al., Protein microarrays: meeting analytical challenges for clinical applications," *Cancer Cell*, 3: 317-25, 2003, incorporated by reference herein) from a lysate of 25,000 cells (approximately 5000 discreet laser shots) in a total final volume of 50 μL. Approximately 60 mL of each sample was spotted onto nitrocellulose-coated glass slides (Schleicher and Schuell Bioscience, Keene, N.H.) with a GMS 417 microarrayer (Affymetrix, Santa Clara, Calif.). Slides were stored dessicated at −20° C. For estimation of total protein amounts, an aliquot of each lysate was run on Western blot and stained with anti beta actin antibody (Sigma, St Louis, Mo.). One day prior to antibody staining, the lysate arrays were treated with mild Reblot™ antibody stripping solution (Chemicon, Temecula, Calif.) for 15 min at room temperature, washed 2×5 min in PBS, and then incubated overnight in blocking solution (1 g I-block (Tropix, Bedford, Mass.), 0.1% Tween-20 in 500 mL PBS) at 4° C. with constant rocking.

To perform Western blotting, a 10 μL aliquot of the 50 μL lysate from each sample was denatured at 100° C. for five minutes and electrophoresed on 4-20% tris-glycine polyacrylamide gel electrophoresis (PAGE) (Novex, San Diego, Calif.) at a constant potential of 200 volts for 60 minutes. Standard Western blotting onto Immobilon-P (Millipore, Bedford, Mass.) PVDF membranes was performed at 15 volts held constant for 90 minutes. The resulting membranes were probed with the phospho-specific and total protein antibodies used in the microarray staining, as well as for actin. The probed signal was detected by chemiluminescence using Kodak Biomax MR film and the film scanned on a UMAX Powerlook III scanner utilizing Magicscan software (Dallas Tex.). The actin band was quantitated using Image Quant software v5.2 (Molecular Dynamics, Sunnyvale, Calif.), and all lysates volumes were then subsequently adjusted to ensure that each sample contained the same approximate total protein concentration.

A separate array was constructed and consisted of LCM generated lysates from 17 primary breast cancer specimens taken from a neoadjuvant trial of serial imaging to track response to chemotherapy consisting of 3 months of an anthracycline based regimen or 3 months each of an anthracycline plus taxane. These tumors represent a subset of study patients who had residual tumor after chemotherapy and gave consent for tumor banking. For these 17 patients, intermediate outcome measures such as residual tumor and lymph node status as well as short term disease free survival were known.

Blocked arrays were stained with antibodies on an automated slide stainer (Dakocytomation, Carpinteria, Calif.) using the Catalyzed Signal Amplification System kit according to the manufacturer's recommendation (CSA; Dako Cytomation). Briefly, endogenous biotin was blocked for 10 min using the biotin blocking kit (Dako Cytomation), followed by application of protein block for 5 min; primary antibodies were diluted in antibody diluent and incubated on slides for 30 min and biotinylated secondary antibodies were incubated for 15 min. Signal amplification involved incubation with a streptavidin-biotin-peroxidase complex provided in the CSA kit for 15 min, and amplification reagent, (biotinyl-tyramide/hydrogen peroxide, streptavidin-peroxidase) for 15 min each. Development was completed using diaminobenzadine/hydrogen peroxide as the chromogen/substrate. Slides were allowed to air dry following development.

Primary and secondary antibodies, dilutions used, and their sources were:
   a. rabbit anti-AKT 1:500 (Cell Signaling Technology, Beverly, Mass.)
   b. rabbit anti-phosphoAKT (S473) 1:500 (Cell Signaling Technology)
   c. rabbit anti-ERK1/2 1:200 (Cell Signaling Technology)
   d. rabbit anti-phosphoERK1/2 (T202/Y204) 1:1000 (Cell Signaling Technology)
   e. rabbit anti-phospho GSK3B (S9) 1:200 (Cell Signaling Technology)
   f. rabbit anti-phospho CREB (S133) 1:200 (Cell Signaling Technology)
   g. rabbit anti-CREB 1:100 (Cell Signaling Technology)
   h. rabbit anti-phosphop38 (Thr180/Tyr182) 1:200 (Cell Signaling Technology)
   i. rabbit anti-p38 1:100 (Cell Signaling Technology)
   j. rabbit anti-phosphoIKBκ.(S32).. 1:200 (Cell Signaling Technology)
   k. rabbit anti-IKMκ Cell Signaling Technology)
   l. rabbit anti-phopho c-Abl (Tyr 735) 1:200, (Upstate, Waltham, Mass.)
   m. rabbit anti-cAbl 1:200, (Cell Signaling Technology)
   n. rabbit anti-phospho c-erbB2 (Try 1248) 1:500, (Cell Signaling Technology)
   o. rabbit anti-c-erbB2 1:200, (Cell Signaling Technology)
   p. rabbit anti-phopho STAT1 (Tyr 701) 1:200, (Upstate)
   q. rabbit anti-STAT1 1:200, (Cell Signaling Technology)
   r. rabbit anti-phopho PKCα (S 657) 1:200, (Upstate)
   s. rabbit anti-PKCα 1:200, (Cell Signaling Technology)
   t. rabbit anti-phosphoER (S118) 1:200, (Cell Signaling Technology)
   u. rabbit anti-ER 1:200, (Cell Signaling Technology)
   v. rabbit anti-phospho FKHRL/FKHR 1:200, (Cell Signaling Technology)
   w. rabbit anti-phosphoRAS-GRF1 (S916), 1:200 (Cell Signaling Technology)
   x. rabbit anti-RAS-GRF1, 1:200 (Cell Signaling Technology)
   y. mouse anti-actin 1:500 (Sigma, Woodlands, Tex.)
   z. biotinlyated goat anti-rabbit IgG (H+L) 1:5000, (Vector Laboratories, Burlingame, Calif.)
   aa. biotinylated rabbit anti-mouse IgG 1:10 (DakoCytomation).

Antibody stained slides were scanned individually on a UMAX PowerLook III scanner at 600 dpi and saved as TIF files in Adobe Photoshop 6.0 (Adobe, San Jose, Calif.). The TIF images for antibody-stained slides and Sypro Ruby-stained slide images were analyzed with ImageQuant v5.2

(Molecular Dynamics) and Microsoft Excel 2000 software. The dilution curves were plotted to ensure analysis within the linear dynamic range. Scanned images were analyzed by P-SCAN, MATLAB and JMP, and clustering analysis also was performed according to the methods outlined in detail in Liotta et al., Protein microarrays: meeting analytical challenges for clinical applications," *Cancer Cell,* 3: 317-25, 2003.

A human colon cancer cell line (CCL250) with over-expressed c-erbB1 receptor levels was treated at various time points with and without 100 ng/ml recombinant EGF (Invitrogen, Carlsbad, Calif.). Prior to EGF stimulation cells were pretreated for 1 hour, with or without 10 uM of the MEK inhibitor PD98059 (Cell Signaling, Beverly, Mass.). Separate aliquots at a series of EGF post treatment time intervals were taken and cell lysates were prepared for kinase substrate array analysis.

Laser Capture Microdissection (LCM) was used to procure an enriched starting population of tumor cells, which is advantageous as every cell type may contain differences in their proteomic repetriore. Kinase substrate and signal pathway analysis, was performed with multiple reverse phase protein arrays containing immobilized cell lysates. Protein phosphorylation was detected using a set of antibodies that were validated for specificity and sensitivity using a subset of the LCM breast tissue using antibodies which a) recognize the protein only when it is phosphorylated on a specific tyrosine and/or threonine residue substrate, effectively providing a readout for a specific upstream kinase activity, and b) which recognize the protein regardless of phosphorylation state. The phosphorylation pattern attained from different discreet LCM cell populations in the same tissue specimen was reproducible. Variance was determined by measuring the relative intensity of each analyte endpoint within multiple independent LCM samples procured from the same tissue sample. A pooled lysate consisting of about 25,000 epithelial cells procured from different regions of the tissue specimen gave reproducible phosphorylation outcomes with coefficient of variance of less than 10% (data not shown).

Figure 17:
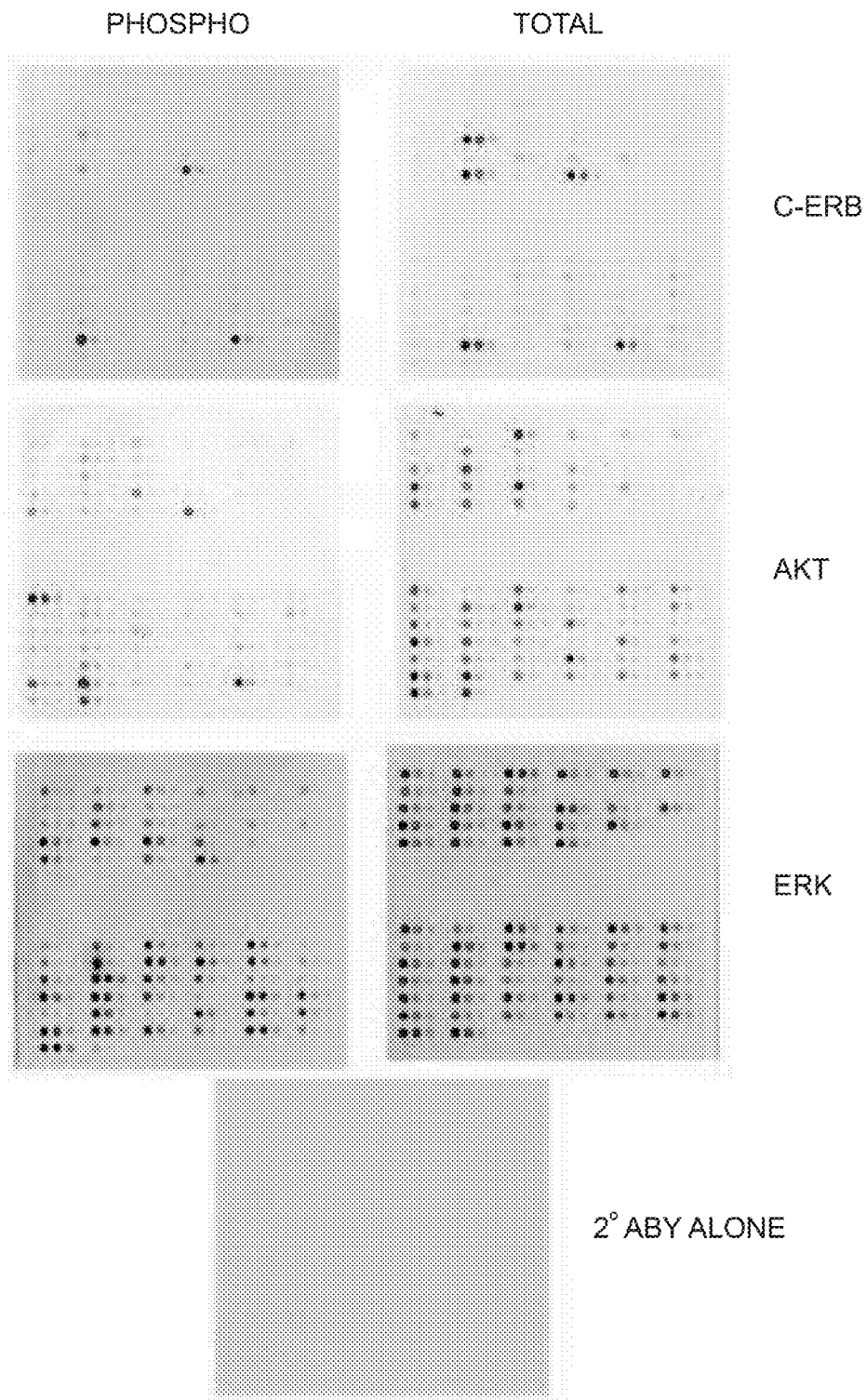
FIG. 17 is a series of photographs of reverse phase protein microarray analyses of laser capture microdissection samples obtained from a breast cancer study set.

Phosphorylation of the kinase substrates AKT, c-ErbB2, and ERK, which are components of the EGF signaling pathway known to be important in breast cancer, were analyzed by microarray analysis (FIG. 17). PI3 kinase dependent phosphorylation of specific residues of the AKT protein kinase has been shown to correlate with enzymatic activity of this critical pro-survival pathway mediator. Phosphorylation of ERK kinase by MEK 1 has been shown to correlate with enzymatic activity of this critical pro-growth pathway mediator. Both of these pathways, which also cross-talk substantially, can be controlled directly through the EGF receptor family activation and can be hyperactivated when c-erbB2 is overexpressed and heterodimerizes with other members of the EGF receptor family (e.g. c-erbB1). Only a small subset of breast cancer specimens in this study set had both high levels of phosphorylated c-erbB2 and total c-erbB2 receptor protein (FIG. 17). Over-expression of the c-erbB2 receptor correlated with its phosphorylation in most but not all of the patients, with 2 patient specimens containing high levels of the unactivated receptor (FIG. 17). Those patients with over-expressed but non-phosphorylated c-erbB2 also did not have high levels of phosphorylated AKT and ERK, indicating that receptor driven signaling was not apparent in those 2 samples. While those three individuals with over-expressed and phosphorylated c-erbB2 receptor also had concomitant phosphorylated AKT and ERK phosphorylation events, there were many subjects with high levels of phosphorylated AKT and/or ERK but without over-expressed c-erbB2 (FIG. 17). This type of event could occur if the signaling pathway was affected by aberrant kinase/phosphatase activity, which occurs downstream from the receptor such as through PI3 Kinase activation. Also shown in FIG. 17 is a separate array analyzed at the same time that was incubated with the secondary antibody alone as a background control (bottom)

Figure 18A:
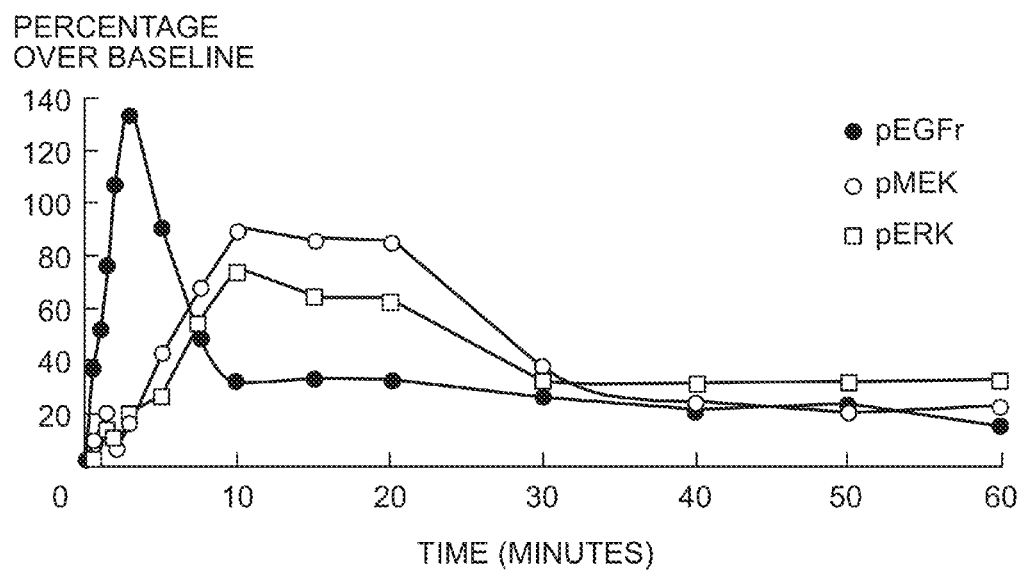
FIG. 18 (A & B) is a pair of graphs showing the time-course of activation of members of the ERK signaling pathway following stimulation of the pathway in the absence and presence of a specific MEK kinase inhibitor.
Figure 18B:
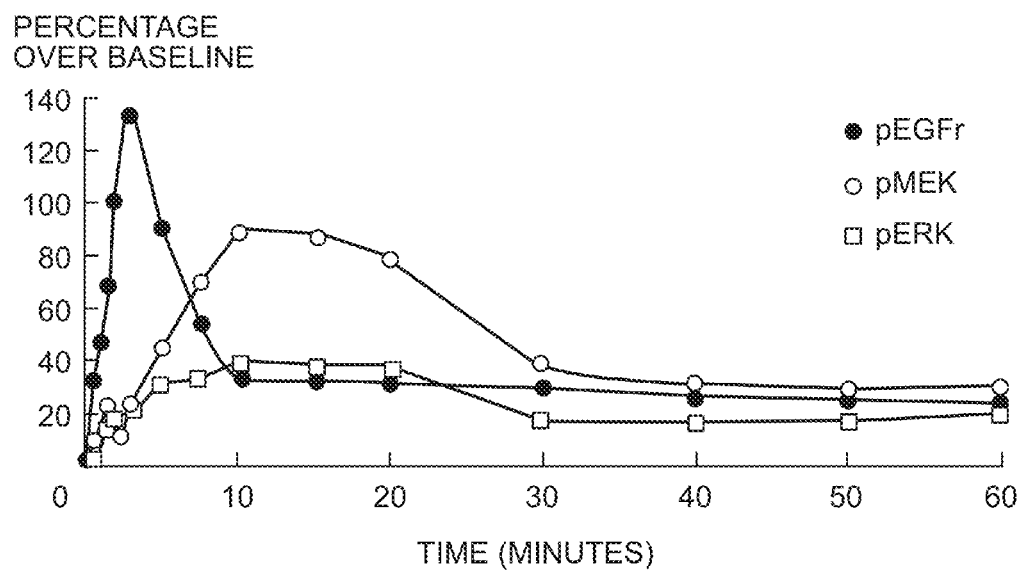

To determine if this technology can capture the time-course of linked kinase network events, a series of known connected phosphorylation substrates were analyzed: epidermal growth factor receptor (c-erbB1), MEK, and ERK kinases using a colon cancer cell line (CCL250) with over-expressed c-erbB1 receptor levels. Upon receptor-ligand binding, the EGF receptor becomes rapidly phosphorylated and downstream substrates (eg. MEK and ERK) of the cascade associate and become phosphorylated. When these events are analyzed by reverse phase array, both ERK and MEK phosphorylation show a coordinately linked kinetic profile which is expected since ERK is a direct substrate of MEK kinase (FIG. 18A). When the cells were pretreated with a specific MEK kinase inhibitor, as expected, only ERK phosphorylation was effected, thus showing the utility of analyzing the phosphorylation of the kinase substrate itself as a surrogate for the upstream kinase activity (FIG. 18B). Phosphorylation of kinase substrates is a transient event, as phosphatases promptly dephosphorylate the substrate as the cascade continues. Thus, at any point in time if two substrates are phosphorylated concurrently it is likely that they are linked together to some extent in an active pathway, such as seen with MEK and ERK kinase.

The ability of the protein array to portray network interconnection in human tissue specimens, where signaling events would be captured in a discreet snapshot in time, was demonstrated. Network analysis of expected kinase substrate cascades was performed on a set of patients with high and low levels of AKT phosphorylation. Glycogen synthase kinase 3 (GSK3) and the Forkhead protein family (FKHRL/FKRH), which are all well known AKT kinase substrates involved in glucose mobilization and energy metabolism as well as transcriptional regulation of pro-survival pathways. Concordance was observed between phosphorylation of AKT and the downstream kinase substrates GSK3 and FKHRL/FKHR, but not with other substrates such as ER and STAT1 (FIG. 19). Thus, it appears that closely linked events will show tight correlation of phosphorylation (activation) while those phosphorylation events that are not coordinated are likely not to be directly linked in a network. These considerations can then be used to select combinations of therapeutic agents targeting coordinated (interconnected) signaling aberrations.

Figure 20:
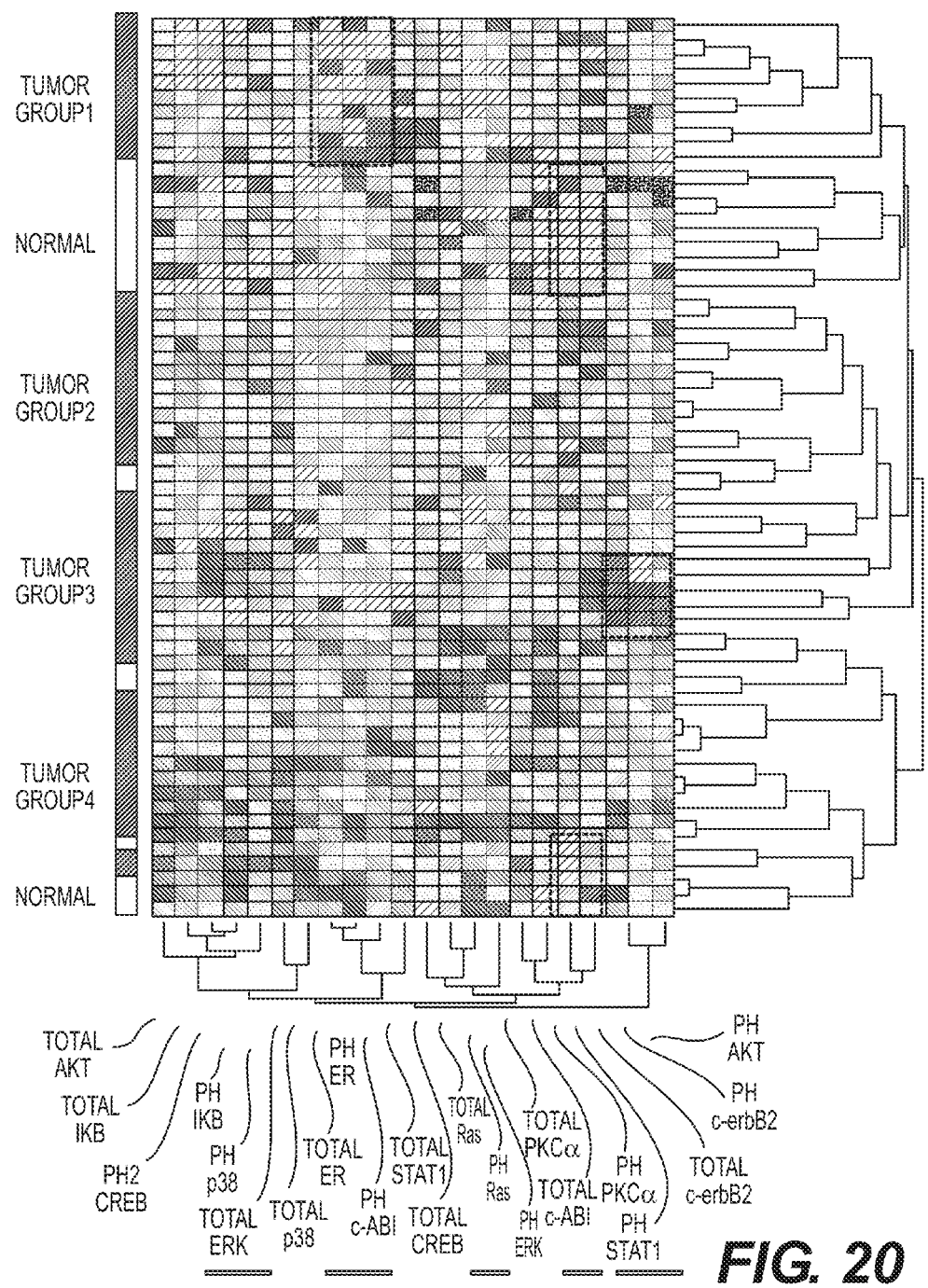
FIG. 20 shows the results of unsupervised cluster heat-map analysis of multiplexed kinase substrate endpoints, where the twenty-two endpoints (11 matched phospho-specific and total protein specific) of a 54 patient study set were analyzed by reverse phase protein micorarrays.

Since kinase interconnections can be detected by kinase substrate protein microarray analysis, an expanded suite of phosphorylation events were determined by microarray analysis and then subjected to pattern recognition with the goal of uncovering new network interconnections and targets that may be selected for treatment. FIG. 20 show the clustering results obtained using unsupervised Bayesian clustering methodology for each of 54 patients (45 cancer, 9 normal) as a heat map where relative protein levels are measured and shaded representing higher (light shade) or lower (dark shade) relative expression. For the phospho-specific endpoints, a higher level is a reflection of an overall greater kinase activity on that substrate.

The analysis reveals a striking degree of heterogeneous signaling (FIG. 20) amongst the individuals. Each subject's sample reflected a unique constellation of kinase driven signaling events. This observation concurs with recent gene microarray analysis and indicates that while some other cancers such as chronic myelogenous leukemia and stromal tumors are underpinned by a common pathway defect (e.g. c-kit family signaling activation), sporadic human breast cancer and other epithelial tumors are controlled by a multiplex of protein circuitry derangements. As shown in FIG. 20 and in Table below, a subset of tumor portraits grouped into classes dominated by phosphorylation heterogeneity. Generally, the "normal" epithelial signaling portraits are grouped together in large families that are distinct from the tumor fingerprint subsets (FIG. 20).

TABLE 13

| Phenotype | Kinase Substrate Correlates |
|---|---|
| Tumor Class 1 | ↑ER-ABL Activity/↓PKCα-STAT1 Activity |
| Tumor Class 2 | Broad Heterogeneous Activity/↓PKCα-STAT1 Activity |
| Tumor Class 3 | Broad Activity/↑c-erbB2-AKT/↓PKCα-STAT1 Activity |
| Tumor Class 4 | Quiescent/↓PKCα-STAT1 Activity |
| Normal | ↑PKCα-STAT1 Activity |

However, within the context of the underlying tumor heterogeneity, the clustering reveals larger subsets of tumors that have common pathway activation, some which are expected and some unexpected. For example, the 10 patients at the top of the map are dominated by estrogen receptor (ER) overexpression and phosphorylation (tumor group 1). Both growth factor receptor endpoints (ER and c-erbB2) analyzed in this study showed tight concordance between the overall expression of the receptor and its phosphorylation. While the total and phosphorylated levels of estrogen receptor and c-erbB2 receptor were tightly linked, the remainder of the kinase substrates showed no correlation between the phosphorylated and the non-phosphorylated form of the proteins. Thus analysis of the total protein, or its transcript, is not sufficient to predict its phosphorylated state.

Principal component analysis (FIG. 21A) of the data reinforced the observation that a significant number of tumor and histologically normal epithelium can be distinguished from each other using the STAT1 and PKCα kinase substrates [(43/45 cancers (95% CI=85-95%) and 15/16 histologically normal epithelium (95% CI=70-100%)]. Furthermore, PKCα phosphorylation, normalized to the total levels of PKCα were found to be dramatically decreased, or below the limits of detection in 7/8 patients (95% CI=47%-100%) with greater than 4 positive lymph nodes compared to a relatively elevated level in 8/9 patients (95% CI=52%-100%) with fewer than 4 positive nodes (FIG. 21B).

Linkage between known kinase substrate endpoints within well studied signaling pathways seems to hold true in this study set when an unsupervised clustering approach is used. These types of linkages provide increased confidence when unexpected pathway cross talk is discovered. An example is the classic Ras-ERK pathway, which is tightly linked as a sibling in the dendogram of FIG. 20, which was built without prior knowledge. Additionally, another tightly linked sibling combination identified by the clustering is the coordinate phosphorylation between p38, CREB and IkB, transcription factors, or transcription factor inhibitors (IkB).

The clustering analysis also reveals unexpected kinase substrate linkages. While the majority of patients with phosphorylated and over-expressed ER have expectedly low c-erbB2 levels, the tightest linkage between ER phosphorylation was c-abl phosphorylation (FIG. 20) indicating a potentially new cross-talk between the ER pathway through a classic pro-survival pathway. This correlation serves as a rational basis for new combinatorial therapeutic options such as combinations of aromatase inhibitors for ER signal damping with c-kit pathway inhibitors such as imatinib mesylate (Gleevec).

Women with a breast cancer overexpressing c-erbB2 are elegible for treatment with the humanized mouse antibody (Trastuzumab, Herceptin™). However, only a fraction of these women end up responding to the treatment. It is now believed that the responders are the small percentage of breast cancer patients with carcinomas bearing a phosphorylated, active form of c-erbB2. As shown in FIG. 20, the 5 of the 45 patients with the highest levels of c-erb2 expression and phosphorylation are grouped together (tumor group 3), but only 3 of these patients have highly phosphorylated and thus activated c-erbB2. Moreover, AKT phosphorylation levels are strongly correlated proportionately with activated c-erbB2 levels in those 5 patients, which may provide clues about and a method for monitoring resistance.

While the protein signaling pathway profiling of human breast cancer reveals a high degree of patient specific heterogeneity, transcendent portraits emerge that can discriminate tumor circuitry from "normal" pathway usage. It is important to note that what constitutes a "normal" pathway state is in many instances patient specific (FIG. 20).

Since the pattern recognition results are built from asynchronous cells, a determination of dominant pathways that could distinguish carcinoma from histologically normal appearing epithelial cells regardless of tumor proximity was made. Unexpectedly, clustering analysis revealed that phosphorylation of PKCα was tightly associated with phosphorylation of STAT1, and that this is the one dominant feature that seemed to segregate normal from tumor (FIG. 20). Principal component analysis (FIG. 21A) of the data reinforce that a significant number of tumor and histologically normal epithelium can be distinguished from each other using the STAT1 and PKCα kinase substrates. This observation may have clinical significance, since PKCα signaling has been described as being important in down-modulating prosurvival pathways, possibly through direct inhibition of AKT phosphorylation. Therefore, loss of PKCα activation in the normal cell population may be a critical early event in elimination of an important feedback mechanism on control of cellular apoptosis. STAT1 phosphorylation in breast cancer has been recently shown to correlate with outcome, with those patients who had the highest levels correlating with the longest period of disease free survival. This observation is not unexpected since STAT1 signaling is known to be a critical regulator of anti-proliferative and pro-apoptosis events. Therefore it appears important to analyze phosphorylation events that decrease as well as increase during carcinogenesis to identify potential combinations of therapeutic agents that can be used to treat early stage cancers, since activation of specific phosphatases during cancer progression and metastasis may be just as critical as kinase activation. Therefore, therapeutic agents that inhibit phosphatases are also useful.

Based on the finding that high PKCα phosphorylation levels correlated significantly with the normal phenotype, it was determined whether or not PKCα phosphorylation in primary tumor specimens correlates with critical clinical outcome measures. This analysis employed a study set of 17 breast cancer specimens obtained from patients in the neoadjuvant setting. Patients in this dataset had persistent tumor after receiving 3 months of A/C therapy alone or A/C therapy followed by Taxol. Persistent nodal involvement is known to be a very significant prognostic factor for outcome in the neoadjuvant setting. In fact, histologically positive lymph nodes after surgery are associated with a worse prognosis than pathologically positive nodes found at the time of primary surgical resection (prior to adjuvant therapy) and patients with 4 or more positive nodes after therapy have much poorer disease free survival. Tumor in lymph nodes at the time of initial assessment may reflect the likelihood of micrometastatic disease and the risk of distant recurrence, whereas lymph node involvement after chemotherapy may indicate both risk of distant disease and relative resistance to the chemotherapeutic regimen used.

The correlation revealed in FIG. 21B suggests that the measurements of PKCα activity and the correspondingly regulated pro-survival pathways may be important new measures of clinical response to chemotherapy. The absence of PKCα activity after the initiation of chemotherapy could identify a subset of patients who are resistant to chemotherapy.

In summary, while patient heterogen333ity at the cell signaling level in the study sets of human breast cancer was evident, the patients could still be placed into groups based on dominant well known and unexpected signal pathway networks. Thus, a given class of therapy may be effective for only a subset of patients who harbor tumors with susceptible and specific protein network defects and provides strong justification for the strategy to select a treatment using combinations of therapeutic agents that best match the individual tumor's aberrant signaling profile. Currently, cancer therapy has been directed at a single molecular target.

EXAMPLE 7

Figure 22:
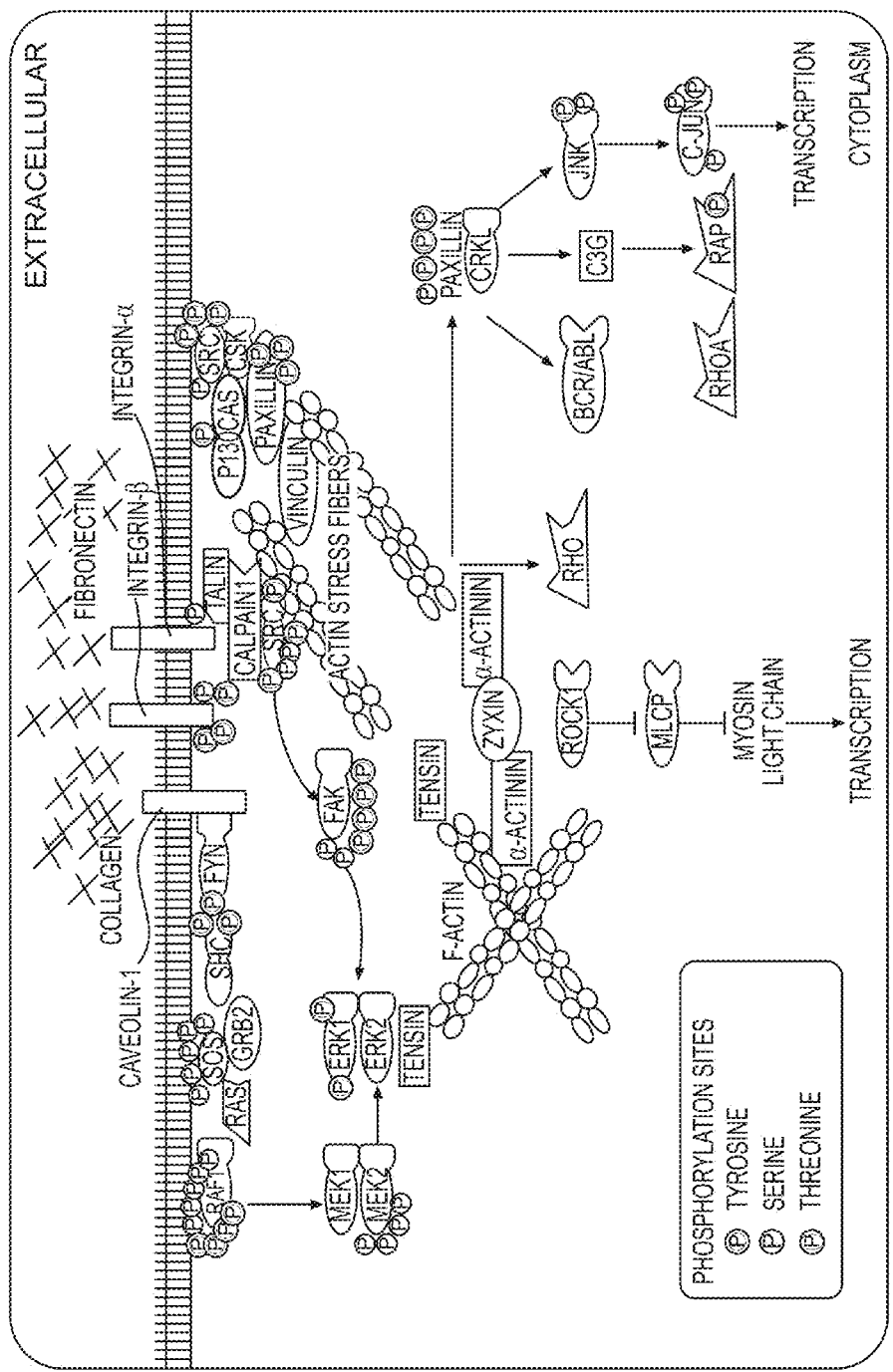
FIG. 22 is a representative diagram of the integrin signaling pathway.
Figure 23:
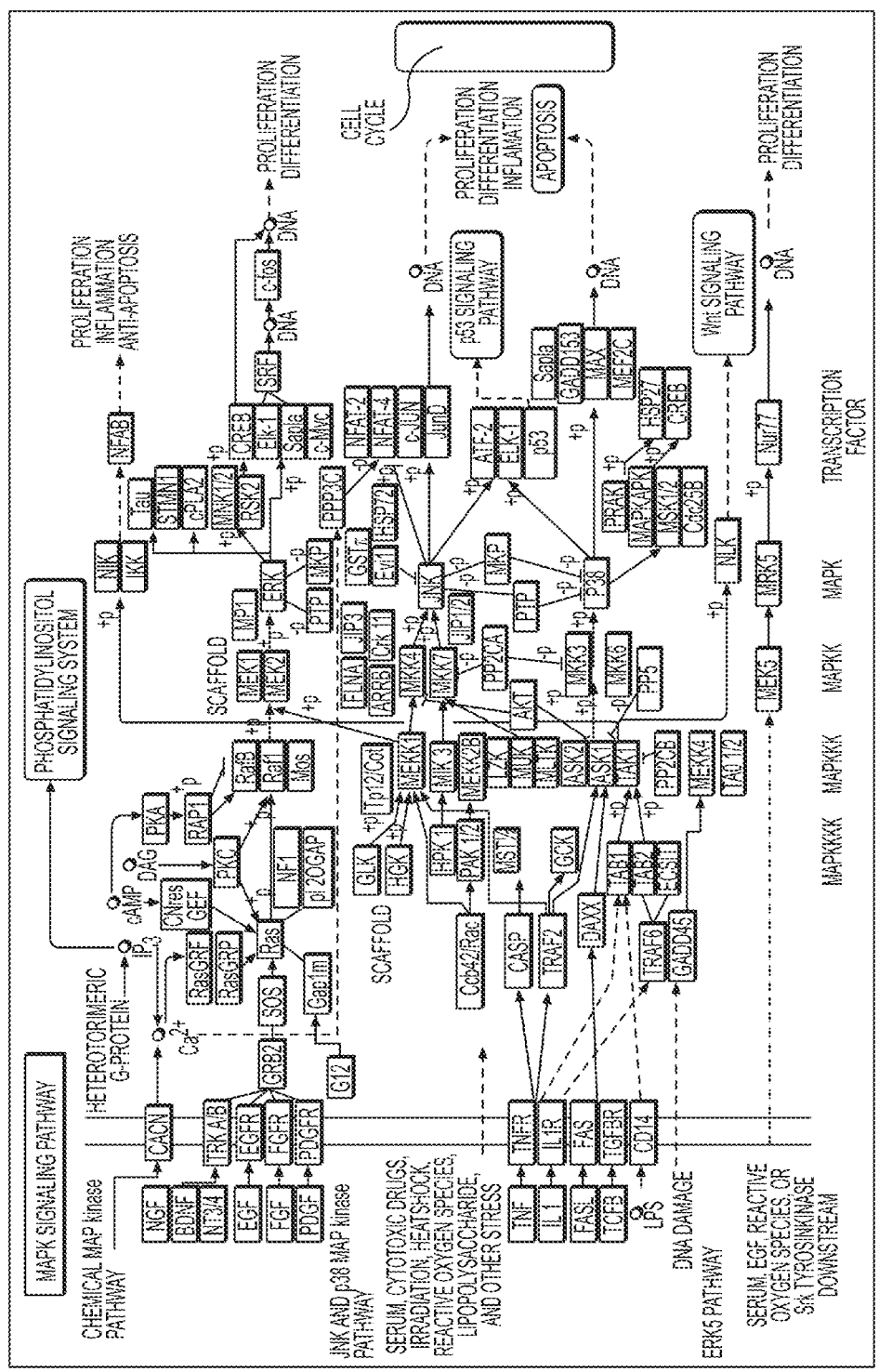
FIG. 23 is a representative diagram of the MapK signaling pathway.
Figure 24:
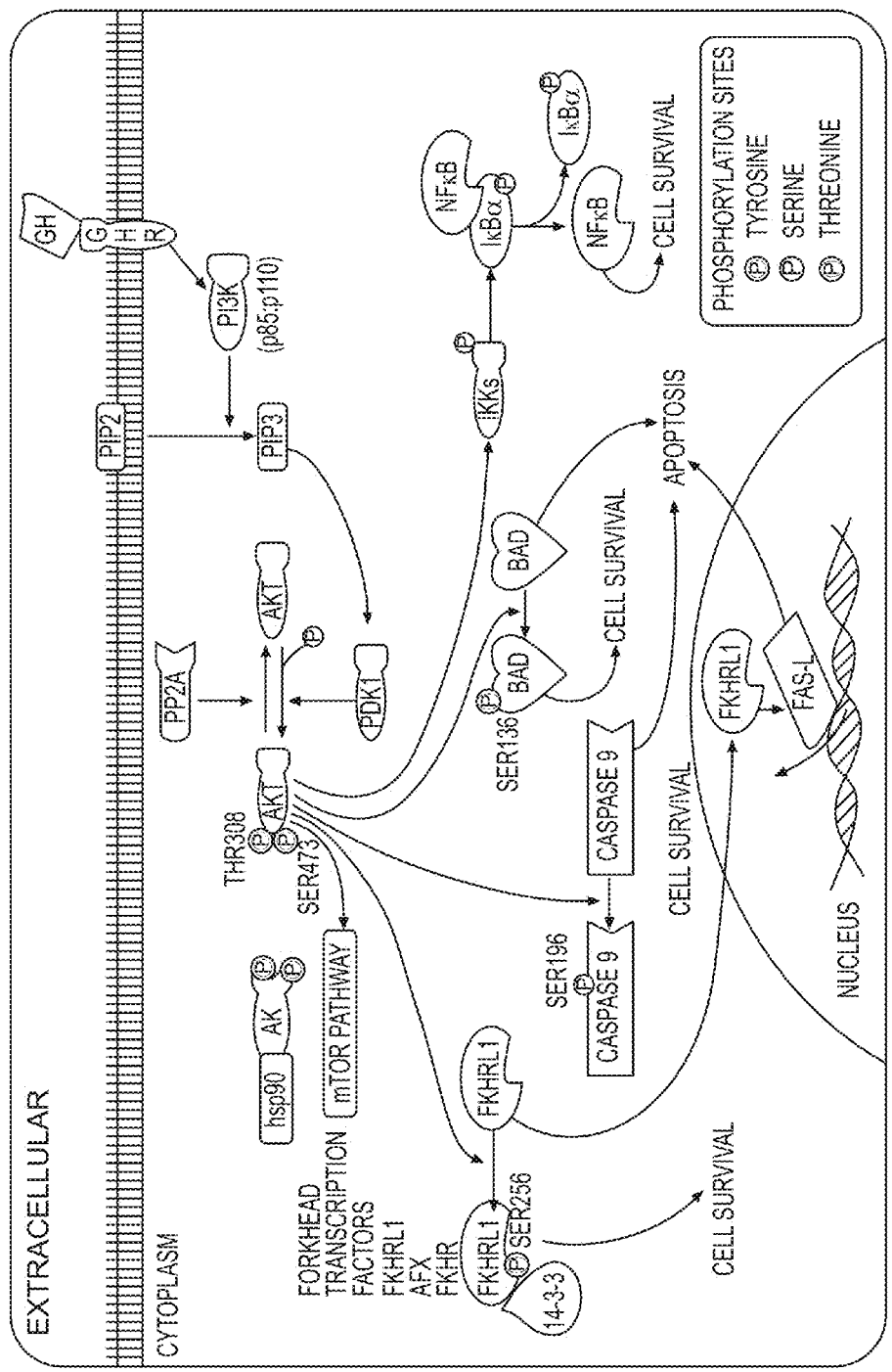
FIG. 24 is a representative diagram of the Akt signaling pathway.

Cell Protein Signaling Pathways and Networks, Signaling Protein Targets and Therapeutic Agents The disclosed methods may be applied to the analysis and treatment of any protein signaling pathway or network. Signal pathways and networks that respond to extracellular and intracellular signals are important for control of a wide variety of cellular level responses including, for example, apoptosis, growth, cytoskeletal remodeling, survival, receptor localization and distribution, gene transcription, protein synthesis, motility, angiogenesis and differentiation. Databases of signaling networks are well known so that they even have well-developed nomenclature (see, for example, Igarashi and Kaminuma, *Pac Symp Biocomput.*, 1997; 187-97; incorporated by reference herein) and are, for example, commercially available from Ingenuity, Mountain Park, Calif. (The Ingenuity Pathways Knowledge Base, a curated database of biological networks created from millions of individually modeled relationships between proteins, genes, complexes, cells, tissues, drugs, and diseases). Furthermore, modeling software that can be used to detect and delineate cell signaling pathways also is available from Ingenuity (Ingenuity Pathways Analysis, a web-delivered application that can be used to explore, understand, and discover therapeutically relevant networks). Diagrams of the integrin signaling pathway, the Mapk signaling pathway and the Akt signaling pathway are shown in FIGS. 22, 23, and 24, respectively. Diagrams of additional pathways may be found on the Cell Signaling Technology website (Cell Signaling Technology, Beverly, Mass.). For example, this website provides diagrams of Mapk signaling pathways, an apoptosis/caspase signaling pathways, the Akt signaling pathway, translational control pathways, PKC/phospholipase signaling pathways, cell cycle pathways, cytokine signaling pathways, cytoskeletal signaling pathways, lymphocyte signaling pathways, and nuclear receptor and Wnt signaling pathways, among others.

In disease states such as cancer, these signal pathways are often deranged and may become aberrantly interconnected so that signals that would normally stimulate one cellular response may abnormally stimulate multiple cellular responses, or signals may become inappropriately amplified within individual pathways, again leading to abnormal cellular responses. Restoration of normal signaling patterns using the disclosed therapeutic methods may be monitored on the molecular level, or may be monitored by observing the cellular responses under the control of the signaling pathways.

The signal pathways that control cellular responses comprise series of interconnected proteins and other molecules that interact and/or react with one another to propagate and amplify stimuli. Stimuli are passed along signaling pathways through interconnections between pathway members. The interconnections occur in a wide variety of ways, for example, through protein-protein interactions (such as homo- or hetero-dimerization and oligomerization), protein phosphorylation (such as mediated by serine-threonine kinases and tyrosine kinases, and phosphatases), and other post-translational modifications such as farnesylation, myristylation, ubiquitinization and acetylation. Interconnections may also occur by protein cleavage, translocation of pathway members within cellular organelles and compartments, receptor dimerization, and ion channel activation. Still other interconnections may occur through soluble mediators (such as cyclic AMP and calcium ions), receptor-ligand interactions, protein-nucleic acid interactions (such as by transcriptions factors), protein-lipid interactions (for example, lipid rafts can translocate signal pathway proteins), and protein-carbohydrate interactions.

Apoptosis, or programmed cell death, is a regulated physiological process leading to cell death characterized by cell shrinkage, membrane blebbing and DNA fragmentation. Apoptosis is induced by a family of receptors known collectively as "death receptors" including Fas, TNFR, DR3, DR4 and DR5. Pro-apoptotic stimuli include the FasL, TNF, DNA damage and ER stress. Caspases, a family of cysteine proteases, are central regulators of apoptosis. Initiator caspases (including 8, 9, 10 and 12) are closely coupled to pro-apoptotic signals. For example, the receptors, Fas and the TNFR activate caspases 8 and 10, DNA damage leads to the activation of caspase 9; and ER stress leads to the calcium-mediated activation of caspase 12. Death receptor ligands characteristically initiate signaling via receptor oligomerization, recruitment of specialized adaptor proteins and activation of caspase cascades. Once activated, the intiator caspases cleave and activate downstream effector caspases (including 3, 6 and 7) which in turn cleave cytoskeletal and nuclear proteins and induce apoptosis. Cytochrome C, released from mitochondria, is coupled to the activation of caspase 9, a key initiator caspase. Anti-apoptotic ligands including growth factors and cytokines activate AKT and p90RSK, which inhibit Bad and prevent cytochrome C release. TNFR can also stimulate an anti-apoptotic pathway by inducing IAP, which directly inhibits caspases 3, 7 and 9. For example, FasL binding induces Fas trimerization and recruits initiator caspase 8 via the adapter protein FADD. Caspase 8 then oligomerizes and is activated via autocatalysis. Activated caspase 8 stimulates apoptosis via two parallel cascades: it directly cleaves and activates caspase-3, and it cleaves Bid (a Bcl-2 family protein). Truncated Bid (tBid) translocates to mitochondria, inducing cytochrome c release, which sequentially activates caspases 9 and 3. TNF and DR-3L can deliver pro- or anti-apoptotic signals. TNFR and DR3 promote apoptosis via the adaptor proteins TRADD/FADD and the activation of caspase 8. Alternatively, apoptosis is inhibited via an adaptor protein complex including RIP which activates NF-êB and induces survival genes including IAP.

Survival includes active inhibition of apoptosis, which is accomplished either by inhibiting caspases or by preventing their activation. The PI3K pathway, activated by many survival factors, leads to the activation of Akt, an important node in survival signaling. Activated Akt inhibits the proapoptotic Bcl-2 family member Bad, directly inhibits caspase-9, and inhibits additional apoptotic pathways linked to FKHR and GSK-3. Many growth factors and cytokines induce anti-apoptotic Bcl-2 family members. The Jaks and Src phosphorylate and activate Stat3, inducing the expression of Bcl-xL and Bcl-2. Erk1/2 and PKC activate p90RSK, which activates CREB and induces the expression of Bcl-xL and Bcl-2. These Bcl-2 family members protect the integrity of mitochondria, preventing cytochrome C release and the subsequent activation of caspase-9. TNF not only induces apoptosis by activating caspase-8 and -10, but can also inhibit apoptosis signaling via NF-kappaB, which induces the expression of IAP, an inhibitor of caspases 3, 7 and 9.

The Bcl-2 family of proteins regulate apoptosis by controlling mitochondrial permeability and the release of cytochrome C. The anti-apoptotic proteins Bcl-2 and Bcl-xL reside in the outer mitochondrial wall and inhibit cytochrome C release. The pro-apoptotic Bcl-2 proteins Bad, Bid, Bax and Bim reside in the cytosol, but translocate to mitochondria following death signaling where they promote the release of cytochrome C. Bad translocates to mitochondria and forms a pro-apoptotic complex with Bcl-xL. This translocation is inhibited by survival factors that induce the phosphorylation of Bad, leading to its cytosolic sequestration. Cytosolic BID is cleaved by caspase 8 following signaling through Fas. The active fragment of Fas (tBid) translocates to mitochondria. Similarly, Bax and Bim translocate to mitochondria in response to death stimuli, including survival factor withdrawal. p53, activated following DNA damage, induces the transcription of Bax. Released cytochrome C binds Apaf1 and forms an activation complex with caspase 9. Bcl-xL, Bcl-2 and Bax apparently influence the voltage-dependent anion channel (VDAC), which can control cytochrome C release.

Mitogen-activated protein kinases (MAPK) are a family of serine/threonine protein kinases that are widely conserved among eukaryotes and are involved in many cellular responses such as cell proliferation, cell differentiation, cell motility and apoptosis. MAPK signaling cascades are organized hierarchically into three-tiered modules. MAPKs are phosphorylated and activated by MAPK-kinases (MAPKKs), which in turn are phosphorylated and activated by MAPKK-kinases (MAPKKKs). The MAPKKK is in turn activated by interaction with a family of small GTPases and/or other protein kinases connecting the MAPK module to the cell surface receptor or external stimuli.

The MAPK/Erk signaling cascade is activated by a wide variety of receptors involved in growth and differentiation, including receptor tyrosine kinases (RTKs), integrins, and ion channels. The specific components of the cascade vary greatly among different stimuli, but the architecture of the pathway usually includes a set of adaptors (Shc, GRB2, Crk, etc.) linking the receptor to a guanine nucleotide exchange factor (Sos, C3G, etc.) transducing the signal to small GTP binding proteins (Ras, Rap1), which in turn activate the core unit of the cascade composed of a MAPKKK (Raf), a MAPKK (MEK1/2) and MAPK (Erk). An activated Erk dimer can regulate targets in the cytosol and/or translocate to the nucleus where it can phosphorylate a variety of transcription factors regulating gene expression.

G-protein-coupled receptors (GPCRs) are activated by a wide variety of external stimuli. Upon receptor activation the G-protein exchanges GDP for GTP, causing the dissociation of the GTP-bound Galpha and the Gbetagamma subunits, triggering diverse signaling cascades. Receptors coupled to different heterotrimeric G-protein subtypes can utilize different scaffolds to activate the small G-protein/MAPK cascade, employing at least three different classes of tyrosine kinases. Src family kinases are recruited following activation of PI3 Kgamma by Gbetagamma subunits. They are also recruited by receptor internalization, cross-activation of receptor tyrosine kinases, or by signaling through an integrin scaffold involving Pyk2 and/or FAK. GPCRs can also employ PLCbeta to mediate activation of PKC and CaMKII, which can have either stimulatory or inhibitory consequences for the downstream MAPK pathway.

Stress-activated protein kinases (SAPK)/Jun N-terminal kinases (JNK) are members of the MAPK family and are activated by a variety of environmental stresses, inflammatory cytokines, growth factors and GPCR agonists. Stress signals are delivered to this cascade by members of small GTPases of the Rho family (Rac, Rho, cdc42). As with the other MAPKs, the membrane proximal kinase is a MAPKKK, typically MEKK1-4, or a member of the mixed lineage kinases (MLK) that phosphorylates and activates MKK4 (SEK) or MKK7, the SAPK/JNK kinases. Alternatively, MKK4/7 can be activated by a member of the germinal center kinase (GCK) family in a GTPase-independent manner. SAPK/JNK translocates to the nucleus where it regulates the activity of several transcription factors such as c-Jun, ATF-2 and p53.

The G1/S cell cycle checkpoint controls the passage of eukaryotic cells from the first "gap" phase (G1) into the DNA synthesis phase (S). Two cell cycle kinases, CDK4/6-cyclin D and CDK2-cyclin E, and the transcription complex that includes Rb and E2F are pivotal in controlling this checkpoint. During G1-phase, the Rb-HDAC repressor complex binds to the E2F-DP1 transcription factors, inhibiting the downstream transcription. Phosphorylation of Rb by CDK4/6 and CDK2 dissociates the Rb-repressor complex, permitting transcription of S-phase genes encoding for proteins that amplify the G1- to S-phase switch and that are required for DNA replication. Many different stimuli exert checkpoint control including TGFbeta, DNA damage, contact inhibition, replicative senescence and growth factor withdrawal. The first four act by inducing members of the INK4 or Kip/Cip families of cell cycle kinase inhibitors. TGFbeta additionally inhibits the transcription of Cdc25A, a phosphatase that activates the cell cycle kinases. Growth factor withdrawal activates GSK-3beta, which phosphorylates cyclin D, leading to its rapid ubiquitination and proteosomal degradation. Ubiquitination, nuclear export and degradation are mechanisms commonly used to rapidly reduce the concentration of cell cycle control proteins.

The G2/M DNA damage checkpoint prevents the cell from entering mitosis (M-phase) if the genome is damaged. The cdc2-cyclin B kinase helps regulate this transition. During G2-phase, cdc2 is maintained in an inactive state by the kinases Wee1 and Myt1. As cells approach M phase, the phosphatase cdc25 is activated, perhaps by the polo-kinase Plk1. Cdc25 then activates cdc2, establishing a feedback amplification loop that efficiently drives the cell into mitosis. DNA damage activates the DNA-PK/ATM/ATR kinases, initiating two parallel cascades that inactivate cdc2-cyclin B. The first cascade rapidly inhibits progression into mitosis: the Chk kinases phosphorylate and inactivate cdc25, which can no longer activate cdc2. The second cascade is slower. Phosphorylation of p53 dissociates it from MDM2, activating its DNA binding activity. Acetylation by p300/PCAF further activates its transcriptional activity. The genes that are turned on by p53 constitute effectors of this second cascade. They include 14-3-3, which binds to the phosphorylated cdc2-cyclin B kinase and exports it from the nucleus; GADD45, which apparently binds to and dissociates the Cdc2-cyclin B kinase; and p21$^{Cip1}$, an inhibitor of a subset of the cyclin-dependent kinases including Cdc2 (CDK1).

The synthesis of new protein is a highly regulated process that allows rapid cellular responses to diverse stimuli in the absence of transcription. Initiation of protein synthesis begins after the separation of the ribosome into its 40S and 60S subunits. Different eukaryotic initiation factors (eIFs) catalyze the assembly of a functional ribosomal complex including the 40S subunit, mRNA and tRNA, and finally the 60S subunit before the first peptide bond is formed. Most regulatory stimuli, such as growth factors and stress, control rate-limiting steps of the initiation process by either stimulating or inhibiting specific eIFs. Elevated levels of $Ca^{++}$ or cAMP can also attenuate translation by blocking the action of eukaryotic elongation factor 2 (eEF2).

Protein phosphorylation plays an important role in the control of translation by eukaryotic initiation factor 2 (eIF2). eIF2 binds GTP and Met-tRNAi and transfers the Met-tRNA to the 40S subunit, to form the 43S preinitiation complex. Later in the cycle, prior to elongation, the bound GTP is hydrolyzed, releasing eIF2-GDP. For eIF2 to promote another round of initiation, GDP must be exchanged for GTP, a reaction catalyzed by eIF2B. Kinases activated by viral infection (PKR), endoplasmic reticulum stress (PERK/PEK), amino acid deprivation (GCN2), and hemin deficiency (HRI) can phosphorylate the alpha subunit of eIF2. This phosphorylation stabilizes the eIF2-GDP-eIF2B complex, inhibiting the turnover of eIF2B. The eIF2B is also inhibited by GSK-3beta phosphorylation. These events result in a shutdown of cellular protein synthesis and can lead to apoptosis.

eIF4F and p70 S6 kinase play critical roles in translational regulation. eIF4F is a complex whose functions include the recognition of the mRNA 5' cap structure (eIF4E), delivery of an RNA helicase to the 5' region (eIF4A), bridging of the mRNA and the ribosome (eIF4G), and circularization of the mRNA via interaction between eIF4G and the poly(A) binding protein (PABP). Several stimuli, including growth factors and cytokines, regulate the eIF4 complex and p70 S6 kinase by initiating a phosphorylation cascade involving the sequential activation of PI3K, PDK1/2, Akt/PKB and FRAP/mTOR kinase. FRAP/mTOR, participate in phosphorylation of 4E-BP, leading to its dissociation from and activation of eIF4E. MNK1/2, activated by Erk and p38 MAPK, phosphorylates and activates eIF4E. Both processes contribute to the association of eIF4E and eIF4G to form the active eIF4F complex, a necessary component of the 48S initiation complex. Phosphorylation of ribosomal protein S6 by p70 S6 kinase stimulates the translation of mRNAs with a 5' oligopyrimidine tract which typically encode components of the protein synthesis apparatus.

Insulin controls critical energy functions such as glucose and lipid metabolism. Insulin activates the insulin receptor tyrosine kinase, which phosphorylates and recruits different substrate adaptors such as the IRS family of proteins. Tyrosine-phosphorylated IRS then displays binding sites for numerous signaling partners. PI3K has a major role in insulin functions, mainly via the activation of the Akt/PKB and the PKCzeta cascades. Activated Akt induces glycogen synthesis, through inhibition of GSK-3; protein synthesis via mTOR and downstream elements. Activated Akt also induces cell survival, through inhibition of several proapoptotic agents (Bad, Forkhead family transcription factors, GSK-3); and inhibits lipolysis via activation of PDE3. A major consequence of insulin stimulation is the stimulation of glucose uptake in muscle and adipocytes, which is mediated by translocation of GLUT4 vesicles to the plasma membrane. While the PI3K/Akt cascade participates in this process, another major pathway leading to GLUT4 translocation involves the insulin receptor-mediated phosphorylation of CAP and formation of the CAP:Cbl:CrkII complex. This complex, through its interaction with flotillin, localizes to lipid rafts facilitating GLUT4 translocation, using in the final step a Synip-containing specialized SNARE complex. Insulin signaling also has growth and mitogenic effects mediated by the Akt cascade, as well as by activation of the Ras/MAPK pathway. A negative feedback signal emanating from Akt/PKB, PKzeta, p70 S6K and perhaps the MAPK cascades results in serine phosphorylation and inactivation of IRS signaling.

The Wnt pathway (named as a hybrid of Wingless and Int) regulates cell fate decisions during development of a vide variety of animal species. Secreted Wnt glycoproteins bind to the Frizzled receptor, a family of serpentine receptors, to activate Dishevelled, a PDZ domain protein. Dishevelled acts to inhibit a cytoplasmic complex involving GSK-3, axin and APC that acts to degrade beta-catenin. GSK-3 phosphorylates beta-catenin leading to ubiquitination and degradation by the proteosome. Activation of the Wnt pathway inhibits degradation of beta-catenin allowing its nuclear transport and gene induction via binding to TCF. During the elaboration of cell types and tissues, the Wnt pathway often interacts with the FGF and TGF-beta pathways.

Protein acetylation plays a crucial role in regulating transcriptional activity. Acetylation complexes (such as CBP/p300) or deacetylation complexes (such as HDAC) can be recruited to DNA-bound transcription factors (TF) in response to signaling pathways. Histone hyperacetylation by histone acetyltransferases (HATs) is associated with transcriptional activation, presumably by remodeling nucleosomal structure into an open conformation more accessible to transcription complexes. Conversely, histone deacetylation is associated with transcriptional repression reversing the chromatin remodeling process. Several transcriptional coactivators and corepressors possess intrinsic acetylase or deacetylase enzymatic activities, respectively. Site-specific acetylation of a growing list of nonhistone proteins, including p53 and E2F, has been shown to play an important role in transcriptional regulation and cell proliferation.

The B-cell antigen receptor (BCR) is composed of membrane immunoglobulin molecules (mIg) and associated Igalpha/Igbeta heterodimers (alpha/beta). The MIg subunits bind antigen and cause receptor aggregation, while the alpha/beta subunits transduce signals to the cell interior. Receptor aggregation rapidly activates Src family kinases, including Lyn, Btk and Fyn, initiating complex signaling cascades involving multiple adaptors, kinases, phosphatases, G-proteins and transcription factors. The complexity of BCR signaling permits many distinct outcomes, including proliferation, differentiation, apoptosis, survival and tolerance. The outcome of the response is determined by the maturation state of the cell, the affinity of the antibody-antigen interaction, the cellular environment and the nature of the antigen. Many other transmembrane receptors are known to modulate specific elements of BCR signaling. A few of these, including CD45 and CD19, are indicated above as closed rectangles.

Jaks and Stats are components of cytokine receptor signaling: regulating growth, survival, differentiation and pathogen resistance. An example of these pathways is the IL-6 (or gp130) family of receptors. Cytokine binding induces receptor dimerization, activating the associated Jaks, which phosphorylate the receptor itself. The phosphorylated receptor then serves as a docking site for the SH2-containing Stats. Receptor-bound Stats are phosphorylated by Jaks, dissociate from the receptor, dimerize and translocate into the nucleus.

Once in the nucleus, Stat dimers bind specific enhancers, regulating the transcription of target genes. The suppressor of cytokine signaling (SOCS) family of proteins dampen receptor signaling via homologous or heterologous feedback regulation. In addition to activating Stats, Jak kinases phosphorylate other signaling proteins, linking Jak signaling to other pathways such as the MAP kinases. Jaks or Stats can also participate in signaling through other receptor classes.

The disclosed methods employ the methods outlined in Example 1 to identify derangements in signaling pathways such as those described above. Once deranged signaling pathways and the members of a signaling network to which they belong are identified (see, for example, therapeutic agents which target particular members within the pathway/network may be selected. Table 2 below presents a representative list of known members of protein signaling pathways against which therapeutic agents may be selected if the signaling pathway, or network, containing these proteins, are deranged. Additional known signal proteins not in Table 2, or signal proteins not yet discovered may be targeted using the disclosed methods.

TABLE 2

| Representative List of Signal Pathway Components | |
|---|---|
| 4E-BP | eIF4E binding protein |
| Abl | Ableson protein tyrosine kinase |
| ACTR | A histone acetyltransferase |
| AIF | Programmed cell death protein 8 |
| ANT | Adenine nucleotide translocation channel |
| Apaf-1 | Apoptotic protease activating factor 1 |
| APP | beta-Amyloid precursor protein |
| APPs | Acute phase proteins |
| ASIP | Agouti switch protein |
| ASK | Apoptosis signal-regulating kinase (e.g., ASK1) |
| ATF-2 | Activating transcription factor 2 |
| ATM | Ataxia telangiectasia-mutated protein kinase |
| ATR | ATM and Rad3-related protein kinase |
| Bam32 | B-cell adaptor molecule 32 kDa |
| BCAP | B-cell adaptor for PI3K |
| Bcl-10 | B-cell leukemia 10 protein |
| Bfl-1 | Bcl-2-related protein A1 |
| Bid | A BH3 domain-only death agonist protein |
| Bimp1 | B-lymphocyte-induced maturation protein 1 |
| BLNK | B-cell linker protein |
| BRCA | Breast cancer growth suppressor protein |
| Btk | Bruton's tyrosine kinase |
| C3G | Guanine nucleotide-releasing factor 2 |
| CAD | Caspase-activated deoxyribonuclease |
| Cam | Calmodulin |
| CaMK | Calcium/calmodulin-dependent kinase |
| CAP | c-Cbl-associated protein |
| Cas | p130CAS, Crk-associated substrate |
| Caspase | Cysteine proteases with aspartate specificity |
| CBL | Cellular homologue of the v-Cbl oncogene |
| CBP | CREB binding protein |
| CD19 | B-lymphocyte antigen CD19 |
| CD22 | B-cell receptor CD22 |
| CD40 | B-cell surface antigen CD40 |
| CD45 | Leukocyte common antigen, a phospho-tyrosine phosphatase |

TABLE 2-continued

| Representative List of Signal Pathway Components | |
|---|---|
| CD5 | Lymphocyte antigen CD5 |
| cdc2 | Cell division cycle protein 2, CDK1 |
| cdc34 | Cell division cycle protein 34, a ubiquitin conjugating (E2) enzyme |
| cdc42 | Cell division cycle protein 42, a G-protein |
| CDK | Cyclin-dependent kinase |
| Chk | Checkpoint kinase |
| CHOP | C/EBP homologous protein 10 |
| Cip | CDK-interacting protein |
| CIS | Cytokine inducible SH2-containing protein |
| c-Myb | Cellular homologue of avian myeloblastosis virus oncogene |
| c-Myc | Cellular homologue of avian myelocytomatosis virus oncogene |
| CREB | cAMP response element-binding protein |
| CRK | Proto-oncogene c-Crk |
| CrkII | One of three cellular homologues of the v-Crk oncogene |
| DAG | Diacylglycerol |
| Daxx | Fas death domain-associated protein |
| Diablo | Direct IAP binding protein with low pI |
| DNA-PK | DNA-activated protein kinase |
| DP1 | Member of the E2F transcription factor family |
| DPC4 | Deleted in pancreatic cancer locus 4 (also Smad4) |
| DR3 | Death receptor 3 |
| dsRNA | Double-stranded RNA |
| E2F | Transcription factor family including E2F- and DP-like subunits |
| EEF | Eukaryotic elongation factor |
| Egr-1 | Early growth response protein 1 |
| EIF | Eukaryotic initiation factor |
| Elk-1 | Ets domain protein |
| ENaC | Epithelial sodium channel |
| EPAC | Exchange protein activated by camp |
| ER | Endoplasmic reticulum |
| ER | Estrogen receptor |
| Erk | Extracellular signal-regulated kinase |
| ETS | C-ets-1 protein, a transcription factor |
| FADD | Fas-associated protein with death domain |
| FAK | Focal adhesion kinase |
| FcγRII | Immunoglobulin gamma Fc region receptor II-B |
| FKHR | Forkhead in rhabdomyosarcoma |
| FLIP | FLICE (Caspase-8) inhibitory protein |
| FRAP | FKBP12-rapamycin-associated protein |
| FRS2 | Lipid anchored Grb2 binding protein activated by FGF receptor |
| Fyn | A Src family proto-oncogene tyrosine-protein kinase |
| Gab1 | GRB2-associated binder-1 |
| GADD34 | Growth arrest and DNA damage protein 34 |
| GADD45 | Growth arrest and DNA damage protein 45 |
| GAP | GTPase activating proteins |
| GAS | IFNgamma-activated sequences |
| Gas2 | Growth arrest-specific gene 2 |
| GCK | Germinal center kinase |
| GCN2 | General control of amino acid biosynthesis protein 2, an S/T kinase |

TABLE 2-continued

Representative List of Signal Pathway Components

| | |
|---|---|
| GCN5 | General control of amino acid biosynthesis protein 5, a histone acetyltransferase |
| GEF | Guanine nucleotide exchange factor |
| GLUT-4 | Glucose transporter type 4 |
| GPCR | G-protein coupled receptor |
| GRB2 | Growth factor receptor-bound protein 2 |
| GRB10 | Growth factor receptor-bound protein 10 |
| GRIP | Glucocorticoid receptor interacting protein, a histone acetyltransferase |
| GRK | G-protein coupled receptor kinase |
| GSK-3β | Glycogen synthase kinase-3 beta |
| HDAC | Histone deacetylase |
| HMG | High mobility group |
| HPK | Hematopoietic progenitor kinase |
| HRI | Hemin-regulated inhibitor |
| Hrk/DP5 | Harakiri protein, an activator of apoptosis |
| HSP27 | Heat shock protein 27 |
| IAP | Inhibitor of apoptosis |
| ICAD | Inhibitor of caspase-activated deoxyribonuclease |
| IκB | Inhibitor of NF-kappa B |
| IKK | I-kappa-B kinase |
| INK4 | Inhibitor of CDK4 |
| IRS | Insulin receptor substrate (e.g., IRS-1) |
| ISRE | Interferon-stimulated response element |
| Jak | Janus-family tyrosine kinase |
| JIP-1 | JNK interacting protein 1 |
| JNK | Jun N-terminal kinase |
| KSR | Kinase suppressor of Ras |
| LC8 | Dynein light chain, cytoplasmic |
| Lyn | A Src family proto-oncogene tyrosine-protein kinase |
| M3/6 | Dual-specificity phosphatase |
| MALT1 | Mucosa-associated lymphoma translocation protein 1 |
| MAPK | Mitogen-activated protein kinase |
| MAPKAP- | MAP kinase activated protein kinase 2 |
| MDM2 | Murine double minute 2, a p53-associated oncogene |
| MEF2 | Myocyte enhancer factor 2 |
| MEK | MAPK/Erk kinase |
| MEKK | MAPK/Erk kinase kinase |
| mIg | Membrane immunoglobulin |
| MKP | MAP kinase phosphatase |
| MLK | Mixed lineage kinase |
| MNK | MAP kinase interacting kinase |
| MP-1 | MEK partner 1 |
| MSK-1 | Mitogen and stress activated kinase 1 |
| mTOR | Mammalian target of rapamycin |
| MyoD | Myogenic determination factor |
| Myt1 | A dual-specificity protein kinase |
| Nck | Nck adaptor protein |
| NcoR | Nuclear receptor corepressor |
| NFAT | Nuclear factor of activated T-cells |
| NF-κB | Nuclear factor kappa B |
| NIK | Nuclear factor kappa B-induced kinase |
| Noxa | Damage" protein, a proapoptotic BH3-containing protein |
| 2-Oct | Octamer-binding transcription factor 2 |
| p19Arf | p19 alternative reading frame protein, a tumor suppressor |
| p300 | A histone acetyltransferase |
| p53 | Tumor suppressor protein that protects from DNA damage |
| p90RSK | 90 kDa ribosomal S6 kinase |
| PABP | Poly(A) tail-binding protein |
| PAIP1&2 | Polyadenylate binding protein-interacting proteins 1 and 2 |
| PARP | Poly(ADP-ribose)polymerase |
| Pax | Paxillin |
| PCAF | p300/CBP-associated factor, a histone acetyltransferase |
| pCIP | p300/CBP-interacting protein, a histone acetyltransferase |
| PDE3B | cGMP-inhibited 3',5'-cyclic phosphodiesterase B |
| PDK | 3-phosphoinositide-dependent protein kinase |
| PEK | Pancreatic eukaryotic initiation factor 2α-subunit kinase |
| PERK | Type I transmembrane ER-resident protein kinase |
| PI3K | Phosphoinositide 3 kinase |
| PIAS | Protein inhibitors of activated Stats |
| PIP2 | Phosphatidylinositol 3,4-bisphosphate |
| PIP3 | Phosphatidylinositol 3,4,5-trisphosphate |
| PKA | Protein kinase A |
| PKC | Protein kinase C |
| PKR | dsRNA-dependent serine/threonine protein kinase |
| PLCβ | Phospholipase C beta |
| PLCγ | Phospholipase C gamma |
| Plk1 | Polo-like kinase 1 |
| PLP2A | Phospholipase 2A |
| PP1 | Phospho-protein phosphatase 1 |
| PP2A | Phospho-protein phosphatase 2A |
| PPARγ | Peroxisome proliferator-activated receptor gamma |
| PR | Progesterone receptor |
| PRAK | p38 regulated activated kinase |
| PRK2 | Protein kinase C-related kinase 2 |
| PTEN | Phosphatase and tensin homologue deleted on chromosome 10 |
| PUMA | p53 upregulated modulator of apoptosis |
| PYK2 | Proline-rich tyrosine kinase 2 |
| RAIDD | RIP-associated ICH/CED-3-homologous protein with a death domain |
| Rap1 | Ras-related protein RAP-1A |
| RasGRP | Ras guanyl nucleotide-releasing protein |
| Rb | Retinoblastoma protein, a tumor suppressor |
| RGS | Regulator of G-protein signaling |
| RIP | Receptor-interacting protein |
| ROCK-1 | Rho-associated, coiled-coil-containing protein kinase |
| RTK | Receptor tyrosine kinase |
| RXR | Retinoid X receptor |
| S6 | Small subunit ribosomal protein S6 |
| SAPK | Stress-activated protein kinase |
| SCF | Skp-cdc53-F-box ubiquitin ligase complex |
| SGK | Serum/glucocorticoid-regulated kinase |
| Shc | SH2-containing collagen-related proteins |
| SHP1 | SH2-containing phosphatase 1 |
| SHP2 | SH2-containing phosphatase 2 |
| Sin3 | A transcriptional corepressor |
| SKP2 | S-phase kinase-associated protein 2 |
| Smac | Second mitochondria-derived activator of caspase |
| Smad | Contraction of Sma and Mad (Mothers against decapentaplegic) |
| SMRT | Silencing mediator of retinoic acid and thyroid hormone receptor |
| SNARE | Soluble N-ethylmaleimide attachment protein receptors |
| SOCS | Suppressor of cytokine signalling |
| Sos | Son of sevenless guanine nucleotide exchange factor |
| SRC1 | Steroid receptor coactivator 1, a histone acetyltransferase |
| SRF | Serum response factor |
| Stat | Signal transducer and activator of transcription |
| Syk | Tyrosine-protein kinase Syk |
| Synip | Syntaxin 4-interacting protein |
| TAB1 | TAK1 binding protein |
| TAFs | TBP-associated factors |
| TAK | TGF beta-activated kinase |

TABLE 2-continued

Representative List of Signal Pathway Components

| | |
|---|---|
| Tal | Talin |
| tBid | Truncated Bid |
| TBP | TATA-binding protein |
| TC10 | GTP-binding protein TC10 |
| TCF | T-cell factor |
| TF | Transcription factor |
| TH | Tyrosine hydroxylase |
| Tip60 | HIV-1-Tat interactive protein, a histone acetyltransferase |
| TNF | Tumor necrosis factor |
| TR | Thyroid hormone receptor |
| TRADD | TNF receptor-1-associated death domain protein |
| TRAF2 | TNF receptor-associated factor 2 |
| Vav | The one F proto-oncogene |
| Wee1 | A universal mitotic inhibitor kinase |

Any therapeutic agent that targets a signaling pathway protein may be employed to provide synergistic combinations according to the disclosure. Furthermore, because of the observed synergism, therapeutic agents that may not be used to treat subjects individually due to their high toxicity at effective doses may be employed in synergistic combinations because of the higher specificity and lower toxicity enabled by the disclosed methods. For example, any number of serine/threonine kinase inhibitors, tyrosine kinase inhibitors and Src kinase inhibitors may be used. Therapeutic agents for use in the disclosed methods may include those disclosed in English and Cobb, "Pharmacological inhibitors of MAPK pathways," Trends Pharmacol Sci 23: 40-45, 2002. Specific examples of signal pathway therapeutics provided in English and Cobb include VX745, HEP689, RPR200765A, PD98059, U0126, PD184352, Ro092210, LLZ16402, L783277, SP600125, Bay439006, and CEP1347. Additional examples are pyrazole compounds (see, for example U.S. Pat. No. 6,528,509), 2(pyrin-9-yl)-tetrahydrofuran-3,4-diol derivatives (see, for example, U.S. Pat. No. 6,528,494), aminothiazole compounds (see, for example, U.S. Pat. No. 6,521,759), 1,5-diarylsubstituted pyrazole compounds (see, for example, U.S. Pat. No. 6,509,361) and isoxazole inhibitors of ERK (see, for example, U.S. Pat. No. 6,495,582). Still further examples of agents are provided in U.S. Pat. Nos. 6,518,316 and 6,495,558.

Therapeutic agent combinations may be administered alone or in combination with any pharmaceutically acceptable carrier (see, for example, *Remington: The Science and Practice of Pharmacy*, 19$^{th}$ Edition, 1995). Any of the common pharmaceutical carriers, such as saline and sesame oil solutions can be used. Routes of parenteral administration include, but are not limited to, subcutaneous (sq), intracranial ventricular (icy), intrathecal (it), intravenous (iv), intramuscular (im), topical ophthalmic, subconjunctival, nasal, aural and transdermal. Therapeutics combinations of agents may be administered sq, iv or im in any conventional medium for intravenous injection, such as an aqueous saline or oil medium. The medium may also contain conventional pharmaceutical adjunct materials such as, for example, pharmaceutically acceptable salts to adjust the osmotic pressure, buffers, preservatives and the like.

Therapeutically effective doses of the compounds of the present invention can be determined by one of skill in the art. However, a useful starting concentration for the agents in the therapeutic combinations is the $IC_{50}$ of each drug, either measured in tissue or in vitro. In particular embodiments, the drugs in a therapeutic combination are administered at concentrations less than their individual IC50's. In other embodiments, the agents are administered at concentrations that alone provide less than 50% inhibition (e.g. less than 40%, 30%, 20% or 10% inhibition) of their targets as determined in microdissected samples, in vivo (e.g. by imaging) or in vitro, for example, in a test tube or a cell culture. Depending upon the efficacy of the agents used, they may be administered to achieve tissue concentrations between 1 fM and 100 mM, such as between 1 µM and 10 mM, for example, between 10 µM and 1 mM. Alternatively, agents in combinations according to the disclosure may be administered in dosages ranging from 1 ng/kg to 10 g/kg, such as from 100 ng/kg to 1 g/kg, for example, from 1 mg/kg to 100 mg/kg.

It should be understood that the foregoing relates only to particular embodiments and that numerous modifications or alterations may be made without departing from the true scope and spirit of the invention as defined in the following claims.

We claim:

1. A method for identifying a combination of therapeutic agents for individualized treatment of a disease in a patient caused by an abnormal network of interconnected cell signaling proteins leading to abnormal cellular growth, motility, survival, differentiation, proliferation, or angiogenesis, comprising the steps of:
   a) measuring levels of a post-translational modification of a plurality of different signaling proteins extracted from diseased cells obtained from the patient;
   b) providing levels of a post-translational modification of signaling proteins from reference cells corresponding to the signaling proteins extracted from the diseased cells obtained from the patient;
   c) detecting differences between the levels of the post-translational modification of the individual signaling proteins from the diseased cells and the levels of the post-translational modification of corresponding individual signaling proteins from the reference cells, thereby providing a cell-aggregated snapshot of the signaling proteins in the diseased cells that form an abnormal network of interconnected cell signaling proteins that leads to the abnormal cellular growth, motility, survival, differentiation, proliferation, or angiogenesis in the patient; and
   d) reporting a combination of at least two different therapeutic agents for administration to the patient to correct or partially correct the abnormal network by reducing the differences that were detected in the levels of the post-translational modification of two or more of the signaling proteins in the abnormal network of interconnected cell signaling proteins identified by steps (a)-(c) in the diseased cells compared to the levels of the post-translational modification of the corresponding signaling proteins in the reference cells.

2. The method of claim 1, wherein the post-translational modification comprises phosphorylation.

3. The method of claim 1, wherein the combination prevents shunting to or around a signaling pathway.

4. The method of claim 1, wherein the combination of therapeutic agents restores normal signaling patterns in diseased cells of the patient.

5. The method of claim 1, wherein the combination of therapeutic agents provides a synergistic normalization of the affected signaling proteins in diseased cells of the patient.

6. The method of claim 1, wherein the disease is cancer.

7. The method of claim 1, wherein the diseased cells are obtained by microdissection from tissue from the patient.

8. The method of claim 1, wherein measuring the post-translational modification of the signaling proteins comprises using protein microarray analysis.

9. The method of claim 1, wherein measuring the post-translational modification of the signaling proteins comprises using reverse phase protein microarray analysis.

10. The method of claim 1, wherein the differences between the level of the post-translational modification of the individual signaling proteins is an increase in the post-translational modification of two or more of the signaling proteins from the diseased cells in comparison to the same signaling proteins in the reference cells, and the therapeutic agents are selected to counteract the increase in the level of the post-translational modification of the individual signaling proteins from the diseased cells.

11. The method of claim 1, wherein the differences between the level of the post-translational modification of the individual signaling proteins is a decrease in the post-translational modification of two or more of the signaling proteins from the diseased cells in comparison to the same signaling proteins in the reference cells, and the therapeutic agents are selected to counteract the decrease in the level of the post-translational modification the individual signaling proteins from the diseased cells.

12. The method of claim 2, wherein the combination prevents shunting to or around a signaling pathway.

13. The method of claim 2, wherein the combination of therapeutic agents restores normal signaling patterns in diseased cells of the patient.

14. The method of claim 2, wherein the combination of therapeutic agents provides a synergistic normalization of the affected signaling proteins in diseased cells of the patient.

15. The method of claim 2, wherein the disease is cancer.

16. The method of claim 2, wherein the diseased cells are obtained by microdissection from tissue from the patient.

17. The method of claim 2, wherein measuring the phosphorylation of the signaling proteins comprises using protein microarray analysis.

18. The method of claim 2, wherein the differences between the level of the phosphorylation of the individual signaling proteins is an increase in the phosphorylation of two or more of the signaling proteins from the diseased cells in comparison to the same signaling proteins in the reference cells, and the therapeutic agents are selected to counteract the increase in the level of the phosphorylation of the individual signaling proteins from the diseased cells.

19. The method of claim 2, wherein the differences between the level of the phosphorylation of the individual signaling proteins is a decrease in the phosphorylation of two or more of the signaling proteins from the diseased cells in comparison to the same signaling proteins in the reference cells, and the therapeutic agents are selected to counteract the decrease in the level of the phosphorylation of the individual signaling proteins from the diseased cells.

20. The method of claim 2, wherein the disease is cancer, the diseased cells are obtained by laser capture microdissection from tissue from the patient, and measuring the phosphorylation of the signaling proteins comprises using reverse phase protein microarray analysis.

21. The method of claim 2, wherein the disease is cancer, the diseased cells are obtained by laser capture microdissection from tissue from the patient, measuring the phosphorylation of the signaling proteins comprises using reverse phase protein microarray analysis, and the combination prevents shunting to or around a signaling pathway.

22. The method of claim 21, wherein the combination of therapeutic agents restores normal signaling patterns in diseased cells of the patient.

23. A method for individualized treatment of a patient having a disease caused by a peculiar, abnormal network of interconnected cell signaling proteins leading to abnormal cellular growth, motility, survival, differentiation, proliferation, or angiogenesis, comprising the steps of:
   a) measuring levels of a post-translational modification of a plurality of different signaling proteins extracted from diseased cells obtained from the patient;
   b) providing levels of a post-translational modification of signaling proteins from reference cells corresponding to the signaling proteins extracted from the diseased cells obtained from the patient;
   c) detecting differences between the levels of the post-translational modification of the individual signaling proteins from the diseased cells and the levels of the post-translational modification of the corresponding individual signaling proteins in the reference cells, thereby providing a snapshot of the signaling proteins in the diseased cells that form an abnormal network of interconnected cell signaling proteins that leads to the abnormal cellular growth, motility, survival, differentiation, proliferation, or angiogenesis in the patient;
   d) reporting a combination of at least two different therapeutic agents for administration to the patient, wherein the agents reduce the differences that were detected in the levels of the post-translational modification of two or more of the signaling proteins in the abnormal network of interconnected cell signaling proteins identified by steps (a)-(c) in the diseased cells compared to the levels of the post-translational modification of the corresponding signaling proteins in the reference cells; and
   e) administering the combination to the patient.

24. The method of claim 23, wherein the post-translational modification comprises phosphorylation.

25. The method of claim 23, wherein the combination prevents shunting to or around a signaling pathway.

26. The method of claim 23, wherein the combination of therapeutic agents restores normal signaling patterns in diseased cells of the patient.

27. The method of claim 23, wherein the combination of therapeutic agents provides a synergistic normalization of the affected signaling proteins in diseased cells of the patient.

28. The method of claim 23, wherein the disease is cancer.

29. The method of claim 23, wherein the diseased cells are obtained by microdissection from tissue from the patient.

30. The method of claim 23, wherein measuring the post-translational modification of the signaling proteins comprises using protein microarray analysis.

31. The method of claim 23, wherein measuring the post-translational modification of the signaling proteins comprises using reverse phase protein microarray analysis.

32. The method of claim 23, wherein the differences between the level of the post-translational modification of the individual signaling proteins is an increase in the post-translational modification of two or more of the signaling proteins from the diseased cells in comparison to the same signaling proteins in the reference cells, and the therapeutic agents are selected to counteract the increase in the level of the post-translational modification of the individual signaling proteins from the diseased cells.

33. The method of claim 23, wherein the differences between the level of the post-translational modification of the individual signaling proteins is a decrease in the post-translational modification of two or more of the signaling proteins from the diseased cells in comparison to the same signaling proteins in the reference cells, and the therapeutic agents are selected to counteract the decrease in the level of the post-translational modification the individual signaling proteins from the diseased cells.

34. The method of claim 24, wherein the combination prevents shunting to or around a signaling pathway.

35. The method of claim 24, wherein the combination of therapeutic agents restores normal signaling patterns in diseased cells of the patient.

36. The method of claim 24, wherein the combination of therapeutic agents provides a synergistic normalization of the affected signaling proteins in diseased cells of the patient.

37. The method of claim 24, wherein the disease is cancer.

38. The method of claim 24, wherein the diseased cells are obtained by microdissection from tissue from the patient.

39. The method of claim 24, wherein measuring the phosphorylation of the signaling proteins comprises using protein microarray analysis.

40. The method of claim 24, wherein the differences between the level of the phosphorylation of the individual signaling proteins is an increase in the phosphorylation of two or more of the signaling proteins from the diseased cells in comparison to the same signaling proteins in the reference cells, and the therapeutic agents are selected to counteract the increase in the level of the phosphorylation of the individual signaling proteins from the diseased cells.

41. The method of claim 24, wherein the differences between the level of the phosphorylation of the individual signaling proteins is a decrease in the phosphorylation of two or more of the signaling proteins from the diseased cells in comparison to the same signaling proteins in the reference cells, and the therapeutic agents are selected to counteract the decrease in the level of the phosphorylation of the individual signaling proteins from the diseased cells.

42. The method of claim 24, wherein the disease is cancer, the diseased cells are obtained by laser capture microdissection from tissue from the patient, and measuring the phosphorylation of the signaling proteins comprises using reverse phase protein microarray analysis.

43. The method of claim 24, wherein the disease is cancer, the diseased cells are obtained by laser capture microdissection from tissue from the patient, measuring the phosphorylation of the signaling proteins comprises using reverse phase protein microarray analysis, and the combination prevents shunting to or around a signaling pathway.

44. The method of claim 43, wherein the combination of therapeutic agents restores normal signaling patterns in diseased cells of the patient.

45. A method for screening a combination of drugs to identify candidates for treatment of a disease in a patient caused by a peculiar, abnormal network of interconnected cell signaling proteins that leads to an aberrant cellular response in the patient, comprising the steps of:
   a) measuring activity states of a plurality of different signaling proteins extracted from diseased cells obtained from the patient;
   b) providing activity states of signaling proteins from reference cells corresponding to the signaling proteins extracted from the diseased cells obtained from the patient;
   c) detecting differences between the activity states of individual signaling proteins from the diseased cells and the activity states of the corresponding individual signaling proteins in the reference cells, thereby providing a snapshot of the signaling proteins in the diseased cells that form an abnormal network of interconnected cell signaling proteins that leads to the aberrant cellular response in the patient;
   d) administering a combination of at least two different drugs to the diseased cells;
   e) determining if the drugs reduce the difference that was detected in the activity states of two or more of the signaling proteins in the abnormal network of interconnected cell signaling proteins in the diseased cells compared to the activity states of the corresponding individual signaling proteins in the reference cells; and
   f) reporting drugs that reduce the difference as candidates for treating the disease.

46. The method of claim 45 further comprising treating the diseased cells with each of the drugs in the selected combination separately and at substantially the same dose as in the combination, examining the activity states of the signaling proteins after treatment with each of the drugs separately, and comparing such activity states to the activity states produced by the combination to determine if the combination synergistically reduces the difference that was detected in the activity states of two or more of the signaling proteins in the network of interconnected cell signaling proteins from the activity states of the corresponding signaling proteins in the reference cells.

47. The method of claim 45, wherein the activity states comprise a post-translational modification.

48. The method of claim 47, wherein the post-translational modification comprises phosphorylation.

49. The method of claim 45, wherein the abnormal network leads to abnormal cellular growth, motility, survival, differentiation, proliferation, or angiogenesis.

50. The method of claim 45, wherein the disease is cancer.

51. The method of claim 47, wherein the disease is cancer.

52. The method of claim 48, wherein the disease is cancer.

53. A method for using a protein microarray to identify a combination of therapeutic agents for individualized treatment of a disease in a patient caused by a peculiar, abnormal network of interconnected cell signaling proteins that leads to an aberrant cellular response in the patient, comprising the steps of:
   a) measuring with the protein microarray activity states for a plurality of different signaling proteins extracted from diseased cells obtained from the patient;
   b) providing activity states of signaling proteins from reference cells corresponding to the signaling proteins extracted from the diseased cells obtained from the patient;
   c) detecting differences between the activity states of the individual signaling proteins from the diseased cells and the activity states of the corresponding individual signaling proteins from the reference cells, thereby providing a snapshot of the signaling proteins in the diseased cells that form an abnormal network of interconnected cell signaling proteins that leads to the aberrant cellular response in the patient; and
   d) reporting a combination of at least two different therapeutic agents for administration to the patient for the purpose of correcting the abnormal network by reducing the difference that was detected in the activity states of two or more of the signaling proteins in the abnormal network of interconnected cell signaling proteins identified by steps (a)-(c) in the diseased cells from the activity states of the corresponding signaling proteins in the reference cells.

54. The method of claim 53, wherein the disease is caused by abnormal cellular growth, motility, survival, differentiation, proliferation, or angiogenesis.

55. The method of claim 53, wherein measuring the activity states of the proteins comprises measuring a post-translational modification of the proteins.

56. The method of claim 55, wherein the post-translational modification comprises phosphorylation.

57. The method of claim 56, wherein the disease is cancer.

58. The method of claim 9, wherein the diseased cells are obtained by laser capture microdissection from tissue from the patient.

59. The method of claim 17, wherein the diseased cells are obtained by laser capture microdissection from tissue from the patient.

60. The method of claim 57, wherein the diseased cells are obtained by microdissection from tissue from the patient, and measuring the phosphorylation of the signaling proteins comprises using reverse phase protein microarray analysis.

* * * * *